United States Patent
Brady et al.

(10) Patent No.: US 11,701,331 B2
(45) Date of Patent: Jul. 18, 2023

(54) TOXIC ALDEHYDE RELATED DISEASES AND TREATMENT

(71) Applicant: Aldeyra Therapeutics, Inc., Lexington, MA (US)

(72) Inventors: Todd Brady, Carlisle, MA (US); Scott Young, E. Falmouth, MA (US); William A. Kinney, Newtown, PA (US); Kenneth J. Mandell, Arlington, MA (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 0 days.

(21) Appl. No.: 17/227,568

(22) Filed: Apr. 12, 2021

(65) Prior Publication Data
US 2021/0275469 A1  Sep. 9, 2021

Related U.S. Application Data

(63) Continuation of application No. 16/773,654, filed on Jan. 27, 2020, now Pat. No. 11,007,157, which is a
(Continued)

(51) Int. Cl.
*A61K 31/137* (2006.01)
*A61K 31/47* (2006.01)
(Continued)

(52) U.S. Cl.
CPC .............. *A61K 31/137* (2013.01); *A61K 8/41* (2013.01); *A61K 8/44* (2013.01); *A61K 8/49* (2013.01);
(Continued)

(58) Field of Classification Search
CPC .......... A61K 31/137; A61K 8/41; A61K 8/44; A61K 8/49; A61K 8/4926; A61K 31/13;
(Continued)

(56) References Cited

U.S. PATENT DOCUMENTS

| | | |
|---|---|---|
| 2,086,186 A | 7/1937 | Messer |
| 3,912,748 A | 10/1975 | Evans et al. |

(Continued)

FOREIGN PATENT DOCUMENTS

| | | |
|---|---|---|
| CN | 1882339 A | 12/2006 |
| CN | 101048384 A | 10/2007 |

(Continued)

OTHER PUBLICATIONS

"Malondialdehyde," WikipediA, retrieved from Internet URL: "https://en.wikipedia.org/w/index.php?title=Malondialdehyde&oldid=993228459" on Aug. 4, 2021. Page last edited Dec. 9, 2020. (4 pages).

(Continued)

*Primary Examiner* — Taylor V Oh
(74) *Attorney, Agent, or Firm* — Dechert LLP; Andrea L. C. Reid; Joseph W. Arico

(57) ABSTRACT

The present invention provides for the treatment, prevention, and/or reduction of a risk of a disease, disorder, or condition in which aldehyde toxicity is implicated in the pathogenesis, including ocular disorders, skin disorders, conditions associated with injurious effects from blister agents, and autoimmune, inflammatory, neurological and cardiovascular diseases by the use of a primary amine to scavenge toxic aldehydes, such as MDA and HNE.

41 Claims, 7 Drawing Sheets

Related U.S. Application Data continuation of application No. 16/277,865, filed on Feb. 15, 2019, now Pat. No. 10,588,874, and a continuation of application No. 16/262,364, filed on Jan. 30, 2019, now Pat. No. 10,543,181, which is a continuation of application No. 15/590,708, filed on May 9, 2017, now Pat. No. 10,213,395, said application No. 16/277,865 is a continuation of application No. 15/590,708, filed on May 9, 2017, now Pat. No. 10,213,395, which is a continuation of application No. 14/760,039, filed as application No. PCT/US2014/012762 on Jan. 23, 2014, now Pat. No. 9,687,481.

(60) Provisional application No. 61/901,796, filed on Nov. 8, 2013, provisional application No. 61/755,613, filed on Jan. 23, 2013.

(51) Int. Cl.
```
A61K 31/197    (2006.01)
A61K 8/44      (2006.01)
A61K 8/41      (2006.01)
A61Q 19/00     (2006.01)
A61K 8/49      (2006.01)
A61Q 19/08     (2006.01)
A61K 31/13     (2006.01)
A61K 31/423    (2006.01)
A61K 31/438    (2006.01)
A61K 31/435    (2006.01)
C08K 5/04      (2006.01)
C08K 5/08      (2006.01)
C08K 5/18      (2006.01)
```

(52) U.S. Cl.
CPC ............ *A61K 8/4926* (2013.01); *A61K 31/13* (2013.01); *A61K 31/197* (2013.01); *A61K 31/423* (2013.01); *A61K 31/435* (2013.01); *A61K 31/438* (2013.01); *A61K 31/47* (2013.01); *A61Q 19/00* (2013.01); *A61Q 19/08* (2013.01); *C08K 5/04* (2013.01); *C08K 5/08* (2013.01); *C08K 5/18* (2013.01)

(58) Field of Classification Search
CPC .. A61K 31/197; A61K 31/423; A61K 31/435; A61K 31/438; A61K 31/47; A61K 31/41; A61Q 19/00; A61Q 19/08; C08K 5/04; C08K 5/08; C08K 5/18; A61P 1/00; A61P 3/00; A61P 3/04; A61P 3/06; A61P 3/10; A61P 9/00; A61P 9/10; A61P 11/00; A61P 11/06; A61P 17/00; A61P 17/02; A61P 17/06; A61P 17/10; A61P 19/02; A61P 21/02; A61P 25/00; A61P 25/16; A61P 25/28; A61P 27/00; A61P 27/02; A61P 27/12; A61P 29/00; A61P 31/04; A61P 37/00; A61P 37/02; A61P 37/08; A61P 39/02; A61P 43/00
USPC ........................................................ 514/311
See application file for complete search history.

(56) References Cited

U.S. PATENT DOCUMENTS

| | | |
|---|---|---|
| 4,668,626 A | 5/1987 | Kobayashi et al. |
| 4,956,351 A | 9/1990 | Mesens et al. |
| 5,024,998 A | 6/1991 | Bodor |
| 5,032,392 A | 7/1991 | Varma |
| 5,364,637 A | 11/1994 | De et al. |
| 5,376,645 A | 12/1994 | Stella et al. |
| 5,472,954 A | 12/1995 | Loftsson |
| 5,493,027 A | 2/1996 | Nichols et al. |
| 5,576,311 A | 11/1996 | Guy |
| 5,668,117 A | 9/1997 | Shapiro |
| 5,767,109 A | 6/1998 | Sanchez et al. |
| 5,998,488 A | 12/1999 | Shinohara et al. |
| 6,191,127 B1 | 2/2001 | Holscher et al. |
| 6,358,948 B1 | 3/2002 | Zhang et al. |
| 6,444,221 B1 | 9/2002 | Shapiro |
| 6,498,154 B1 | 12/2002 | Grubb et al. |
| 6,569,879 B2 | 5/2003 | Liu et al. |
| 7,083,803 B2 | 8/2006 | Peyman |
| 7,297,709 B2 | 11/2007 | Dai et al. |
| 7,531,564 B2 | 5/2009 | Malamas et al. |
| 7,973,025 B2 | 7/2011 | Jordan et al. |
| 7,982,071 B2 | 7/2011 | Scott et al. |
| 8,158,609 B1 | 4/2012 | Marsh et al. |
| 8,435,965 B2 | 5/2013 | Tabuchi et al. |
| 8,575,221 B2 | 11/2013 | Masse et al. |
| 8,722,669 B2 | 5/2014 | Palczewski et al. |
| 8,791,154 B2 | 7/2014 | Gamache et al. |
| 8,940,721 B2 | 1/2015 | Jordan et al. |
| 8,940,764 B2 | 1/2015 | Jordan et al. |
| 9,067,963 B2 | 6/2015 | Thompson et al. |
| 9,265,759 B2 | 2/2016 | Jordan et al. |
| 9,364,471 B2 | 6/2016 | Jordan et al. |
| 9,375,408 B2 | 6/2016 | Singh |
| 9,604,997 B2 | 3/2017 | Jordan et al. |
| 9,650,342 B2 | 5/2017 | Jordan et al. |
| 9,687,481 B2 | 6/2017 | Brady et al. |
| 9,896,419 B2 | 2/2018 | Jordan et al. |
| 10,058,095 B2 | 8/2018 | Czarnik |
| 10,111,862 B2 | 10/2018 | Chabala et al. |
| 10,202,348 B2 | 2/2019 | Jordan et al. |
| 10,213,395 B2 | 2/2019 | Brady et al. |
| 10,414,732 B2 | 9/2019 | Buist et al. |
| 10,426,790 B2 | 10/2019 | Young et al. |
| 10,543,181 B2 | 1/2020 | Brady et al. |
| 10,550,085 B2 | 2/2020 | Brady et al. |
| 10,588,874 B2 | 3/2020 | Brady et al. |
| 10,913,722 B2 | 2/2021 | Jordan et al. |
| 11,007,157 B2 | 5/2021 | Brady et al. |
| 11,040,039 B2 | 6/2021 | Macdonald et al. |
| 11,046,650 B2 | 6/2021 | Brady et al. |
| 11,129,823 B2 | 9/2021 | Brady et al. |
| 11,197,821 B2 | 12/2021 | Clark et al. |
| 11,312,692 B1 | 4/2022 | Machatha et al. |
| 2004/0132636 A1 | 7/2004 | Dooley et al. |
| 2004/0198828 A1 | 10/2004 | Abelson et al. |
| 2004/0235892 A1 | 11/2004 | Dai et al. |
| 2005/0020603 A1 | 1/2005 | Dai et al. |
| 2005/0090553 A1 | 4/2005 | Shapiro |
| 2005/0130906 A1 | 6/2005 | Matier et al. |
| 2005/0197292 A1 | 9/2005 | Smithson et al. |
| 2005/0234018 A1 | 10/2005 | Lyons et al. |
| 2006/0014786 A1 | 1/2006 | Raut |
| 2006/0111318 A1 | 5/2006 | Okamoto |
| 2006/0183909 A1 | 8/2006 | Schmitt et al. |
| 2006/0189608 A1 | 8/2006 | Bingaman |
| 2007/0129404 A1 | 6/2007 | Hagihara et al. |
| 2007/0135481 A1 | 6/2007 | Jordan et al. |
| 2007/0243257 A1 | 10/2007 | Bedos et al. |
| 2007/0297981 A1 | 12/2007 | Ousler et al. |
| 2009/0118503 A1 | 5/2009 | Sprott et al. |
| 2009/0182009 A1 | 7/2009 | Jordan et al. |
| 2010/0240624 A1 | 9/2010 | Chapin et al. |
| 2010/0331315 A1 | 12/2010 | Haddach et al. |
| 2011/0071091 A1 | 3/2011 | Chowhan et al. |
| 2011/0105450 A1 | 5/2011 | Chapin et al. |
| 2011/0263645 A1 | 10/2011 | Jordan et al. |
| 2012/0108585 A1 | 5/2012 | Vu |
| 2012/0302601 A1 | 11/2012 | Jordan et al. |
| 2013/0190500 A1 | 7/2013 | Greiner et al. |
| 2014/0038918 A1 | 2/2014 | Rodriguez-Boulan et al. |
| 2014/0050797 A1 | 2/2014 | Venkatesh et al. |
| 2014/0235604 A1 | 8/2014 | Palczewski et al. |
| 2015/0209333 A1 | 7/2015 | Jordan et al. |
| 2015/0209345 A1 | 7/2015 | Jordan et al. |
| 2015/0335632 A1 | 11/2015 | Brady et al. |

(56) References Cited

U.S. PATENT DOCUMENTS

| | | |
|---|---|---|
| 2015/0344432 A1 | 12/2015 | Jordan et al. |
| 2015/0344447 A1 | 12/2015 | Chabala et al. |
| 2016/0052930 A1 | 2/2016 | Fensome et al. |
| 2016/0168098 A1 | 6/2016 | Jordan et al. |
| 2017/0029354 A1 | 2/2017 | Singh |
| 2017/0239196 A1 | 8/2017 | Brady et al. |
| 2017/0266220 A1 | 9/2017 | Young et al. |
| 2017/0320829 A1 | 11/2017 | Jordan et al. |
| 2017/0354655 A1 | 12/2017 | Beaupre et al. |
| 2018/0050989 A1 | 2/2018 | Machatha et al. |
| 2018/0092882 A1 | 4/2018 | Jordan et al. |
| 2018/0194733 A1 | 7/2018 | Jordan et al. |
| 2018/0250306 A1 | 9/2018 | Brady et al. |
| 2018/0265474 A1 | 9/2018 | Buist et al. |
| 2018/0354905 A1 | 12/2018 | Brady et al. |
| 2019/0183878 A1 | 6/2019 | Brady et al. |
| 2019/0210971 A1 | 7/2019 | Jordan et al. |
| 2019/0231715 A1 | 8/2019 | Brady et al. |
| 2020/0038392 A1 | 2/2020 | Brady et al. |
| 2020/0062712 A1 | 2/2020 | Machatha et al. |
| 2020/0121591 A1 | 4/2020 | Clark et al. |
| 2020/0246345 A1 | 8/2020 | Brady et al. |
| 2020/0323841 A1 | 10/2020 | Clark et al. |
| 2020/0368182 A1 | 11/2020 | Brady et al. |
| 2021/0269402 A1 | 9/2021 | Jordan et al. |
| 2021/0347735 A1 | 11/2021 | Brady et al. |
| 2021/0353628 A1 | 11/2021 | Macdonald et al. |
| 2021/0393527 A1 | 12/2021 | Brady et al. |
| 2021/0393612 A1 | 12/2021 | Machatha et al. |
| 2022/0017475 A1 | 1/2022 | Machatha et al. |
| 2022/0089542 A1 | 3/2022 | Machatha et al. |
| 2022/0133629 A1 | 5/2022 | Clark et al. |
| 2022/0133697 A1 | 5/2022 | Machatha et al. |

FOREIGN PATENT DOCUMENTS

| | | |
|---|---|---|
| CN | 101321742 A | 12/2008 |
| CN | 101534826 A | 9/2009 |
| CN | 101611009 A | 12/2009 |
| CN | 1830964 B | 6/2011 |
| CN | 108135867 A | 6/2018 |
| EP | 0186367 A2 | 7/1986 |
| EP | 0245054 A1 | 11/1987 |
| EP | 0483881 A1 | 5/1992 |
| EP | 2301549 A1 | 3/2011 |
| EP | 1888548 B1 | 8/2012 |
| JP | 2002003364 A | 1/2002 |
| JP | 2005-132834 A | 5/2005 |
| JP | 3736916 B2 | 1/2006 |
| JP | 2007532648 A | 11/2007 |
| JP | 2008542291 A | 11/2008 |
| JP | 4466875 B2 | 5/2010 |
| JP | 4748289 B2 | 8/2011 |
| JP | 5194218 B2 | 5/2013 |
| RU | 2565448 C2 | 10/2015 |
| SU | 50906 A1 | 11/1936 |
| WO | WO-1996022992 A1 | 8/1996 |
| WO | WO-1998005645 A1 | 2/1998 |
| WO | WO-1999046237 A1 | 9/1999 |
| WO | WO-2001041757 A1 | 6/2001 |
| WO | WO-2004082622 A2 | 9/2004 |
| WO | WO-2004091630 A1 | 10/2004 |
| WO | WO-2005035506 A1 | 4/2005 |
| WO | WO-2005040151 A1 | 5/2005 |
| WO | WO-2005079774 A2 | 9/2005 |
| WO | WO-2006000421 A2 | 1/2006 |
| WO | WO-2006002473 A1 | 1/2006 |
| WO | WO-2006077821 A1 | 7/2006 |
| WO | WO-2006127945 A1 | 11/2006 |
| WO | WO-2007118276 A1 | 10/2007 |
| WO | WO-2009045479 A1 | 4/2009 |
| WO | WO-2009102418 A1 | 8/2009 |
| WO | WO-2010133672 A1 | 11/2010 |
| WO | WO-2011008202 A1 | 1/2011 |
| WO | WO-2011071995 A2 | 6/2011 |
| WO | WO-2011072141 A1 | 6/2011 |
| WO | WO-2011078204 A1 | 6/2011 |
| WO | WO-2012097173 A2 | 7/2012 |
| WO | WO-2012105887 A1 | 8/2012 |
| WO | WO-2014100425 A1 | 6/2014 |
| WO | WO-2014116593 A1 | 7/2014 |
| WO | WO-2014116836 A2 | 7/2014 |
| WO | WO-2015002893 A1 | 1/2015 |
| WO | WO-2015187942 A1 | 12/2015 |
| WO | WO-2016085939 A2 | 6/2016 |
| WO | WO-2017035077 A1 | 3/2017 |
| WO | WO-2017035082 A1 | 3/2017 |
| WO | WO-2017147617 A1 | 8/2017 |
| WO | WO-2017196881 A1 | 11/2017 |
| WO | WO-2018039192 A1 | 3/2018 |
| WO | WO-2018039197 A1 | 3/2018 |
| WO | WO-2018064354 A1 | 4/2018 |
| WO | WO-2018170476 A1 | 9/2018 |
| WO | WO-2019075136 A1 | 4/2019 |
| WO | WO-2020018498 A1 | 1/2020 |
| WO | WO-2020028820 A1 | 2/2020 |
| WO | WO-2020033344 A1 | 2/2020 |
| WO | WO-2020068986 A1 | 4/2020 |
| WO | WO-2020072621 A1 | 4/2020 |
| WO | WO-2020118045 A1 | 6/2020 |
| WO | WO-2020198064 A1 | 10/2020 |
| WO | WO-2020223685 A1 | 11/2020 |
| WO | WO-2020223717 A1 | 11/2020 |
| WO | 2021195211 A1 | 9/2021 |
| WO | 2021211625 A1 | 10/2021 |
| WO | 2021231792 A1 | 11/2021 |
| WO | 2021248031 A1 | 12/2021 |

OTHER PUBLICATIONS

Brandt et al., "The Prevalence of Non-Alcoholic Fatty Liver Disease in Patients With Inflammatory Bowel Disease," American Journal of Gastroenterology. 2017;112:S542,S544.

Chao et al., "Co-existence of non-alcoholic fatty liver disease and inflammatory bowel disease: A review article," World J Gastroenterol. 2016;22(34):7727-34.

International Search Report and Written Opinion from PCT/US2022/011604 dated Mar. 4, 2022.

International Search Report and Written Opinion issued by the United States Patent and Trademark Office as International Searching Authority for International Patent Application No. PCT/US2021/023884, dated Jul. 28, 2021 (11 pages).

International Search Report and Written Opinion issued by the United States Patent and Trademark Office as International Searching Authority for International Patent Application No. PCT/US2021/027148, dated Jun. 28, 2021 (9 pages).

International Search Report and Written Opinion issued by the United States Patent and Trademark Office as International Searching Authority for International Patent Application No. PCT/US2021/032335, dated Jul. 27, 2021 (11 pages).

International Search Report and Written Opinion issued by the United States Patent and Trademark Office as International Searching Authority for International Patent Application No. PCT/US2021/035948, dated Oct. 26, 2021 (12 pages).

Roumen et al. "Serum lipofuscin as a prognostic indicator of adult respiratory distress syndrome and multiple organ failure," Br J Surg. 1994; 81(9):1300-5.

Serajuddin, "Salt formation to improve drug solubility," Adv Drug Deliv Rev. 2007;59(7):603-16.

U.S. Appl. No. 17/164,556 of Jordan et al., filed Feb. 21, 2021.
U.S. Appl. No. 17/265,757 of Machatha et al., filed Feb. 3, 2021.
U.S. Appl. No. 17/282,301 of MacDonald et al., filed Apr. 1, 2021.
U.S. Appl. No. 17/299,731 of Machatha et al., filed Jun. 3, 2021.
U.S. Appl. No. 17/310,104 of Machatha et al., filed Jul. 16, 2021.
U.S. Appl. No. 17/324,318 of Brady et al., filed May 19, 2021.
U.S. Appl. No. 17/328,772 of MacDonald et al., filed May 24, 2021.
U.S. Appl. No. 17/333,528 of Brady et al., filed May 28, 2021—Published.
U.S. Appl. No. 17/334,094 of Machatha et al., filed May 28, 2021.
U.S. Appl. No. 17/450,623 of Clark et al., filed Oct. 21, 2021.

(56) References Cited

OTHER PUBLICATIONS

Winfield and Richards, "Ophthalmic Products," Pharmaceutical Practice, Published by Churchill Livingstone, 2004; 265-268.
Abelson et al., "Combined analysis of two studies using the conjunctival allergen challenge model to evaluate olopatadine hydrochloride, a new ophthalmic antiallergic agent with dual activity," American Journal of Ophthalmology, 125(6):797-804 (Jun. 1998).
Abelson et al., "Conjunctival allergen challenge. A clinical approach to studying allergic conjunctivitis," Archives of Ophthalmology, 108(1):84-88 (1990).
Abelson et al., "Conjunctival allergen challenge: models in the investigation of ocular allergy," Current Allergy and Asthma Reports, 3(4):363-368 (2003).
Abelson et al., The conjunctival provocation test model of ocular allergy: utility for assessment of an ocular corticosteroid, loteprednol etabonate, J Ocul Pharmacol Ther, 14(6):533-42 (Dec. 1998).
Abramovitz, M. et al., "The utilization of recombinant prostanoid receptors to determine the affinities and selectivities of prostaglandins and related analogs," Biochem. Biophys. Acta., 1483(2):285-293 (2000).
Ackerman et al., "Ocular itch associated with allergic conjunctivitis: latest evidence and clinical management," Ther. Adv. Chronic Dis., 2016; 7(1):52-67.
Acland et al., "Gene Therapy Restores Vision in a Canine Model of Childhood Blindness," Nature Genetics, 28(1):92-95 (2001).
Aharony, D. et al., "Pharmacological characterization of cloned human NK-2 (neurokinin A) receptor expressed in a baculovirus/Sf-21 insect cell system," Molecular Pharmacology, 44(2):356-363 (1993).
Akturk, S. et al., "Nitric oxide and malondialdehyde levels in plasma and tissue of psoriasis patients," Journal of the European Academy of Dermatology and Venereology, 26(7):833-837 (2012).
Al-Essa et al., "Clinical, fluorine-18 labeled 2-fluoro-2-deoxyglucose positron emission tomography (FDG PET), MRI of the brain and biochemical observations in a patient with 4-hydroxybutyric aciduria; a progressive neurometabolic disease," Brain Dev., 22(2):127-31 (2000).
Al-Hasani, H. et al., "Phosphoryl exchange is involved in the mechanism of the insulin receptor kinase," FEBS Lett., 349:17-22 (1994).
Albano et al., "Immune response towards lipid peroxidation products as a predictor of progression of non-alcoholic fatty liver disease to advanced fibrosis," Gut 54:987-93 (2005).
Aldeyra Press Release—Aldeyra Therapeutics Abstract Accepted at 2015 American Academy of Allergy Asthma & Immunology Annual Meeting, Dec. 16, 2014 (2 pages).
Aldeyra Press Release—Aldeyra Therapeutics Abstract Accepted for Presentation at the 2015 Multinational Association of Supportive Care in Cancer—International Society of Oral Oncology (MASCCISOO) Annual Meeting, Apr. 23, 2015 (2 pages).
Aldeyra Press Release—Aldeyra Therapeutics Abstracts Accepted for Presentation at the 2015 Annual Meeting of the Association for Research in Vision and Ophthalmology, Feb. 2, 2015 (2 pages).
Aldeyra Press Release—Aldeyra Therapeutics Announces Agreement with Johnson & Johnson Innovation to Advance Novel Immune-Modulating Drugs for Systemic Inflammatory Diseases, Feb. 27, 2018 (2 pages).
Aldeyra Press Release—Aldeyra Therapeutics Announces Clinical Development Update for Phase 3 Programs, Jan. 25, 2017 (2 pages).
Aldeyra Press Release—Aldeyra Therapeutics Announces Collaboration With the National Organization for Rare Disorders to Enhance Awareness for Sjogren-Larsson Syndrome Patients, Dec. 4, 2014 (2 pages).
Aldeyra Press Release—Aldeyra Therapeutics Announces Development Programs at 2018 Research Day, Jun. 26, 2018 (2 pages).
Aldeyra Press Release—Aldeyra Therapeutics Announces First Patient Enrolled in Allergic Conjunctivitis Phase 2b Clinical Trial, Feb. 7, 2017 (2 pages).
Aldeyra Press Release—Aldeyra Therapeutics Announces First Patient Enrolled in Allergic Conjunctivitis Phase 3 Clinical Trial, Apr. 24, 2018 (2 pages).
Aldeyra Press Release—Aldeyra Therapeutics Announces First Patient Enrolled in Allergic Conjunctivitis Phase IIa Clinical Trial, Sep. 29, 2015 (2 pages).
Aldeyra Press Release—Aldeyra Therapeutics Announces First Patient Enrolled in Dry Eye Disease Phase 2a Clinical Trial, Jun. 6, 2017 (2 pages).
Aldeyra Press Release—Aldeyra Therapeutics Announces First Patient Enrolled in Dry Eye Disease Phase 2b Clinical Trial, Jan. 30, 2018 (2 pages).
Aldeyra Press Release—Aldeyra Therapeutics Announces First Patient Enrolled in Noninfectious Anterior Uveitis Phase 3 Clinical Trial, Apr. 27, 2017 (2 pages).
Aldeyra Press Release—Aldeyra Therapeutics Announces First Patient Enrolled in Noninfectious Anterior Uveitis Phase II Clinical Trial, Apr. 16, 2015 (2 pages).
Aldeyra Press Release—Aldeyra Therapeutics Announces First Patient Enrolled in Sjogren-Larsson Syndrome Phase II Clinical Trial, Mar. 24, 2015 (2 pages).
Aldeyra Press Release—Aldeyra Therapeutics Announces First Patient Enrolled in Sjögren-Larsson Syndrome Pivotal Phase 3 Clinical Trial, Jul. 24, 2018 (2 pages).
Aldeyra Press Release—Aldeyra Therapeutics Announces Last Patient Dosed in Dry Eye Disease Phase 2a Clinical Trial, Jul. 18, 2017 (2 pages).
Aldeyra Press Release—Aldeyra Therapeutics Announces Last Patient Dosed in Dry Eye Disease Phase 2b Clinical Trial, Jul. 12, 2018 (2 pages).
Aldeyra Press Release—Aldeyra Therapeutics Announces Last Patient Dosed in Phase II Trial of NS2 in Patients with Allergic Conjunctivitis, Dec. 16, 2015 (2 pages).
Aldeyra Press Release—Aldeyra Therapeutics Announces Last Patient Dosed in the ALLEVIATE Phase 3 Clinical Trial, Dec. 20, 2018 (2 pages).
Aldeyra Press Release—Aldeyra Therapeutics Announces Positive Mesothelioma Investigator-Sponsored Clinical Trial Results Presented at the International Association for the Study of Lung Cancer 19th World Conference on Lung Cancer, Sep. 25, 2018 (2 pages).
Aldeyra Press Release—Aldeyra Therapeutics Announces Positive Results from Dry Eye Disease Phase 2a Clinical Trial, Sep. 12, 2017 (3 pages).
Aldeyra Press Release—Aldeyra Therapeutics Announces Positive Results from Phase 2b Dry Eye Disease Clinical Trial, Sep. 26, 2018 (2 pages).
Aldeyra Press Release—Aldeyra Therapeutics Announces Positive Top-Line Results from the Phase 3 ALLEVIATE Trial in Patients with Allergic Conjunctivitis, Mar. 26, 2019 (2 pages).
Aldeyra Press Release—Aldeyra Therapeutics Announces Presentation of Novel Data on the Efficacy of ADX-102 in a Model of Succinic Semialdehyde Dehydrogenase Activity at the 2017 American Society of Human Genetics Annual Meeting, Oct. 5, 2017 (2 pages).
Aldeyra Press Release—Aldeyra Therapeutics Announces Presentation of Phase 2 Allergic Conjunctivitis Results at the 2016 American College of Allergy, Asthma and Immunology Annual Scientific Meeting, Nov. 7, 2016 (2 pages).
Aldeyra Press Release—Aldeyra Therapeutics Announces Presentation of Results on the Efficacy of ADX-102 in Noninfectious Anterior Uveitis at the American Uveitis Society Held at the American Academy of Ophthalmology 2017 Annual Meeting, Oct. 25, 2017 (2 pages).
Aldeyra Press Release—Aldeyra Therapeutics Announces Results from Allergic Conjunctivitis Phase 2b Clinical Trial and Plans for Phase 3 Clinical Testing, Jun. 14, 2017 (3 pages).
Aldeyra Press Release—Aldeyra Therapeutics Announces Third Quarter 2017 Financial Results, Nov. 9, 2017 (4 pages).
Aldeyra Press Release—Aldeyra Therapeutics Launches the Aldeyra Registry for Patients with Sjögren-Larsson Syndrome, Feb. 22, 2017 (2 pages).

(56) References Cited

OTHER PUBLICATIONS

Aldeyra Press Release—Aldeyra Therapeutics Opens Enrollment in Noninfectious Anterior Uveitis Phase II Clinical Trial, Mar. 26, 2015 (2 pages).
Aldeyra Press Release—Aldeyra Therapeutics Opens Enrollment in Sjogren-Larsson Syndrome Clinical Trial and Finalizes Noninfectious Anterior Uveitis Clinical Trial Protocol, Mar. 17, 2015 (2 pages).
Aldeyra Press Release—Aldeyra Therapeutics Presents Dry Eye Disease Phase 2a Clinical Trial Results at the Association for Research in Vision and Ophthalmology 2018 Annual Meeting, May 2018 (2 pages).
Aldeyra Press Release—Aldeyra Therapeutics Presents Evidence for Aldehyde Sequestration as a Potential Therapeutic Approach in Succinic Semialdehyde Dehydrogenase Deficiency at the American Society of Human Genetics 2017 Annual Meeting, Oct. 24, 2017 (2 pages).
Aldeyra Press Release—Aldeyra Therapeutics Presents Noninfectious Anterior Uveitis Phase 2 Clinical Trial Data at the Association for Research in Vision and Ophthalmology 2017 Annual Meeting, May 17, 2017 (3 pages).
Aldeyra Press Release—Aldeyra Therapeutics Presents Noninfectious Anterior Uveitis Phase 2 Clinical Trial Data to the American Uveitis Society Held at the American Academy of Ophthalmology 2017 Annual Meeting, Nov. 29, 2017 (2 pages).
Aldeyra Press Release—Aldeyra Therapeutics Provides Update on Late-Stage Clinical Trials at 2016 Research and Development Day, Sep. 26, 2016 (2 pages).
Aldeyra Press Release—Aldeyra Therapeutics Provides Update on NS2 Clinical Program, Mar. 2015 (2 pages).
Aldeyra Press Release—Aldeyra Therapeutics Provides Update on Ophthalmic Programs at 2019 Research & Development Day, Feb. 28, 2019 (2 pages).
Aldeyra Press Release—Aldeyra Therapeutics Schedules Conference Call and Webcast to Announce Results from Allergic Conjunctivitis Phase 2b Clinical Trial, Jun. 13, 2017 (1 page).
Aldeyra Press Release—Aldeyra Therapeutics Schedules Conference Call to Present Results of a Randomized, Double-Blind, Vehicle-Controlled Clinical Trial in Sjogren-Larsson Syndrome, Aug. 8, 2016 (2 pages).
Aldeyra Press Release—Aldeyra Therapeutics Schedules Webcast and Conference Call to Announce Results from Dry Eye Disease Phase 2a Clinical Trial, Sep. 11, 2017 (1 page).
Aldeyra Press Release—Aldeyra Therapeutics Selected for Podium Presentation of Phase 2a Dry Eye Disease Results at the 2018 Association for Research in Vision and Ophthalmology (ARVO) Annual Meeting, Feb. 21, 2018 (3 pages).
Aldeyra Press Release—Aldeyra Therapeutics Submits FDA IND Filing for Noninfectious Anterior Uveitis, Dec. 18, 2014 (2 pages).
Aldeyra Press Release - Aldeyra Therapeutics Submits IND Filing to FDA for Clinical Testing of NS2 in Patients With Sjogren-Larsson Syndrome, Jan. 5, 2015 (2 pages).
Aldeyra Press Release—Aldeyra Therapeutics to Host 2019 Research & Development Day, Feb. 12, 2019 (1 page).
Aldeyra Press Release—Aldeyra Therapeutics to Present at the 2016 SSADH Symposium, Mar. 24, 2016 (1 page).
Aldeyra Press Release—Aldeyra Therapeutics to Present Novel Data on a Potential Treatment for Sjogren-Larsson Syndrome at the 2015 Society for Inherited Metabolic Disorders Annual Meeting, Jan. 29, 2015 (2 pages).
Aldeyra Press Release—Aldeyra Therapeutics to Present Novel Data on a Potential Treatment for Succinic Semi-Aldehyde Dehydrogenase Deficiency at the 2015 American Society of Human Genetics (ASHG) Annual Meeting, Sep. 9, 2015 (2 pages).
Aldeyra Press Release—Aldeyra Therapeutics' Data on Lead Candidate NS2 to be Presented at Society for Investigative Dermatology 2014 Annual Meeting, May 8, 2014 (2 pages).
Aldeyra Press Release—Aldeyra Therapeutics, Inc. Announces Last Patient Dosed in Allergic Conjunctivitis Phase 2b Clinical Trial, Apr. 18, 2017 (2 pages).
Aldeyra Press Release—Aldeyra Therapeutics, Inc. Announces Last Patient Dosed in Phase II Clinical Trial of Topical Dermatologic NS2 in Patients With Sjögren-Larsson Syndrome Jun. 7, 2016 (2 pages).
Aldeyra Press Release—Aldeyra Therapeutics, Inc. Receives Orphan Drug Designation from the U.S. Food and Drug Administration for ADX-102 in Sjögren-Larsson Syndrome, Apr. 20, 2017 (2 pages).
Aldeyra Press Release—Positive Results From Phase II Clinical Trial in Subjects With Noninfectious Anterior Uveitis, May 9, 2016 (4 pages).
Aldini et al., "Lipoxidation-Derived Reactive Carbonyl Species as Potential Drug Targets in Preventing Protein Carbonylation and Related Cellular Dysfunction," ChemMedChem, 1(10):1045-1058 (2006).
Aldini et al., "The carbonyl scavenger carnosine ameliorates dyslipidaemia and renal function in Zucker obese rats," The Journal of Cellular and Molecular Medicine, 15(6):1339-1354 (2011).
Amara et al., "Autoantibodies to malondialdehyde-modified epitope in connective tissue disease and vasculitides," Clinical and Experimental Immunology, 101(2):233-238 (1995).
Ao et al., "Methyl-β-Cyclodextrin Impairs the Monocyte-Adhering Ability of Endothelial Cells by Down-Regulating Adhesion Molecules and Caveolae and Reorganizing the Actin Cytoskeleton," Biol Pharm Bull, 39(6):1029-1034 (2016).
Apparsundaram, S. et al., "Molecular cloning of a human, hemicholinium-3-sensitive choline transporter," Biochem. Biophys. Res. Commun., 276(3):862-867 (2000).
Ardati, A. et al., "Interaction of [3H]orphanin FQ and 125I-Tyr14-orphanin FQ with the orphanin FQ receptor: kinetics and modulation by cations and guanine nucleotides," Mol. Pharmacol., 51:816-824 (1997).
Ashton et al., "Location of penetration and metabolic barriers to levobunolol in the corneal epithelium of the pigmented rabbit," The Journal of Pharmacology and Experimental Therapeutics, 259(2):719-724 (1991).
Atkinson et al., "Triazaphenanthrenes. Part VI. Further Observations on the Widman-Stoermer and Brosche Reactions," J. Chem. Soc. (C) pp. 2053-2060 (1966).
Augustin et al., "Oxidative reactions in the tear fluid of patients suffering from dry eyes," Graefe's Archive for Clinical and Experimental Ophthalmology, 233(11):694-698 (1995).
Axelsson et al., "Experimental colitis induced by dextran sulphate sodium in mice: beneficial effects of sulphasalazine and olsalazine," Aliment Pharmacol Ther, 12:925-934 (1998).
Bachman, G.B. et al., "Quinoline derivatives from 3-nitro-4-hydroxyquinoline," Am. Chem. Soc., 69:365-371 (1947).
Bacsi et al., "Effect of pollen-mediated oxidative stress on immediate hypersensitivity reactions and late-phase inflammation in allergic conjunctivitis," J. Allergy Clin. Immunol., 2005; 116(4):836-843.
Badii, "Allergic Conjunctivitis," https://www.healthline.com/health/allergic-conjunctivitis, Apr. 28, 2016 (12 pages) [retrieved on Nov. 22, 2019].
Balci et al., "Effects of computer monitor-emitted radiation on oxidant/antioxidant balance in cornea and lens from rats," Molec Vis, 15:2521-2525 (2009).
Balci et al., "Investigation of oxidative stress in pterygium tissue," Molecular Vision, 17:443-447 (Feb. 2011).
Ballard, S.A. et al., "Effects of sildenafil on the relaxation of human corpus cavernosum tissue in vitro and on the activities of cyclic nucleotide phosphodiesterase isozymes," J. Urol., 159(6):2164-2171 (1998).
Baltatzis et al., "Mycophenolate mofetil as an immunomodulatory agent in the treatment of chronic ocular inflammatory disorders," Ophthalmology, 110(5):1061-5 (May 2003).
Bardwell, A.J. et al., "Docking sites on mitogen-activated protein kinase (MAPK) kinases, MAPK phosphatases and the Elk-1 transcription factor compete for MAPK binding and are crucial for enzymic activity," Biochem. J., 370:1077-1085 (2003).
Baron, B.M. et al., "[3H]MDL 105,519, a high-affinity radioligand for the N-methyl-D-aspartate receptor-associated glycine recognition site," J. Pharmacol. Exp. Ther., 279:62-68 (1996).

(56) References Cited

OTHER PUBLICATIONS

Bartoli et al., "Malondialdehyde in Exhaled Breath Condensate as a Marker of Oxidative Stress in Different Pulmonary Diseases," Mediators of Inflammation, vol. 2011, Article ID 891752 (2011) (7 pages).
Batista et al., "Age-dependent changes in rat lacrimal gland antioxidant and vesicular related protein expression profiles," Molecular Vision, 18:194-202 (2012).
Batista et al., "Short-term treatment with bisphenol-A leads to metabolic abnormalities in adult male mice," PLOS One, vol. 7, No. 3, (2012).
Baum et al, "Omega 3 fatty acid inhibition of inflammatory cytokine-mediated Connexin43 regulation in the heart," Front. Physiol. 3:272 doi: 10.3389/fphys.2012.00272. eCollection 2012 (2012).
Baz et al., "Plasma reactive oxygen species activity and antioxidant potential levels in rosacea patients: correlation with seropositivity to Helicobacter pylori," International Journal of Dermatology, 43(7):494-497 (2004).
Berge et al., "Pharmaceutical salts," The Journal of Pharmaceuticals Sciences, 66(1):1-19 (1977).
Berkhout, T.A. et al., "Cloning, in vitro expression, and functional characterization of a novel human CC chemokine of the monocyte chemotactic protein (MCP) family (Mcp-4) that binds and signals through the CC chemokine receptor 2B,", J. Biol. Chem., 272:16404-16413 (1997).
Bermudez et al., "Thermosensitive poloxamer-based injectables as controlled drug release platforms for veterinary use: Development and in-vitro evaluation," Intl Res J Pharmacy Pharmacol, 1(6):109-118 (Sep. 2011).
Bernstein et al., "Mechanism of Action of Aromatic Amines that Short-Circuit the Visual Cycle," Biochemistry, 25(11):3370-3377 (1986).
Bernstein et al., "Retinal Toxicity Associated with Occupational Exposure to the Fish Anesthetic MS-222," Am J Ophthalmol, 124(6):843-844 (1997).
Bernstein et al., "Short-Circuiting the Visual Cycle with Retinotoxic Aromatic Amines," Proc Natl Acad Sci USA, 83(6):1632-1635 (1986).
Bernstein et al., The Specific Inhibition of 11-cis-retinyl Palmitate Formation in the Frog Eye by Diaminophenoxypentane, an Inhibitor of Rhodopsin Regeneration, Vision Research, 25(6):741-748 (1985).
Bickett, D.A. et al., "A high throughput fluorogenic substrate for interstitial collagenase (MMP-1) and gelatinase (MMP-9)," Anal. Biochem., 212:58-64 (1993).
Bignon, E. et al., "SR146131: a new potent, orally active, and selective nonpeptide cholecystokinin subtype 1 receptor agonist. I. In vitro studies," J. Pharmacol. Exp. Ther. 289:742-751 (1999).
Blindauer et al., "A randomized controlled trial of etilevodopa in patients with Parkinson disease who have motor fluctuations," Arch Neurol, 63(2):210-6 (Feb. 2006).
Boldogh et al., "ROS generated by pollen NADPH oxidase provide a signal that augments antigen-induced allergic airway inflammation," J. Clin. Invest., 2005; 115(8):2169-2179.
Boner et al., "Bronchodilating activity of oral clenbuterol in asthmatic children after single administration of different dosages," Pediatr Pulmonol, 3(1):34-7 (Jan.-Feb. 1987).
Bousquet et al., "How to Design and Evaluate Randomized Controlled Trials in Immunotherapy for Allergic Rhinitis: An ARIA-GA2 LEN Statement," Allergy, 66(6):765-774 (2011).
Boyer et al., "Lipofuscin and N-Retinylidene-N-Retinylethanolamine (A2E) Accumulate in Retinal Pigment Epithelium in Absence of Light Exposure," J Biol Chem, 287(26):22276-22286 (Jun. 2012).
Bozkir et al., "Effect of hydroxypropyl-beta-cyclodextrin on the solubility, stability and in-vitro release of ciprofloxacin for ocular drug delivery," Acta Poloniae Pharmaceutica, 69(4):719-24 (2012).
Bragagni et al., "Cyclodextrin complexation highly enhances efficacy of arylsulfonylureido benzenesulfonamide carbonic anhydrase inhibitors as a topical antiglaucoma agents," Bioorganic & Medicinal Chemistry, 23(18):6223-6227) (2015).
Brenneman et al., "Cannabidiol Provides Protection from Ethanol and Ammonium toxicity in a Hippocampal Model of Hepatic Encephalopathy," 24th Annual Symposium of the International Cannabinoid Research Society, Baveno, Italy, Jun. 28-Jun. 3, 2014 (p. 73).
Brenneman et al., "Small Molecule Anticonvulsant Agents with Potent in Vitro Neuroprotection," Journal of Molecular Neuroscience, 47(2):368-379 (2012).
Brewitt et al., "Dry Eye Disease—The Scale of the Problem," Survey of Ophthalmol, 45(Suppl 2):S199-S2 (Mar. 2001).
BRIDION® (sugammadex) Injection Prescribing Information, for intravenous use, Initial U.S. Approval: 2015, Last Revised Dec. 2015 (19 pages).
Brockhaus, M. et al., "Identification of two types of tumor necrosis factor receptors on human cell lines by monoclonal antibodies," Proc. Natl. Acad. Sci. U.S.A., 87:3127-3131 (1990).
Brown, G.B., "3H-batrachotoxinin-A benzoate binding to voltage-sensitive sodium channels: inhibition by the channel blockers tetrodotoxin and saxitoxin," J. Neurosci., 6:2064-2070 (1986).
Brozek et al., "Grading quality of evidence and strength of recommendations in clinical practice guidelines: Part 2 of 3. The GRADE approach to grading quality of evidence about diagonstic tests and strategies," Allergy, 64(8):1109-1116 (2009).
Bryant, H.U. et al., "A novel class of 5-HT2A receptor antagonists: aryl aminoguanidines," Life Sci., 59(15):1259-1268 (1996).
Bucciantini et al., "Inherent Toxicity of Aggregates Implies a Common Mechanism for Protein Misfolding Diseases," Nature, 416(6880):507-511 (2002).
Buchan, K.W. et al., "Characterization of three non-peptide endothelin receptor ligands using human cloned ETA and ETB receptors," Brit. J. Pharmacol., 112:1251-1257 (1994).
Buddi et al., "Evidence of oxidative stress in human corneal diseases," The Journal of Histochemistry and Cytochemistry: official journal of the Histochemistry Society, 50(3):341-351 (2002).
Bundgaard et al., "Glycolamide esters as biolabile prodrugs of carboxylic acid agents: Synthesis, Stability, bioconversion, and physicochemical properties," Journal of Pharmaceutical Sciences, 77(4):285-298 (1988).
Bundgaard, "Means to enhance penetration: (1) Prodrugs as a means to improve the delivery of peptide drugs," Advanced Drug Delivery Reviews, 8(1):1-38 (1992).
Burcham et al., "Aldehyde-Sequestering Drugs: Tools for Studying Protein Damage by Lipid Peroxidation Products," Toxicology, 181-182:229-236 (2002).
Burstein, "Preservative cytotoxic threshold for benzalkonium chloride and chlorhexidine digluconate in cat and rabbit corneas," Investigative Ophthalmology and Visual Science, 19(3):308-313 (1980).
Burstein, "The effects of topical drugs and preservatives on the tears and corneal epithelium in dry eye," Transactions of the Ophthalmological Societies of the United Kingdom, 104:402-409 (1985).
Canonica et al., "Recommendations for standardization of clinical trials with Allergen Specific Immunotherapy for respiratory allergy. A statement of a World Allergy Organization (WAO) taskforce," Allergy, 62(3):317-324 (2007).
Canonica et al., "Sub-lingual immunotherapy: World Allergy Organization Position Paper 2009," Allergy, 64(Suppl 91:1-59 (2009).
Casanaro et al., "A convenient solvent system for cellulose dissolution and derivatization: Mechanistic aspects of the acylation of the biopolymer in tetraallylammonium fluoride/dimethyl sulfoxide," Carbohydrate Polymers, 8(3):1395-1402 (2011).
Casanaro et al., "Efficacy of vigabatrin intervention in a mild phenotypic expression of succinic semialdehyde dehydrogenase deficiency," JIMD Rep. 2:119-23 (2011).
Cejkova et al., "The role of conjunctival epithelial cell xanthine oxidoreductase/xanthine oxidase in oxidative reactions on the ocular surface of dry eye patients with Sjögren's syndrome," Histol Histopathol 22(9):997-1003 (Sep. 2007).
Cesura et al., "Characterization of the binding of [3H]Ro 41-1049 to the active site of human monoamine oxidase-A," Mol. Pharmacol., 37:358-366 (1990).
Chapple et al., "Unfolding Retinal Dystrophies: a Role for Molecular Chaperones?" Trends Mol Med, 7(9):414-421 (2001).

(56) References Cited

OTHER PUBLICATIONS

Chen et al., "Methazolamide Calcium Phosphate Nanoparticles in an Ocular Delivery System," Pharm Soc Japan, 130(3):419-24 (2010).
Cheng et al., "A synthetic peptide derived from p34cdc2 is a specific and efficient substrate of src-family tyrosine kinases," J. Biol. Chem., 267:9248-9256 (1992).
Chiarpotto et al., "Role of 4-hydroxy-2,3-nonenal in the pathogenesis of fibrosis," Biofactors, 24(1-4):229-36 (2005).
Chicchi et al., "Alterations in receptor activation and divalent cation activation of agonist binding by deletion of intracellular domains of the glucagon receptor," J. Biol. Chem., 272:7765-7769 (1997).
Choi et al., "Expression of Lipid Peroxidation Markers in the Tear Film and Ocular Surface of Patients with Non-Sjogren Syndrome: Potential Biomarkers for Dry Eye Disease," Curr Eye Res, 41(9):1143-11 (2016).
Choi et al., "The human serotonin 5-HT2B receptor: pharmacological link between 5-HT2 and 5-HT1D receptors," FEBS Lett., 352:393-399 (1994).
Ciolino et al., "Effect of alcaftadine 0.25% on ocular itch associated with seasonal or perennial allergic conjunctivitis: a pooled analysis of two multicenter randomized clinical trials," Clin Ophthalmol, 9:765-72 (May 2015).
Clark et al., "Inhibition of dexamethasone-induced cytoskeletal changes in cultured human trabecular meshwork cells by tetrahydrocortisol," Invest. Ophtalmol. Vis. Sci., 37:805-813 (1996).
Clinical Trials Results for Outcome Measures of Ocular Itching and Ocular Tearing (1 page) (2016).
Clinical Trials Results of Treatment with Aldehyde Trapping Compound NS2 (1 page) (2015).
Clinical Trials Results of Treatment with NS2 Topical Formulation (1 page) (2015).
ClinicalTrials.gov identifier NCT02402309, "A Study of Topical NS2 Cream to Treat Ichthyosis in Sjogren-Larsson Syndrome (SLS)," https://clinicaltrials.gov/ct2/show/NCT02402309 (3 pages) (2015).
ClinicalTrials.gov identifier NCT02406209, "A Safety and Efficacy Study of NS2 in Patients with Anterior Uveitis," https://clinicaltrials.gov/ct2/show/NCT02406209 (4 pages) (2015).
ClinicalTrials.gov identifier NCT02578914, "A Safety and Activity Study of NS2 in Subjects with Allergic Conjunctivitis," https://clinicaltrials.gov/ct2/show/NCT02578914 (6 pages) (2015).
ClinicalTrials.gov identifier NCT03162783, "A Randomized, Double Masked, Clinical Study of Subjects with Dry Eye Syndrome," (7 pages) (2017).
Conover et al., "Thiazole Analogs of Pyridoxine," Journal of the American Chemical Society, 72(11):5221-5225 (1950).
Cooper et al., "Clinicopathologic study of dextran sulfate sodium experimental murine colitis," Lab Invest, 69(2):238-49 (Aug. 1993).
Couvineau et al., "Molecular identification and structural requirement of vasoactive intestinal peptide (VIP) receptors in the human colon adenocarcinoma cell line, HT-29," Biochem. J., 231:139-143 (1985).
Cullen et al, "Administration of the small molecule aldehyde trap NS2 in a hamster model of radiation-induced oral mucositis," ISOO 2015 Annual Meeting Abstract, Support Care Cancer, 23 (Suppl 1):S107 (Jun. 2015).
Cullen et al, "The small molecule aldehyde trap NS2 exhibits potent anti-inflammatory activity in three murine models of inflammation," AAAAI Annual Meeting Abstract, 1 page (Feb. 2015).
Davies, "Biopharmaceutical considerations in topical ocular drug delivery," Clin Exp Pharmacol Physiol, 27(7):558-62 (Jul. 2000).
De Jong, "Age-Related Macular Degeneration," N Engl J Med, 355(14):1474-1485 (2006).
Del Valle, "Cyclodextrins and their uses: a review," Process Biochemistry, 39(9):1033-1046 (2004).
Demir et al., "Oxidative stress of intracameral lidocaine and levobupivacaine on ocular tissues," Br J Ophthalmol, 94(8):1083-7 (Aug. 2010).
Demir et al., "The protective effect of alpha-lipoic acid against oxidative damage in rabbit conjunctiva and cornea exposed to ultraviolet radiation," Ophthalmologica, 219(1):49-53 (Jan.-Feb. 2005).
Dente et al., "Modified phage peptide libraries as a tool to study specificity of phosphorylation and recognition of tyrosine containing peptides," J. Mol. Biol., 269:694-703 (1997).
Devedjian et al., "Further characterization of human alpha 2-adrenoceptor subtypes: [3H]RX821002 binding and definition of additional selective drugs," Eur. J. Pharmacol., 252:43-49 (1994).
Devillier et al., "The allergen challenge chamber: a valuable tool for optimizing the clinical development of pollen immunotherapy," Allergy, 2011; 66(2):163-9.
Dolmotova et al, "Cardiomyocyte ATP release through pannexin 1 aids in early fibroblast activation," Am. J. Physiol Heart Circ Physiol 303(10):H1208-1218 (2012).
Dorje et al., "Antagonist binding profiles of five cloned human muscarinic receptor subtypes," J. Pharmacol. Exp. Ther., 256:727-733 (1991).
Dowling, "Neural and Photochemical Mechanisms of Visual Adaptation in the Rat," Journal of General Physiology, 46(6):1287-1291 (1963).
Drysdale et al., "Complex Promoter and Coding Region Beta 2-adrenergic Receptor Haplotypes Alter Receptor Expression and Predict in vivo Responsiveness," Proc Natl Acad Sci USA, 97(19):10483-10488 (2000).
Egger, et al., "Keratinocyte growth factor ameliorates dextran sodium sulfate colitis in mice," Dig Dis Sci, 44(4): 836-44 (Apr. 1999).
Ellis et al., "Multiple Doses of Trodusquemine Improve Glucose Tolerance in Type 2 Diabetic Subjects," 69th Scientific Sessions of the American Diabetes Association, Abstract No. 2071-PO (2009).
Ellman et al., "A new and rapid colorimetric determination of acetylcholinesterase activity," Biochem. Pharmacol., 7: 88-95 (1961).
Erdos et al, "Neutral endopeptidase 24.11 (enkephalinase) and related regulators of peptide hormones," FASEB J. 3:145 (1989).
Ermolieff et al., "Proteolytic activation of recombinant pro-memapsin 2 (pro-beta-secretase) studied with new fluorogenic substrates," Biochemistry, 39:12450-12456 (2000).
Escalera et al., "Succinic semialdehyde dehydrogenase deficiency: decrease in 4-OH-butyric acid levels with low doses of vigabatrin," An Pediatr (Barc). 72(2):128-32 (2010).
Esterbauer et al., "Chemistry and Biochemistry of 4-Hydroxynonenal, Malonaldehyde and Related Aldehydes," Free Radic Biol Med, 11:81-128 (1991).
European Supplementary Partial Search Report issued by the European Patent Office for European Patent Application No. 13865015.5 dated Mar. 31, 2016 (9 pages).
European Supplementary Partial Search Report issued by the European Patent Office for European Patent Application No. 14743711.5 dated Jul. 20, 2016 (14 pages).
Everest-Todd, "Topical Application of Cyclodextrin Ethers in the Control of Pain," Proceedings of the Eighth International Symposium on Cyclodextrins, pp. 495-498 (1998).
Farid et al., "Detection of corneal fibrosis by imaging second harmonic-generated signals in rabbit corneas treated with mitomycin C after excimer laser surface ablation," Invest Ophthalmol Vis Sci., 2008; 49(10):4377-83.
FDA, "BAM R59: Phosphate-Buffered Saline (PBS), pH 7.4," Jan. 2001, retrieved online at <http://www.fda.gov/Food/FoodScienceR.esearch/LaboratoxyMethods/ucm062268.htm> on Apr. 18, 2015 (1 page).
Feighner et al., "Receptor for motilin identified in the human gastrointestinal system," Science, 284:2184-2188 (1999).
Fernandes et al., "Characterization of angiotensin-converting enzymes 1 and 2 in the soleus and plantaris muscles of rats," Braz J Med Biol Res., 43:837-842 (2010).
Ferry et al., "Binding of prostaglandins to human PPAR?: Tool assessment and new natural ligands," Eur. J. Pharmacol., 417:77-89 (2001).

(56) References Cited

OTHER PUBLICATIONS

Feve et al., "Transcriptional down-regulation by insulin of the beta 3-adrenergic receptor expression in 3T3-F442A adipocytes: a mechanism for repressing the cAMP signaling pathway," Proc Natl Acad Sci USA. 91:5677 (1994).
Fiske et al., "The Colormetric Determination of Phosphorus," J. Biol. Chem., 66:375-400 (1925).
Fitzmaurice et al., "Aldehyde dehydrogenase inhibition as a pathogenic mechanism in Parkinson disease," Proc. Natl Acad Sci U.S.A, 110(2):636-641 (2013).
Ford et al., "Pharmacological pleiotropism of the human recombinant alpha1A-adrenoceptor: implications for alpha1-adrenoceptor classification," Brit. J. Pharmacol., 121:1127-1135 (1997).
Fowler et al., "Coloured Complexes of all-trans-retinal with Benzocaine and Other Local Anesthetics," J Photochem Photobiol B, 8(2):183-188 (1991).
Frantz et al., "The Activation State of p38 Mitogen-Activated Protein Kinase Determines the Efficiency of ATP Competition for Pyridinylimidazole Inhibitor Binding," Biochemistry, 37:13846-13853 (1998).
Fuchs et al., "Functional characterization of three mutations of the endothelin B receptor gene in patients with Hirschsprung's disease: evidence for selective loss of Gi coupling," Mol. Med., 7:115-124 (2001).
Fukunaga et al., "Single nucleotide polymorphism of human platelet-activating factor receptor impairs G-protein activation," J. Biol. Chem., 276:43025-43030 (2001).
Full 1H NMR assignment for RAL-NS2 in CDCIJ, submitted to Japanese Patent Office dated Mar. 1, 2012.
Ganapathy et al., "Molecular and ligand-binding characterization of the sigma-receptor in the Jurkat human T lymphocyte cell line," JPET, 289:251-260 (1999).
Gasper et al., "2-Hydroxypropyl-beta-cyclodextrin (HP?CD) reduces age-related lipofuscin accumulation through a cholesterol-associated pathway," Scientific Reports, 7(2197):1-7 (2017).
Gibson et al., "Stable isotope dilution analysis of 4-hydroxybutyric acid: an accurate method for quantification in physiological fluids and the prenatal diagnosis of 4-hydroxybutyric aciduria," Biomed Environ Mass Spectrom., 19(2):89-93 (1990).
Gibson et al., "Stable-isotope dilution analysis of D- and L-2-hydroxyglutaric acid: application to the detection and prenatal diagnosis of D- and L-2-hydroxyglutaric acidemias," Pediatr Res., 34(3):277-80 (1993).
Gibson et al., "The Aldehyde Trap NS2 Mitigates Dense Haze in a Rabbit Model of Photorefractive Keratectomy" ARVO Annual Meeting Abstract, 1 page (Jun. 2015).
Gibson et al., "The Aldehyde Trap NS2 Mitigates Dense Haze in a Rabbit Model of Photorefractive Keratectomy" Poster presented at ARVO Annual Meeting, 1 page (May 3-7, 2015).
Godard et al., "Sur les orthoamino formyl quinoleines, nouveaux synthons heterocycliques," J Heterocyclic Chem, 17(3):465-473 (1980).
Goldstein et al., "A Phase 2 Exploratory Study of a Novel Interleukin-1 Receptor Inhibitor (EBI-005) in the Treatment of Moderate-to-Severe Allergic Conjunctivitis," Eye Contact Lens, 41(3):145-55 (May 2015).
Good, "Measuring field loss in children administered vigabatrin: a problem in search of a solution," J AAPOS. 15(5):411-2 (2011).
Gopalakrishnan et al., "Stable expression, pharmacologic properties and regulation of the human neuronal nicotinic acetylcholine alpha 4 beta 2 receptor," J. Pharmacol. Exp. Ther., 276:289-297 (1996).
Gould et al., "[3H]nitrendipine-labeled calcium channels discriminate inorganic calcium agonists and antagonists," Proc. Natl. Acad. Sci. U.S.A., 79:3656-3660 (1982).
Grandy et al., "Cloning of the cDNA and gene for a human D2 dopamine receptor," Proc. Natl. Acad. Sci. U.S.A., 86:9762-9766 (1989).
Green et al., "Characterization of [(3)H]-CGP54626A binding to heterodimeric GABA(B) receptors stably expressed in mammalian cells," Brit. J. Pharmacol., 131:1766-1774 (2000).
Green et al., "Influence of Various Agents on Corneal Permeability," American Journal of Ophthalmology, 72(5):897-905 (1971).
Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 33(6):1796-1808 (1950).
Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 33(6):1796-1808 (1950) [Machine Translation].
Gromachevskaya et al., "4H-3,1-benzoxazines. 2. Synthesis of 2,4-substituted 1,2-dihydro-4H-3,1-benzoxazines," Chemistry of Heterocyclic Compounds, 24(6):692-697 (Jun. 1988).
Grotto et al., "Importance of the lipid peroxidation biomarkers and methodological aspects for malondialdehyde quantification," Quim Nova, 32(1):169-174 (2009).
Halilovic et al., "ADX-103, a Novel Small Molecule Aldehyde Sequestering Agent, Decreases Retinal Edema and Inflammation in a Rat Model of Diabetic Macular Edema," ARVO Annual Meeting Abstract, 2 pages (Jul. 2018).
Hampson et al., "Cannabidiol and (–)Delta9-tetrahydrocannabinol are neuroprotective antioxidants," Proc. Nat. Acad. Sci 95:8268-8273 (1998).
Hassan et al., "Oxidative stress in systemic lupus erythematosus and rheumatoid arthritis patients: relationship to disease manifestations and activity," International Journal of Rheumatic Diseases, 14(1):325-331 (2011).
Herbort et al., "Endotoxin-induced uveitis in the rat," Graefe's Arch Clin Exp Ophthalmol, 226:553-8 (1988).
Hessen et al., "Dry Eye: an Inflammatory Ocular Disease," J Ophthalmic Vis Res, 9(2):240-250 (2014).
Heuillet et al., "Characterization of a Human NK1 Tachykinin Receptor in the Astrocytoma Cell Line U 373 MG," J. Neurochem., 60:868-876 (1993).
Hogema et al., "Pharmacologic rescue of lethal seizures in mice deficient in succinate semialdehyde dehydrogenase," Nat Genet. 29:212-16 (2001).
Hom et al., "Allergic conjunctivitis and dry eye syndrome," Ann Allergy Asthma Immunol, 108(3):163-6 (Mar. 2012).
Hope et al., "Characterization of a human 5-hydroxytryptamine3 receptor type a (h5-HT3R-AS) subunit stably expressed in HEK 293 cells," Brit. J. Pharmacol., 118:1237-1245 (1996).
Hoyer et al., "Characterization of the 5-HT1B recognition site in rat brain: binding studies with (–)[125I]iodocyanopindolol," Eur. J. Pharmacol., 118:1-12 (1985).
Huang et al., "Characterization of Calcium Phosphate Nanoparticles Based on a PEGylated Chelator for Gene Delivery," ACS Appl Mater Interfaces, 9:10435?10445 (Mar. 2017).
Huang et al., "Identification of human Ether-à-go-go related gene modulators by three screening platforms in an academic drug-discovery setting," Assay Drug Dev Technol., 8(6):727-42 (2010).
Huang et al., "Novel peptide inhibitors of angiotensin-converting enzyme 2," J. Biol. Chem., 278:15532-15540 (2003).
Hubbard, "Geometrical Isomerization of Vitamin A, Retinene and Retinene Oxime," Journal of the American Chemical Society, 78(18):4662-4667 (1956).
Hugues et al., "Preparation of a pure monoiodo derivative of the bee venom neurotoxin apamin and its binding properties to rat brain synaptosomes," J. Biol. Chem., 257:2762-2769 (1982).
Hurd et al., "Reaction of Propiolactone with Aniline Derivatives," Journal of the American Chemical Society, 74(23):5889-5893 (1952).
Inoue et al., "Filter-binding assay procedure for thyroid hormone receptors," Anal Biochem. 134(1):176 (1983).
International Preliminary Report on Patentability issued by the European Patent Office as International Searching Authority for International Application PCT/US2006/020320 dated Nov. 30, 2007 (8 pages).
International Preliminary Report on Patentability issued by the Korean Intellectual Property Office as International Searching Authority for International Application No. PCT/US2013/076592 dated Jun. 23, 2015 (6 pages).

(56) References Cited

OTHER PUBLICATIONS

International Preliminary Report on Patentability issued by the Korean Intellectual Property Office as International Searching Authority for International Application No. PCT/US2014/012356 dated Jul. 28, 2015 (7 pages).
International Preliminary Report on Patentability issued by the United States Patent and Trademark Office as International Searching Authority for International Application No. PCT/US2014/012762 dated Jul. 28, 2015 (8 pages).
International Preliminary Report on Patentability issued in PCT/US2016/048054 dated Feb. 27, 2018 (5 pages).
International Preliminary Report on Patentability issued in PCT/US2016/048064 dated Feb. 27, 2018 (6 pages).
International Search Report and Written Opinion issued by the European Patent Office as International Searching Authority for International Patent Application No. PCT/US2019/044929 dated Nov. 20, 2019 (15 pages).
International Search Report and Written Opinion issued by the Korean Intellectual Property Office as International Searching Authority for International Application No. PCT/US2013/076592 dated Apr. 30, 2014 (10 pages).
International Search Report and Written Opinion issued by the Korean Intellectual Property Office as International Searching Authority for International Application No. PCT/US2014/012356 dated May 30, 2014 (11 pages).
International Search Report and Written Opinion issued by the United States Patent and Trademark Office as International Searching Authority for International Application No. PCT/US2010/059719 dated Feb. 8, 2011 (7 pages).
International Search Report and Written Opinion issued by the United States Patent and Trademark Office as International Searching Authority for International Application No. PCT/US2014/012762 dated Jul. 18, 2014 (11 pages).
International Search Report and Written Opinion issued by the United States Patent and Trademark Office as International Searching Authority for International Application No. PCT/US2017/047945 dated Oct. 20, 2017 (9 pages).
International Search Report and Written Opinion issued by the United States Patent and Trademark Office as International Searching Authority for International Patent Application No. PCT/US2017/020020 dated May 24, 2017 (12 pages).
International Search Report and Written Opinion issued by the United States Patent and Trademark Office as International Searching Authority for International Patent Application No. PCT/US2018/055310 dated Jan. 29, 2019 (9 pages).
International Search Report and Written Opinion issued by the United States Patent and Trademark Office as International Searching Authority for International Patent Application No. PCT/US2019/041942 dated Sep. 30, 2019 (18 pages).
International Search Report and Written Opinion issued by the United States Patent and Trademark Office as International Searching Authority for International Patent Application No. PCT/US2019/045206 dated Oct. 17, 2019 (13 pages).
International Search Report and Written Opinion issued by the United States Patent and Trademark Office as International Searching Authority for International Patent Application No. PCT/US2019/052961, dated Dec. 10, 2019 (11 pages).
International Search Report and Written Opinion issued by the United States Patent and Trademark Office as International Searching Authority for International Patent Application No. PCT/US2019/054263, dated Jan. 6, 2020 (13 pages).
International Search Report and Written Opinion issued by the United States Patent and Trademark Office as International Searching Authority for International Patent Application No. PCT/US2019/064669, dated Feb. 27, 2020 (12 pages).
International Search Report and Written Opinion issued by the United States Patent and Trademark Office as International Searching Authority for International Patent Application No. PCT/US2020/024022, dated Jun. 17, 2020 (11 pages).
International Search Report and Written Opinion issued by the United States Patent and Trademark Office as International Searching Authority for International Patent Application No. PCT/US2020/031138, dated Jul. 13, 2020 (7 pages).
International Search Report and Written Opinion issued by the United States Patent and Trademark Office as International Searching Authority for International Patent Application No. PCT/US2020/031219, dated Aug. 31, 2020 (14 pages).
International Search Report and Written Opinion issued by the United States Patent and Trademark Office as International Searching Authority for International Patent Application No. PCT/US2020/050565, dated Dec. 22, 2020 (9 pages).
International Search Report and Written Opinion issued in PCT/US2006/020320, dated Sep. 26, 2006 (10 pages).
International Search Report and Written Opinion issued in PCT/US2016/048054 dated Nov. 4, 2016 (7 pages).
International Search Report and Written Opinion issued in PCT/US2016/048064 dated Nov. 15, 2016 (8 pages).
Iriyama et al., "A2E, a pigment of the lipofuscin of retinal pigment epithelial cells, is an endogenous ligand for retinoic acid receptor," J Biol Chem., 283(18):11947-53 (2008) Epub Mar. 6, 2008.
Irons, "Fluvoxamine in the treatment of anxiety disorders," Neuropsychiatr Dis Treat, 1(4):289-99 (Dec. 2005).
Ishida et al., "Stabilization of calmodulin-dependent protein kinase II through the autoinhibitory domain," J. Biol. Chem., 270:2163-2170 (1995).
Ito et al., "A Medium-Term Rat Liver Bioassay for Rapid in vivo Detection of Carcinogenic Potential of Chemicals," Cancer Science, 94(1):3-8 (2003).
Itokawa et al., "Antiangiogenic effect by SU5416 is partly attributable to inhibition of Flt-1 receptor signaling," Mol. Cancer Ther., 1:295-302 (2002).
Jacobs et al., "Responses to ragweed pollen in a pollen challenge chamber versus seasonal exposure identify allergic rhinoconjunctivitis endotypes," J. Allergy Clin. Immunol., 2012; 130(1):122-7.
Jafari et al., "Evaluation of plasma, erythrocytes, and bronchoalveolar lavage fluid antioxidant defense system in sulfur mustard-injured patients," Clin Toxicol (Phila)., 48(3):184-92 (2010).
Janowski et al., "Structural requirements of ligands for the oxysterol liver X receptors LXRalpha and LXRbeta," Proc. Natl. Acad. Sci. USA, 96:266-271 (1999).
Jarrett et al., "Mitochondrial DNA damage and impaired base excision repair during epileptogenesis," Neurobiology of Disease, 30(1):130-138 (2008).
Jellinger et al., "American Association of Clinical Endocrinologists and American College of Endocrinology Guidelines for Management of Dyslipemia and Prevention of Cardiovascular Disease," Endocr Pract, 23(Suppl 2):1-87 (Apr. 2017).
Ji et al.,"Exploration of diverse hinge-binding scaffolds for selective Aurora kinase inhibitors," Bioorg. & Med. Chem. Let. 22:4528 (2012).
Johannsdottir et al., "Development of a Cyclodextrin-Based Aqueous Cyclosporin a Eye Drop Formulations," International Journal of Pharmaceutics, 493(1-2):86-95 (2015).
Johnson et al., "2-Hydroxypropy1-β-Cyclodextrin Removes All-Trans Retinol from Frog Rod Photoreceptors in a Concentration-Dependent Manner," Journal of Ocular Pharmacology and Therapeutics, 26(3):245-248 (2010).
Joseph et al., "Binding of (−)[3H]-CGP12177 at two sites in recombinant human beta 1-adrenoceptors and interaction with beta-blockers," Naun.-Sch. Arch. Pharm., 369:525-532 (2004).
Kam et al., "Topical Cyclodextrin Reduces Amyloid Beta and Inflammation Improving Retinal Function in Ageing Mice," Experimental Eye Research, 135:59-66 (2015).
Kamino et al., "Deficiency in mitochondrial aldehyde dehydrogenase increases the risk for late-onset Alzheimer's disease in the Japanese population," Biochemical and Biophysical Research Communications, 273(1):192-196 (2000).
Karahashi et al., "Changes of caspase activities involved in apoptosis of a macrophage-like cell line J774.1/JA-4 treated with lipopolysaccharide (LPS) and cycloheximide," Biol. Pharm. Bull., 23:140-144 (2000).

(56) References Cited

OTHER PUBLICATIONS

Karan et al., Lipofuscin Accumulation, Abnormal Electrophysiology, and Photoreceptor Degeneration in Mutant ELOVL4 Transgenic Mice: A Model for Macular Degeneration, Proc Natl Acad Sci USA, 102(11):4164-4169 (2005).

Katugampola et al., "[(125)I]-(Pyr(1))Apelin-13 is a novel radioligand for localizing the APJ orphan receptor in human and rat tissues with evidence for a vasoconstrictor role in man," Brit. J. Pharmacol., 132:1255-1260 (2001).

Keister et al., "Inflammatory Bowel Disease and Irritable Bowel Syndrome Similarities and Differences," Crohn's & Colitis Foundation of America. 2014; 12 pages.

Kenney et al., "The Cascade Hypothesis of Keratoconus," Contact Lens & Ant Eye, 26:139-146 (2003).

Keri, "Rosacea," Merck Manual, Professional Version, https://www.merckmanuals.com/professional/dermatologic-disorders/acne-and-related-disorders/rosacea, 7 pages (2017).

Knapp et al., "Intraocular Availability of Topically Applied Mycophenolate Mofetil in Rabbits," J. Ocul. Pharmacol. Ther., 19(2):181-192 (2003).

Landor et al., "Allenes. Part 49, 4-Amino-2-(1-hydroxyalkyl)quinolones from Phenylhydroxylamine and Allenic Nitrites," J Chem Soc Perkin Trans 1, pp. 251-254 (1989).

Langin et al., "[13H]RX821002: a new tool for the identification of alpha 2A-adrenoceptors," Eur. J. Pharmacol., 167: 95-104 (1989).

Lankin et al., "Role of Oxidative Stress in the Genesis of Atherosclerosis and Diabetes Mellitus: A Personal Look Back on 50 Years of Research," Curr. Aging Sci. 10:18 (2017).

Le et al., "Ligand binding and functional properties of human angiotensin AT1 receptors in transiently and stably expressed CHO-K1 cells," Eur. J. Pharmacol., 513:35-45 (2005).

Lee et al., "Human recombinant soluble guanylyl cyclase: expression, purification, and regulation," Proc. Natl. Acad. Sci. USA, 97(20):10763-10768 (2000).

Lee et al., "The human brain cholecystokinin-B/gastrin receptor. Cloning and characterization," J. Biol. Chem., 268 : 8164-8169 (1993).

Leibundgut et al., "Oxidation-specific epitopes and immunological responses: Translational biotheranostic implications for atherosclerosis," Current Opinion in Pharmacology, 13(2):168-179 (2013).

Leonardi et al., "Correlation Between Conjunctival Provocation Test (CPT) and Systemic Leonardi Tests in Allergic Conjunctivitis," Eye, 4:760-764 (1990).

Leonardi, "Allergy and allergic mediators in tears," Exp. Eye Res., 2013; 117:106-17.

Leurs et al., "Pharmacological characterization of the human histamine H2 receptor stably expressed in Chinese hamster ovary cells," Brit. J. Pharmacol., 112: 847-854 (1994).

Levin et al., "The myocardium-protective Gly-49 variant of the beta 1-adrenergic receptor exhibits constitutive activity and increased desensitization and down-regulation," J. Biol.Chem., 277:30429-30435 (2002).

Lewin et al., "meta- and para-isothiocyanato-t-butylbicycloorthobenzoate: irreversible ligands of the gamma-aminobutyric acid-regulated chloride ionophore," Mol. Pharmacol., 35:189-194 (1989).

Li et al., "Effect of Vitamin a Supplementation on Rhodopsin Mutants Threonine-17-> Methionine and Proline-347-> Serine in Transgenic Mice and in Cell Cultures," Proc Natl Acad Sci USA, 95(20):11933-11938 (1998).

Liang et al., "Ocular safety of cationic emulsion of cyclosporine in an in vitro corneal wound-healing model and an acute in vivo rabbit model," Mol Vis, 18:2195-204 (2012).

Liu et al., "Comparison of human, mouse, rat, and guinea pig histamine H4 receptors reveals substantial pharmacological species variation," J. Pharmacol. Exp. Ther., 299:121-130 (2001).

Loftsson et al., "Cyclodextrin Microparticles for Drug Delivery to the Posterior Segment of the Eye: Aqueous Dexamethasone Eye Drops," Journal of Pharmacy and Pharmacology, 59(5):629-635 (2007).

Loftsson et al., "Cyclodextrins in Eye Drop Formulations: Enhanced Topical Delivery of Corticosteroids to the Eye," Acta Ophthalmologica Scandinavica, 80(2):144-150 (2002).

Lopachin et al., "Molecular mechanisms of aldehyde toxicity: a chemical perspective," Chem Res Toxicol, 27(7):1081-91 (Jul. 2014).

Lovenberg et al., "Cloning and functional expression of the human histamine H3 receptor," Mol. Pharmacol., 55:1101-1107 (1999).

Lukas, R.J., "Characterization of curaremimetic neurotoxin binding sites on membrane fractions derived from the human medulloblastoma clonal line, TE671," J. Neurochem., 46:1936-1941 (1986).

Luthin et al., "Characterization of two affinity states of adenosine A2a receptors with a new radioligand, 2-[2-(4-amino-3-[125I]iodophenyl)ethylamino]adenosine," Mol. Pharmacol., 47:307-313 (1995).

MacDonald et al., "ADX-102, a novel aldehyde trap, reduces nociceptive behavior in mouse models of carrageenan and CFA induced pain," Int'l Conference on Pain Research & Management Abstract, J Pain Relief, 5 (5 Suppl):50 (Oct. 2016).

MacDonald et al., "Inhibition of fibroblast activation to the myofibroblast phenotype in neonatal rat cardiac fibroblasts using a small molecule aldehyde trap," ASCB Annual Meeting Abstract, p. 2 (Dec. 2016).

MacDonald et al., "Molecular characterization of the melanin-concentrating hormone/receptor complex: identification of critical residues involved in binding and activation," Mol. Pharmacol., 58:217-225 (2000).

MacDonald et al., "Novel Small Molecule Aldehyde Sequestering Agents Demonstrate Broad Therapeutic Potential for Ocular Inflammation," ARVO Annual Meeting Abstract, 2 pages (Jul. 2018).

MacDonald et al., "The novel aldehyde trap, ADX-102, reduces inflammation-mediated lung infilrate in a mouse model of LPS-induced acute lung injury," 13th World Congress on Inflammation Abstract, p. 192 (Jul. 2017).

MacKenzie et al., "Characterization of the human dopamine D3 receptor expressed in transfected cell lines," Eur. J. Pharmacol., 266:79-85 (1994).

Maeda et al., "Involvement of All-trans-retinal in Acute Light-induced Retinopathy of Mice," J Biol Chem, 284(22):15173-83 (May 2009).

Maeda et al., "Primary amines protect against retinal degeneration in mouse models of retinopathies," Nat Chem Biol, 8(2):170-178 (Dec. 2011).

Maguire et al., "Orphan-receptor ligand human urotensin II: receptor localization in human tissues and comparison of vasoconstrictor responses with endothelin-1," Brit. J. Pharmacol., 131:441-446 (2000).

Mandell et al., "The Aldehyde Trap NS2 Reduces Ocular Inflammation in an Endotoxin-Induced Model in Rats," Investigative ophthalmology & visual science. 2015; 56(7):3095.

Mantey et al., "Discovery of a high affinity radioligand for the human orphan receptor, bombesin receptor subtype 3, which demonstrates that it has a unique pharmacology compared with other mammalian bombesin receptors," J. Biol. Chem., 272:26062-26071 (1997).

Marnett, "Oxy radicals, lipid peroxidation and DNA damage," Toxicology, 181-182:219-222 (2002).

Martin et al., "Molecular cloning and functional characterization of murine cysteinyl-leukotriene 1 (CysLT(1)) receptors.," Biochem. Pharmacol., 62:1193-1200 (2001).

Matern et al.,"Seizures in a boy with succinic semialdehyde dehydrogenase deficiency treated with vigabatrin (gamma-vinyl-GABA)," J Inherit Metab Dis., 19(3):313-8 (1996).

Maurice et al., "Advances in targeting cyclic nucleotide phosphodiesterases," Nat Rev Drug Discov., 13:290-314 (2014).

McCord et al., "Superoxide dismutase. An enzymic function for erythrocuprein (hemocuprein).," J. Biol. Chem., 244: 6049-6055 (1969).

McGinnity et al., "Evaluation of fresh and cryopreserved hepatocytes as in vitro drug metabolism tools for the prediction of metabolic clearance." Drug Metab. Dispos., 32(11):1247-1253 (2004).

McLaurin et al., "Phase 3 Randomized Double-Masked Study of Efficacy and Safety of Once-Daily 0.77% Olopatadine Hydrochlo-

(56) References Cited

OTHER PUBLICATIONS ride Ophthalmic Solution in Subjects with Allergic Conjunctivitis Using the Conjunctival Allergen Challenge Model," Clinical Science, 34(10):1245-1251 (2015).
Medline Plus. Macular Degeneration—age-related. (6 pages) (2013).
Meijer et al., "Biochemical and cellular effects of roscovitine, a potent and selective inhibitor of the cyclin-dependent kinases cdc2, cdk2 and cdk5," Eur. J. Biochem., 243:527-536 (1997).
Meng et al., "Cloning and pharmacological characterization of a rat kappa opioid receptor," Proc. Natl. Acad. Sci. U.S.A., 90:9954-9958 (1993).
Mialet et al., "Isolation of the serotoninergic 5-HT4(e) receptor from human heart and comparative analysis of its pharmacological profile in C6-glial and CHO cell lines," Brit. J. Pharmacol., 129:771-781 (2000).
Miceli et al., "Efficacy of keratinocyte growth factor-2 in dextran sulfate sodium-induced murine colitis," J Pharmacol Exp Ther, 290(1):464-71 (Jul. 1999).
Mishra et al., "Recent Patents and Emerging Therapeutics in the Treatment of Allergic Conjunctivitis," Recent Pat. Inflamm. Allergy Drug Discov.; 2011; 5(1):26-36.
Mittl et al., "Structure of recombinant human CPP32 in complex with the tetrapeptide acetyl-Asp-Val-Ala-Asp fluoromethyl ketone," J. Biol. Chem., 272:6539-6547 (1997).
Monaghan et el., "The distribution of [3H]kainic acid binding sites in rat CNS as determined by autoradiography," Brain Res., 252:91-100 (1982).
Monsma et al., "Cloning and expression of a novel serotonin receptor with high affinity for tricyclic psychotropic drugs," Mol. Pharmacol., 43:320-327 (1993).
Mulheron et al., "Human 5-HT1A receptor expressed in insect cells activates endogenous G(o)-like G protein(s)," J. Biol. Chem., 269:12954-12962 (1994).
Muller-Enoch et al., "[6.7-Dihydroxycoumarin (Aesculetin) as a substrate for catechol-o-methyltransferase (author's transl)]," Z. Naturforsch., 31:280-284 (1976).
Munro et al., "Molecular characterization of a peripheral receptor for cannabinoids," Nature, 365:61-65 (1993).
Murphy et al., "Characterization of quisqualate recognition sites in rat brain tissue using DL-[3H]alpha-amino-3-hydroxy-5-methylisoxazole-4-propionic acid (AMPA) and a filtration assay," Neurochem. Res., 12:775-781 (1987).
Na et al., "Molecular profiling of a 6-hydroxydopamine model of Parkinson's disease," Neurochem Res, 35(5):761-72 (May 2010).
Nagai et al., Improved corneal toxicity and permeability of tranilast by the preparation of ophthalmic formulations containing its nanoparticles, J Oleo Sci, 63(2):177-86 (2014).
Nagase et al., "Design and characterization of a fluorogenic substrate selectively hydrolyzed by stromelysin 1 (matrix metalloproteinase-3)," J. Biol. Chem., 269:20952-20957 (1994).
Nakamura et al., "Involvement of Oxidative Stress on Corneal Epithelial Alterations in a Blink-Suppressed Dry Eye," Investigative Ophthalmology and Visual Science, 48(4):1552-1558 (2007).
Negre-Salvayre et al., "Advanced Lipid Peroxidation End Products in Oxidative Damage to Proteins. Potential Role in Diseases and Therapeutic Prospects for the Inhibitors," Br J Pharmacol, 153(1):6-20 (2008).
Nema et al., "Excipients and Their Use in injectable Products," PDA J Pharm Sci Technol, 51(4):166-171 (1997).
Nerurkar et al., "Beta-Arylglutaconic Acids. II. Imides of Certain Beta-Arylglutaconic and Glutaric Acids," J Org Chem, 24(12):2055-2056 (1959).
Niwa et al., "Protein oxidative damage in the stratum corneum: Evidence for a link between environmental oxidants and the changing prevalence and nature of atopic dermatitis in Japan," Br J Dermatol., 149:248 (2003).
Nociari et al., "Beta cyclodextrins bind, stabilize, and remove lipofuscin bisretinoids from retinal pigment epithelium," Proc Natl Acad Sci U.S.A E1402-E1408 (2014).

Noorwez et al., "Pharmacological Chaperone-mediated in Vivo Folding and Stablization of the P23H-Opsin Mutant Associated with Autosomal Dominant Retinitis Pigmentosa," J Biol Chem, 278:14442-14450 (2003).
O'Brien et al., "Aldehyde Sources, Metabolism, Molecular Toxicity Mechanisms, and Possible Effects on Human Health," Crit Rev Toxicol, 35:609-662 (2005).
O'Regan et al., "Filaggrin in atopic dermatitis," J Allergy Clin Immunol. 2008; 122(4):689-693 (republished as O'Regan et al., J Allergy Clin Immunol. 2009; 124(3 Suppl 2):R2-6).
Obourn et al., "Hormone- and DNA-binding mechanisms of the recombinant human estrogen receptor," Biochemistry 32(24):6229 (1993).
Okayasu, et al., "A novel method in the induction of reliable experimental acute and chronic ulcerative colitis in mice," Gastroenterology, 98(3):694-702 (Mar. 1990).
Organisciak et al., "Susceptibility to Retinal Light Damage in Transgenic Rats with Rhodopsin Mutations," Invest Ophthalmol Vis Sci, 44(2):486-492 (2003).
Pacholczyk et al., "Expression cloning of a cocaine- and antidepressant-sensitive human noradrenaline transporter," Nature, 350:350-354 (1991).
Pal et al., "Sulfur mustard analog induces oxidative stress and activates signaling cascades in the skin of SKH-1 hairless mice," Free Radic Biol Med., 47(11):1640-51 (2009).
Palchaudhuri et al., "Corticotropin-releasing factor receptor type 1 from Tupaia belangeri—cloning, functional expression and tissue distribution," Eur. J. Biochem., 258:78-84 (1998).
Parish et al., "Isolation and One-Step Preparation of A2E and iso-A2E, Fluorophores from Human Retinal Pigment Epithelium," Proc Natl Acad Sci USA, 95(25):14609-14613 (1998).
Park et al., "Homogeneous proximity tyrosine kinase assays: scintillation proximity assay versus homogeneous time-resolved fluorescence," Anal. Biochem., 269:94-104 (1999).
Park et al., "Modulation of acute inflammation and keratocyte death by suturing, blood, and amniotic membrane in PRK," Invest Ophthalmol Vis Sci. 2000; 41(10):2906-14.
Parracho et al., "Differences between the gut microflora of children with autistic spectrum disorders and that of healthy children," Journal of Medical Microbiology, 54:987-991 (2005).
Patel C.Y., "Subtype selectivity of peptide analogs for all five cloned human somatostatin receptors (hsstr 1-5)," Endocrinology, 135:2814-2817 (1994).
Pearl et al., "Inherited disorders of gamma-aminobutyric acid metabolism and advances in ALDH5A1 mutation identification," Dev Med Child Neurol., 57(7):611-617 (2015).
Pellock, "Balancing clinical benefits of vigabatrin with its associated risk of vision loss," Acta Neurologica. Scandinavica. Supplementum., 124(s192):83-91 (2011).
Peralta et al., "Distinct primary structures, ligand-binding properties and tissue-specific expression of four human muscarinic acetylcholine receptors," EMBO. J., 6:3923-3929 (1987).
Petroski et al., "Selective labeling of embryonic neurons cultured on astrocyte monolayers with 5(6)-carboxyfluorescein diacetate (CFDA)," Journal of Neuroscience Methods, 52(1):23-32 (1994).
Pfaar et al., "Perspectives in allergen immunotherapy: 2017 and beyond," Allergy, 2018; 73(Suppl 104):5-23.
Pickering, D.S., "Pharmacological characterization of melatonin binding sites in Syrian hamster hypothalamus," Eur. J. Pharmacol., 175:71-77 (1990).
Pontikis et al., "Cyclodextrin alleviates neuronal storage of cholesterol in Niemann-Pick C disease without evidence of detectable blood-brain barrier permeability," Journal of Inherited Metabolic Disease, 36(3):491-498 (2013).
Pozzi et al., "Modification of Collagen IV by Glucose or Methylglyoxal Alters Distinct Mesangial Cell Function," Journal of the American Society of Nephrology, 20:2119-2125 (2009).
Pred Forte Prescribing Information, Allergan, 5 pages (2017).
Pristupa et al., "Pharmacological heterogeneity of the cloned and native human dopamine transporter: disassociation of [3H]WIN 35,428 and [3H]GBR 12,935 binding.," Mol. Pharmacol., 45:125-135 (1994).

(56) References Cited

OTHER PUBLICATIONS

Pruneau et al., "LF 16.0335, a novel potent and selective nonpeptide antagonist of the human bradykinin B2 receptor," Brit. J. Pharmacol., 125:365-372 (1998).
Pubchem, 1824609-67-7, SID 333824451, Apr. 24, 2017 (6 pages).
Pubchem, SCHEMBL16316728, CID 117758222, Feb. 23, 2016, modified Sep. 30, 2017 (13 pages).
Pufahl et al., "Development of a fluorescence-based enzyme assay of human 5-lipoxygenase," Anal. Biochem., 364:204-212 (2007).
Quinlan et al., "4-Hydroxy-2-Nonenal Levels Increase in the Plasma of Patients with Adult Respiratory Distress Syndrome as Linoleic Acid Appears to Fall," Free Radic Res. 1994; 21(2):95-106.
Radu et al., "Isotretinoin treatment inhibits lipofuscin accumulation in a mouse model of recessive Stargardt's macular degeneration," Novartis Foundation Symposium, 255(51-63):177-178 (2004).
Radu et al., "Treatment with Isotretinoin Inhibits Lipofuscin Accumulation in a Mouse Model of Recessive Stargardt's Macular Degeneration," Proc Natl Acad Sci USA, 100(8):4742-4747(2003).
Rajewski et al., "Pharmaceutical applications of cyclodextrins. 2. In vivo drug delivery," J Pharm Sci, 85(11):1142-69 (Nov. 1996).
Rapp et al., "The Effects of Local Anaesthetics on Retinal Function," Vision Res, 22(9):1097-1103 (1982).
Rauli et al., "Validation of Malondialdehyde and 4-Hydroxy-2-trans-Nonenal Measurement in Plasma by NICI-GC-MS1," J Biochem, 123:918-923 (1998).
Reed, "Lipid peroxidation and neurodegenerative disease," Free Radical Biology and Medicine, 51(7):1302-1319 (2011).
Rees et al., "Cloning and characterisation of the human 5-HT5A serotonin receptor," FEBS Lett., 355:242-246 (1994).
Restasis® Prescribing Information, Allergan, copyright 2016, revised 2017 (15 pages).
Reynolds et al., "(−)-[3H] desmethoxyverapamil labels multiple calcium channel modulator receptors in brain and skeletal muscle membranes: differentiation by temperature and dihydropyridines," J. Pharmacol. Exp. Ther., 237: 731-738 (1986).
Ricca et al., "Amphetamine derivatives and obesity," Appetite, 52(2):405-9 (Apr. 2009).
Rinaldi-Carmona et al., "Characterization of two cloned human CB1 cannabinoid receptor isoforms," J. Pharmacol. Exp. Ther., 278:871-878 (1996).
Rivkees et al., "Identification of domains of the human A1 adenosine receptor that are important for binding receptor subtype-selective ligands using chimeric A1/A2a adenosine receptors," J. Biol. Chem., 270:20485-20490 (1995).
Rizzo et al., "Aldehyde Trapping Agent NS2 Blocks Formation of Fatty Aldehyde Adducts with Phosphatidylethanolamine and Suggests Potential Therapeutic Approach for Sjogren-Larsson Syndrome," Mol Genet and Metab, 114(3):362A (Mar. 2015) [Abstract Only].
Rizzo et al., "Endogenous antioxidants and radical scavengers," Advances in Experimental Medicine and Biology, 698:52-6 (2010).
Rizzo et al., "Ichthyosis in Sjogren-Larsson syndrome reflects defective barrier function due to abnormal lamellar body structure and secretion," Arch Dermatol Res, 302(6):443-451 (2010).
Rizzo et al., "Sjogren-Larsson syndrome: molecular genetics and biochemical pathogenesis of fatty aldehyde dehydrogenase deficiency," Mol Genet Metab. 90(1):1-9 (2007).
Rizzo, Fatty aldehyde and fatty alcohol metabolism: review and importance for epidermal structure and function, Biochim Biophys Acta, 1841(3):377-89 (Mar. 2014).
Rizzo, "The role of fatty aldehyde dehydrogenase in epidermal structure and function" Dermato-Endocrinol, 3(2):91-99 (2011).
Roat, "Allergic Conjunctivitis," Merck Manual Professional Version, 3 pages (2016), Available at: https://www.merckmanuals.com/professional/eye-disorders/conjunctival-and-scleral-disorders/allergic-conjunctivitis.
Roat, "Keratoconjunctivitis Sicca," Merck Manual Professional Version, 5 pages (2016), Available at: https://www.merckmanuals.com/professional/eye-disorders/corneal-disorders/keratoconjunctivitis-sicca.
Roat, "Ocular Mucous Membrane Pemphigoid," Merck Manual Professional Version, 3 pages (2016), Available at: https://www.merckmanuals.com/professional/eye-disorders/conjunctival-and-scleral-disorders/ocular-mucous-membrane-pemphigoid.
Roat, "Scleritis," Merck Manual Professional Version, 3 pages (2016), Available at: https://www.merckmanuals.com/professional/eye-disorders/conjunctival-and-scleral-disorders/scleritis.
Rohrer et al., "Cloning and characterization of a fourth human somatostatin receptor," Proc. Natl. Acad. Sci. U.S.A. , 90:4196-4200 (1993).
Rønborg et al., "Exposure chamber for allergen challenge. The development and validation of a new concept," Allergy, 1996; 51(2):82-8.
Sahi et al., "Hepatocytes as a tool in drug metabolism, transport and safety evaluations in drug discovery." Current Drug Discov. Technol., 7(3):188-198 (2010).
Salvatore et al., "Molecular cloning and characterization of the human A3 adenosine receptor," Proc. Natl. Acad. Sci. U.S.A., 90:10365-10369 (1993).
Samsonov et al., "Impact of Atherosclerosis- and Diabetes-Related Dicarbonyls on Vascular Endothelial Permeability: A Comparative Assessment," Oxid. Med. Cell Longev. Article 1625130 (2017).
Sanchez et al., "Allergic Conjunctivitis," J Investig Allergol Clin Immunol, 21(2):1-19 (2011).
Sandikci et al., "Lipid Peroxidation and Antioxidant Defence System in Patients with Active or Inactive Behcet's Disease," Acta Derm Venereol, 83:342-346 (2003).
Sarafian et al., "Synergistic cytotoxicity of Delta(9)-tetrahydrocannabinol and butylated hydroxyanisole," Toxicology Letters, 133(2-3):171-179 (2002).
Sarup et al., "Resolution of high and low affinity progesterone receptors from human breast carcinoma T47D cells," J. Biol. Chem., 263:5624-5633 (1988).
Sasaki et al., "Retinal drug delivery using eyedrop preparations of poly-L-lysine-modified liposomes," Eur J Pharm Biopharm, 83(3):364-9 (2013).
Satici et al., "Malondialdehyde and antioxidant enzyme levels in the aqueous humor of rabbits in endotoxin-induced uveitis," Eur J Ophthalmol, 13(9-10):779-83 (Nov.-Dec. 2003).
Sayed et al., "Metabolic Activation of R,S-1-(Tetrahydro-2-turanyl)-5-fluorouracil (Ftorafur) to 5-fluorouracil by Soluble Enzymes," Cancer Research, 43:4039-4044 (1983).
Schaumberg et al., "Epidemiology of dry eye syndrome," Lacrimal Gland, Tear Film, and Dry Eye Syndromes 3, Kluwer Academic/Plenum Publishers, pp. 989-998 (2002).
Schaumberg et al., "Prevalence of Dry Eye Disease among US Men: Estimates from the Physicians' Health Studies," Arch Ophthalmol, 127(6):763-768 (Jun. 2009).
Schaumberg et al., "Prevalence of Dry Eye Syndrome Among US Women," Am J Ophthalmol, 136(2):318-326 (Aug. 2003).
Schioth et al., "Characterization of the binding of MSH-B, HB-228, GHRP-6 and 153N-6 to the human melanocortin receptor subtypes," Neuropeptides, 31:565-571 (1997).
Schramm et al., "The Cross-linked Biopolymer Hyaluronic Acid as an Artificial Vitreous Substitute," Invest Ophthalmol Vis Sci, 53(2):613-621 (Feb. 2012).
Schwinn et al., "Molecular cloning and expression of the cDNA for a novel alpha 1-adrenergic receptor subtype," J. Biol. Chem., 265:8183-8189 (1990).
Sciuto et al., "Therapeutic Treatments of Phosgene-Induced Lung Injury," Inhal Toxicol, 16(8):565-580 (2004).
Search Report and Written Opinion issued by the Intellectual Property Office of Singapore for Singapore Patent Application No. 11201504859Y dated Aug. 1, 2016 (12 pages).
Search Report and Written Opinion issued by the Intellectual Property Office of Singapore for Singapore Patent Application No. 11201505587Y dated Jul. 12, 2016 (12 pages).
Search Report and Written Opinion issued by the Intellectual Property Office of Singapore for Singapore Patent Application No. 11201505599Y dated Sep. 26, 2016 (11 pages).
Serbecic et al., "Anti-oxidative vitamins prevent lipid-peroxidation and apoptosis in corneal endothelial cells," Cell Tissue Res, 320(3):465-75 (Jun. 2005).

(56) References Cited

OTHER PUBLICATIONS

Shank et al., "Ion and temperature effects on the binding of gamma-aminobutyrate to its receptors and the high-affinity transport system," J. Neurochem., 54:2007-2015 (1990).
Shen et al., "Molecular cloning and expression of a 5-hydroxytryptamine7 serotonin receptor subtype," J. Biol. Chem., 268:18200-18204 (1993).
Sheppard et al., "A Randomized, Comparator-Controlled Phase 2 Clinical Trial of ADX-102 Ophthalmic Solution in Noninfectious Anterior Uveitis," ARVO Annual Meeting Abstract, Invest Ophth Vis Sci. 2017; 58(8):1231.
Sheppard et al., Targeting Anterior Uveitis: A Focus on Iontophoresis and Other Advanced Technologies, Sep. 1, 2018 [Retrieved Nov. 11, 2019] Retrieved from Internet URL: https://www.nyee.edu/files/NYEE/Health%20Professionals/Continuing%20Medical%20Education/Enduring%20CME%20Activities/158 _ supplement. smaU_ v 1 _FINAL %20082818.pdf (8 pages).
Sherman et al., "Cellular Defenses Against Unfolded Proteins: A Cell Biologist Thinks about Neurodegenerative Diseases," Neuron, 29(1):15-32 (2001).
Shipp et al., "Common acute lymphoblastic leukemia antigen (CALLA) is active neutral endopeptidase 24.11 ("enkephalinase"): direct evidence by cDNA transfection analysis," Proc Natl Acad Sci USA. 86:297 (1989).
Shoemaker et al., "[3H]diltiazem binding to calcium channel antagonists recognition sites in rat cerebral cortex," Eur. J. Pharmacol., 111:273-277 (1985).
Siegrist et al., "Radioreceptor assay for alpha-MSH using mouse B16 melanoma cells+.," J. Recep. Res., 8:323-343 (1988).
Sieving et al., "Inhibition of the Visual Cycle in vivo by 13-cis Retinoic Acid Protects from Light Damage and Provides a Mechanism for Night Blindness in Isotretinoin Therapy," Proc Natl Acad Sci USA, 98(4):1835-1840 (2001).
Sills et al., "[3H]CGP 39653: a new N-methyl-D-aspartate antagonist radioligand with low nanomolar affinity in rat brain," Eur. J. Pharmacol., 192:19-24 (1991).
Simonin et al., "The human delta-opioid receptor: genomic organization, cDNA cloning, functional expression, and distribution in human brain," Mol. Pharmacol., 46:1015-1021 (1994).
Singh et al., "The epidemiology of ocular and nasal allergy in the United States, 1988-1994," J. Allergy Clin. Immunol., 2010; 126(4):778-783.
Smit et al., "Regulation of the human histamine H1 receptor stably expressed in Chinese hamster ovary cells," Brit. J. Pharmacol., 117:1071-1080 (1996).
Smith et al., "Basic pathogenic mechanisms operating in experimental models of acute anterior uveitis," Immunol Cell Biol, 76:497-512 (1998).
Smith et al., "Oxidative stress and dopamine depletion in an intrastriatal 6-hydroxydopamine model of Parkinson's disease," Neuroscience. 144(3):1057-1066 (Feb. 2007).
Snead et al., "Gamma-hydroxybutyric acid," New England Journal of Medicine, 352(26):2721-2732 (2005).
Snell et al., "Novel structure having antagonist actions at both the glycine site of the N-Methyl-D-Aspartate receptor and neuronal voltage-sensitive sodium channels. Biochemical, electrophysiological, and behavioral characterization," J Pharmacol Exp Ther, 292(1):215-227 (2000).
Spadea et al., "Corneal wound healing after laser vision correction," Br J Ophthalmol. 2016; 100:28-33.
Spagnol et al., "Efficient synthesis of tricyclic benzobisoxazines by silica gel catalysis," J Org Chem, 2;72(5):1867-1869 (Mar. 2007).
Sparrow et al. "Phospholipid meets all-trans-retinal: the making of RPE bisretmoids," Journal of Lipid Research, 51: 247-261 (2010).
Speth et al., "Benzodiazepine receptors: temperature dependence of [3H]flunitrazepam binding," Life Sci., 24:351-358 (1979).
Stefansson, et al., "Cyclodextrins in Eye Drop Formulations," Journal of Inclusion Phenomena. 2002; 44:23-27; Abstract only, printed from https://insights.ovid.com/jinpmr/200244010/00984572-200244010-00006#, 2 pages.
Stehle et al., "Molecular cloning and expression of the cDNA for a novel A2-adenosine receptor subtype," Mol. Endocrinol., 6:384-393 (1992).
Stevenson et al., "Dry eye disease: an immune-mediated ocular surface disorder," Arch Ophthalmol. 2012; 130(1): 90-100.
Struys et al., "Determination of the GABA analogue succinic semialdehyde in urine and cerebrospinal fluid by dinitrophenylhydrazine derivatization and liquid chromatography-tandem mass spectrometry: application to SSADH deficiency," J Inherit Metab Dis., 28(6):913-20 (2005).
Struys et al., "Metabolism of gamma-hydroxybutyrate to d-2-hydroxyglutarate in mammals: further evidence for d-2-hydroxyglutarate transhydrogenase," Metabolism, 55(3):353-8 (2006).
Study showing effect of ADX-102 on Fibrotic Changes in Cardiac Fibroblasts Following Cell Stress, American Society for Cell Biology Annual Meeting, Dec. 3-7, 2016 (2 pages).
Sus et al., "Uber die Lichtreaktion der o-Chinondiazide V. Mitteilung1) Ubergange heterocyclischer 6-Ringe in heterocyclische 5-Ringe," Liebigs Ann. Chem. 583:150 (1953).
Tahara et al., "Pharmacological characterization of the human vasopressin receptor subtypes stably expressed in Chinese hamster ovary cells," Brit. J. Pharmacol., 125:1463-1470 (1998).
Tang-Liu et al., "Effects of four penetration enhancers on corneal permeability of drugs in vitro," Journal of Pharmaceutical Sciences, 83(1):85-90 (1994).
Tanna et al., "Stargardt disease: clinical features, molecular genetics, animal models and therapeutic options," Br J Ophthalmol. 2017; 101(1):25-30.
Tatsumi et al., "Pharmacological profile of neuroleptics at human monoamine transporters," Eur. J. Pharmacol., 368 : 277-283 (1999).
Tayeh et al., "Macrophage oxidation of L-arginine to nitric oxide, nitrite, and nitrate. Tetrahydrobiopterin is required as a cofactor," J. Biol. Chem., 264:19654-19658 (1989).
Tempest-Roe et al., "Local therapies for inflammatory eye disease in translation: past, present and future," BMC Ophthalmol, 13(1):39 (Aug. 2013).
Tewari-Singh et al., "Silibinin attenuates sulfur mustard analog-induced skin injury by targeting multiple pathways connecting oxidative stress and inflammation," PLoS One 7(9):e46149 (2012).
Tian et al., "First total synthesis and determination of the absolute configuration of 1-N-methyl-3-methylamino-[N-butanoicacid-3-(9-methyl-8-propen-7-one)-amide]—benzo[f][1,7]naphthyridine-2-one, a novel benzonaphthyridine alkaloid," Tetrahedron Letters, 53:4892-4895 (2012).
Tikly et al., "Lipid peroxidation and trace elements in systemic sclerosis," Clinical Rheumatology, 25(3):320-324 (2006).
Torkildsen et al., "Efficacy and safety of olopatadine hydrochloride 0.77% in patients with allergic conjunctivitis using a conjunctival allergen-challenge model," Clinical Ophthalmology, 9:1703-1713 (2015).
Toth et al., "A simple, continuous fluorometric assay for HIV protease," Int. J. Pept. Protein Res., 36:544-550 (1990).
Tsugeno et al., "Regions of the molecule responsible for substrate specificity of monoamine oxidase A and B: a chimeric enzyme analysis," J. Biochem., 118 (5) 974-80 (1995).
Tsuzuki et al., "Molecular cloning and expression of the gene encoding human angiotensin II type 2 receptor.," Biochem. Biophys. Res. Commun., 200:1449-1454 (1994).
Tukozkan et al., "Measurement of Total Malondialdehyde in Plasma and tissues by High-Performance Liquid Chromatography and Thiobarbituric Acid Assay," Firat Tip Dergisi, 11(2):88-92 (2006).
Turk et al., "Serum anti-carbonic anhydrase antibodies and oxidant-antioxidant balance in patients with acute anterior uveitis," Ocul Immunol Inflamm, 22(2):127-32 (Apr. 2014).
U.S. Appl. No. 16/547,930 of Buist et al., filed Aug. 22, 2019.
Ueda et al., "Evaluation of a Sulfobutyl Ether 13-Cyclodextrin as a Solubilizing/Stabilizing Agent for Several Drugs," Drug Dev Ind Pharm, 24(9):863-867(1998).
Upadhyaya et al., "The sphingolipid degradation product trans-2-hexadecenal forms adducts with DNA," Biochem Biophy Res Comm., 424(1):18-21 (2012).
Vanachayangkul et al., "Inhibition of heme peroxidases by melamine," Enzyme Research, 2012:416062 (2012).

(56) References Cited

OTHER PUBLICATIONS

Vignon et al., "[3H]thienyl-phencyclidine ([3H]TCP) binds to two different sites in rat brain. Localization by autoradiographic and biochemical techniques," Brain Res., 378:133-141 (1986).
Vlaskina et al., "Novel Synthesis of Substituted Benzimidazoles by Reduction of Esters of 4-Alkylamino-3,5-dinitrobenzoic Acids by Tin Chloride," Chemistry of Heterocyclic Compounds, vol. 40(4):523-524 (2004).
Vogel et al, "Thirty years beyond discovery—clinical trials in succinic semialdehyde dehydrogenase deficiency, a disorder of GABA metabolism," J Inherit Metab Dis., 36(3):401-10 (2013).
Voziyan et al., "A Post-Amadori Inhibitor Pyridoxamine also Inhibits Chemical Modification of Proteins by Scavenging Carbonyl Intermediates for Carbohydrate and Lipid Degradation," J Biol Chem, 277(5):3397-3403 (2002).
Wagner et al., "Omega-conotoxin GVIA binding to a high-affinity receptor in brain: characterization, calcium sensitivity, and solubilization," J. Neurosci., 8:3354-3359 (1988).
Wakamatsu et al., "Evaluation of lipid oxidative stress status and inflammation in atopic ocular surface disease," Mol Vis, 16:2465-75 (Nov. 2010).
Wang et al., "A facile one-pot synthesis of 2-substituted-3-aminoquinolines: Preparation of benzo[b]naphthyridine-3-carbonitriles," Tetrahedron, 60(13):2937-2942 (2004).
Wang et al., "Human mu opiate receptor. cDNA and genomic clones, pharmacologic characterization and chromosomal assignment," FEBS Lett., 338:217-222 (1994).
Wang et al., "Markers of oxidative and nitrosative stress in systemic lupus erythematosus: correlation with disease activity," Arthritis and Rheumatism, 62(7):2064-2072 (2010).
Wang, X.K., "Pharmacological study on recombinant human GABA-A receptor complex containing alpha5 (leucine155 to valine) combined with beta3gamma2s subunits," Acta. Pharmacol. Sin., 22:521-523 (2001).
Waslidge et al., "A colorimetric method for the determination of lipoxygenase activity suitable for use in a high throughput assay format," Anal. Biochem., 231:354-358 (1995).
Weaver et al., "The Th17 pathway and inflammatory diseases of the intestines, lungs, and skin," Annu. Rev. Pathol., 8:477-512 (2013).
Webb et al., "Intralesional cytokines in chronic oxazolone-induced contact sensitivity suggest roles for tumor necrosis factor alpha and interleukin-4," J Invest Dermatol, 111(1):86-92 (Jul. 1998).
Weishaar et al., "Multiple molecular forms of cyclic nucleotide phosphodiesterase in cardiac and smooth muscle and in platelets. Isolation, characterization, and effects of various reference phosphodiesterase inhibitors and cardiotonic agents," Biochem. Pharmacol., 35:787-800 (1986).
Weng et al., "Insights into the Function of Rim Protein in Photoreceptors and Etiology of Stargardt's Disease from the Phenotype in abcr Knockout Mice," Cell, 98(1):13-23 (1999).
Westphal et al., "Reactions with Pryridinium Pyruvic Acid Esters," Pharmazie, 31(11):770-773 (1976).
Westphal et al., "Reactions with Pryridinium Pyruvic Acid Esters," Pharmazie, 31(11):770-773 (1976) [English Translation].
Wieland et al., "Subtype selectivity and antagonistic profile of the nonpeptide Y1 receptor antagonist BIBP 3226," J. Pharmacol. Exp. Ther., 275:143-149 (1995).
Witt-Enderby et al., "Characterization and regulation of the human ML1A melatonin receptor stably expressed in Chinese hamster ovary cells," Mol. Pharmacol., 50:166-174 (1996).
Wolkenberg et al., "Design, synthesis, and evaluation of novel 3,6-diaryl-4-aminoalkoxyquinolines as selective agonists of somatostatin receptor subtype 2," J Med Chem, 54(7):2351-2358 (2011).
Wood et al., "Aldehyde Load in lschemia-Reperfusion Brain Injury: Neuroprotection by Neutralization of reactive Aldehydes with Phenelzine," Brain Res, 1122(1):184-190 (2006).
Wood et al., "The concept of "aldehyde load" in neurodegenerative mechanisms: cytotoxicity of the polyamine degradation products hydrogen peroxide, acrolein, 3-aminopropanal, 3-acetamidiorioanal and 4-aminobutanal in a retinal ganglion cell line," Brain Research, 1145:150-156 (2007).
Wurch et al., "Sequence and functional analysis of cloned guinea pig and rat serotonin 5-HT1 D receptors: common pharmacological features within the 5-HT1D receptor subfamily," J. Neurochem., 68:410-418 (1997).
Wynn, "Cellular and molecular mechanisms of fibrosis," J Pathol. 2008; 214(2):199-210.
Yadav et al., "Regulation of NF-kB-Induced Inflammatory Signaling by Lipid Peroxidation-Derived Aldehydes," Oxidative Med & Cell Longev, 2013, Art ID 690545, 11 pages (2013).
Yarnell, "Light Flips the Lipid Switch: Palmitoylation—the reversible attachment of palmitate to proteins—gets a new role in vision," C&EN, 82(29):22-23 (2004).
Yokomizo et al., "Hydroxyeicosanoids bind to and activate the low affinity leukotriene B4 receptor, BLT2," J. Biol. Chem., 276:12454-12459 (2001).
Yu et al., "Injectable Chemically Crosslinked Hydrogel for the Controlled Release of Bevacizumab in Vitreous: a 6-Month in Vivo Study," Transl Vis Sci Technol, 4(2,5):1-11 (2015).
Zagol-Ikapitte et al., "Characterization of scavengers of γ-ketoaldehydes that do not inhibit prostaglandin biosynthesis," Chem Res Toxicol, 23(1):240-250 (2010).
Zarkovic "4-hydroxynonenal and neurodegenerative diseases," Molecular Aspects of Medicine, 24(4-5):293-303 (2003).
Zava et al., "Androgen receptor assay with [3H]methyltrienolone (R1881) in the presence of progesterone receptors," Endocrinology, 104:1007-1012 (1979).
Zhang et al., "Potent nonsteroidal progesterone receptor agonists: synthesis and SAR study of 6-aryl benzoxazines," Bioorg Med Chem Lett, 12(5):787-90 (Mar. 2002).
Zhou et al, "Cloning and expression of human and rat D1 dopamine receptors," Nature, 347:76-80 (1990).
Zhou et al., "Chemical and biological evidence for base propenals as the major source of the endogenous M1dG adduct in cellular DNA," J Biol Chem., 280(27):25377-82 (2005).
Zhou et al., "Mechanisms for the induction of HNE- MDA- and AGE-adducts, RAGE and VEGF in retinal pigment epithelial cells," Exp Eye Res., 80(4):567-80 (2005).

A

B

A

Hamster check pouch irradiation with 40 Gy
(n=10 per group, 12.5 mg/kg SQ BID Compound 9)

% Animals with Ulceration

|  | Day 18 | Day 20 | Day 22 | Day 24 | Day 26 | Day 28 | Day 30 | Day 32 | Day 34 | Day 36 |
|---|---|---|---|---|---|---|---|---|---|---|
| Vehicle | 100% | 90% | 90% | 90% | 80% | 50% | 50% | 20% | 30% | 40% |
| Compound 9 | 100% | 100% | 70% | 50% | 40% | 20% | 20% | 20% | 0% | 0% |

B

TOXIC ALDEHYDE RELATED DISEASES AND TREATMENT

CROSS-REFERENCE TO RELATED APPLICATIONS

This application is a continuation of U.S. application Ser. No. 16/773,654, filed Jan. 27, 2020; which is a continuation of U.S. application Ser. No. 16/277,865, filed Feb. 15, 2019, now U.S. Pat. No. 10,588,874; and is a continuation of U.S. application Ser. No. 16/262,364, filed Jan. 30, 2019, now U.S. Pat. No. 10,543,181; which applications are continuations of U.S. application Ser. No. 15/590,708, filed May 9, 2017, now U.S. Pat. No. 10,213,395; which is a continuation of U.S. application Ser. No. 14/760,039, filed Jul. 9, 2015, now U.S. Pat. No. 9,687,481; which is a National Stage of International Application No. PCT/US2014/012762, filed Jan. 23, 2014, which claims the benefit under 35 U.S.C. § 119(e) of U.S. Provisional Application No. 61/755,613, filed Jan. 23, 2013, and U.S. Provisional Application No. 61/901, 796, filed Nov. 8, 2013; the contents of each of which are incorporated herein by reference in their entirety.

BACKGROUND OF THE INVENTION

Metabolic and inflammatory processes in cells generate toxic aldehydes, such as malondialdehyde (MDA), 4-hydroxyl-2-nonenal (4HNE), and 8-hydroxy-2-deoxyguanosine (8-OHdg). These aldehydes are highly reactive to proteins, carbohydrates, lipids and DNA, leading to chemically modified biological molecules, activation of inflammatory mediators such as NF-kappaB, and damages in diverse organs. For example, retinaldehyde can react with phosphatidylethanolamine (PE) to form a highly toxic compound called A2E, which is a component of lipofuscin believed to be involved in the development and progression of Age Related Macular Degeneration (AMD). Many bodily defense mechanisms function to remove or lower the levels of toxic aldehydes. Novel small molecule therapeutics can be used to scavenge "escaped" retinaldehyde in the retina, thus reducing A2E formation and lessening the risk of AMD (Jordan et al. (2006)).

Aldehydes are implicated in diverse pathological conditions such as dry eye, cataracts, keratoconus, Fuch's endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjogren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., lupus), cardiovascular disorders (e.g., atherosclerosis), and conditions associated with the injurious effects of blister agents (Negre-Salvagre et al. (2008), Nakamura et al. (2007), Batista et al. (2012), Kenney et al. (2003), Int J Dermatol 43: 494 (2004), Invest Ophthalmol Vis Sci 48: 1552 (2007), Graefe's Clin Exp Ophthalmol 233: 694 (1994), Molecular Vision 18: 194 (2012)). Reducing or eliminating aldehydes should thus ameliorate the symptoms and slow the progression of these pathological conditions.

MDA, HNE and other toxic aldehydes are generated by a myriad of metabolic mechanisms involving: fatty alcohols, sphingolipids, glycolipids, phytol, fatty acids, arachadonic acid metabolism (Rizzo (2007)), polyamine metabolism (Wood et al. (2006)), lipid peroxidation, oxidative metabolism (Buddi et al. (2002), Zhou et al. (2005)), and glucose metabolism (Pozzi et al. (2009)). Aldehydes can cross link with primary amino groups and other chemical moieties on proteins, phospholipids, carbohydrates, and DNA, leading in many cases to toxic consequences, such as mutagenesis and carcinogenesis (Marnett (2002)). MDA is associated with diseased corneas, keratoconus, bullous and other keratopathy, and Fuch's endothelial dystrophy corneas (Buddi et al. (2002)). Also, skin disorders, e.g., Sjogren-Larsson Syndrome, are likely connected with the accumulation of fatty aldehydes such as octadecanal and hexadecanal (Rizzo et al. (2010)). Further, increased lipid peroxidation and resultant aldehyde generation are associated with the toxic effects of blister agents (Sciuto et al. (2004) and Pal et al. (2009)).

There has been no suggestion in the art for treating the various conditions associated with toxic aldehydes by the administration of small molecule therapeutics acting as a scavenger for aldehydes, such as MDA and/or HNE. Thus, there is a need for treating, preventing, and/or reducing a risk of a disease or disorder in which aldehyde toxicity is implicated in the pathogenesis. The present invention addresses such a need.

SUMMARY OF THE INVENTION

The invention relates to a method of treating, preventing, and/or reducing a risk of a disease, disorder, or condition in which aldehyde toxicity is implicated in the pathogenesis, by administering a compound (e.g., a primary amine compound) described herein. The invention also relates to the use of a compound (e.g., a primary amine compound) described herein in the manufacture of a medicament for the treatment, prevention, and/or reduction of a risk of a disease, disorder, or condition in which aldehyde toxicity is implicated in the pathogenesis, or the use of a compound (e.g., a primary amine compound) described herein in treating, preventing, and/or reducing a risk of a disease, disorder, or condition in which aldehyde toxicity is implicated in the pathogenesis.

In one embodiment, a disease, disorder, or condition in which aldehyde toxicity is implicated in the pathogenesis is an ocular disease, disorder, or condition, including, but not limited to, a corneal disease (e.g., dry eye syndrome, cataracts, keratoconus, bullous and other keratopathy, and Fuch's endothelial dystrophy), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions associated with high aldehyde levels as a result of inflammation (e.g., uveitis, scleritis, ocular Stevens Johnson Syndrome, and ocular rosacea (with or without meibomian gland dysfunction)).

In a second embodiment, a disease, disorder, or condition in which aldehyde toxicity is implicated in the pathogenesis is a skin disorder or condition or a cosmetic indication. For example, the disease, disorder, or condition includes, but is not limited to, psoriasis, scleroderma, topical (discoid) lupus, contact dermatitis, atopic dermatitis, allergic dermatitis, radiation dermatitis, acne vulgaris, Sjogren-Larsson Syndrome and other ichthyosis, and the cosmetic indication is solar elastosis/wrinkles, skin tone firmness, puffiness, eczema, smoke or irritant induced skin changes, dermal incision, and a skin condition associated burn and/or wound.

In a third embodiment, a disease, disorder, or condition in which aldehyde toxicity is implicated in the pathogenesis is a condition associated with the toxic effects of blister agents or burns from alkali agents.

In a fourth embodiment, a disease, disorder, or condition in which aldehyde toxicity is implicated in the pathogenesis is an autoimmune, immune-mediated, inflammatory, cardiovascular, or neurological disease. For example, the disease, disorder, or condition includes, but is not limited to, lupus, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, multiple sclerosis, amyotrophic lateral sclerosis, diabetes, metabolic syndrome, and fibrotic diseases.

A compound (e.g., a primary amine compound) described herein can be administered topically or systemically, as described in detail below.

Unless otherwise defined, all technical and scientific terms used herein have the same meaning as commonly understood by one of ordinary skill in the art to which this invention belongs. In the case of conflict, the present specification, including definitions, will control. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In addition, the materials, methods, and examples are illustrative only and are not intended to be limiting.

Other features and advantages of the invention will be apparent from the following detailed description and claims.

DETAILED DESCRIPTION OF THE INVENTION

Figure 1:
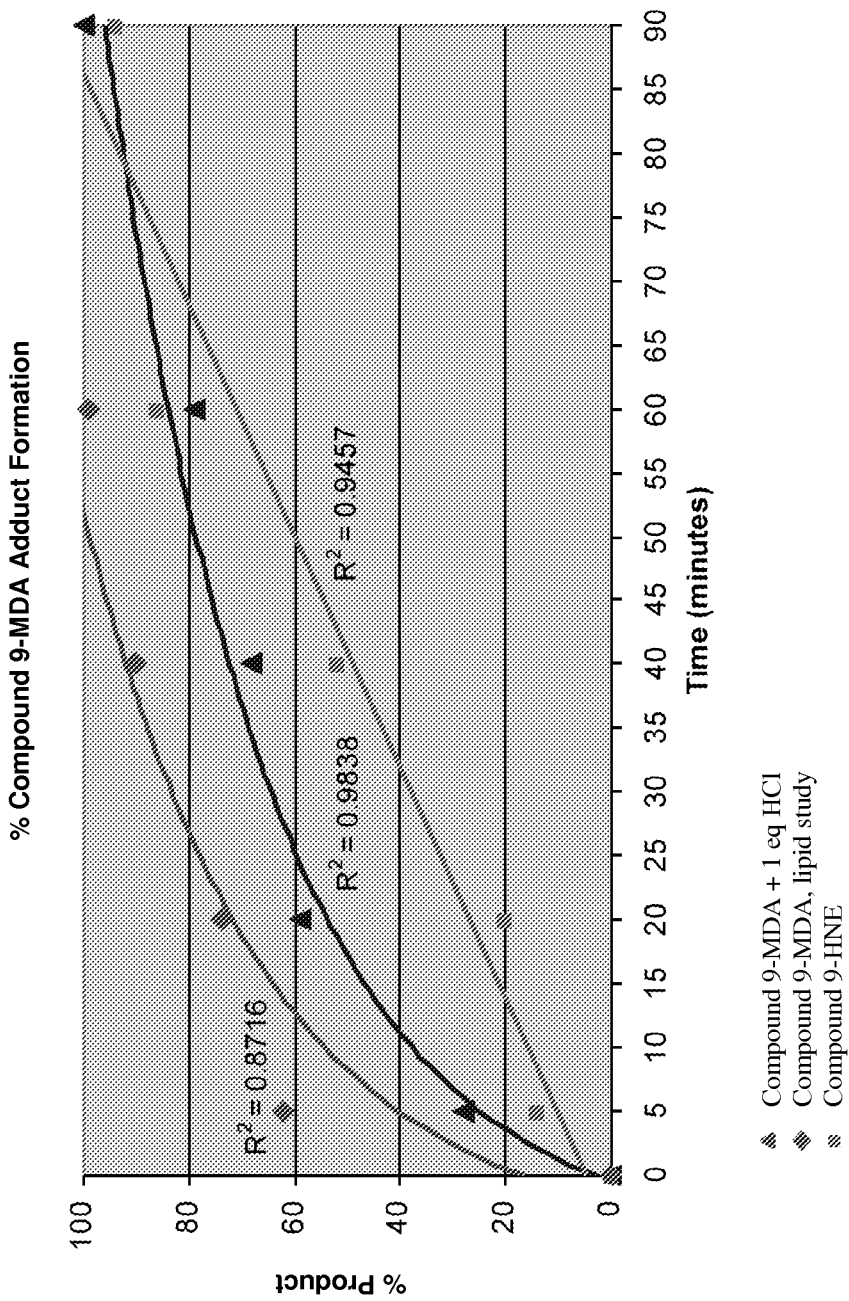
FIG. 1. A plot showing that Compound 9 rapidly reacts with and traps the two most common pathogenic aldehydes: malondialdehye (MDA) and 4-hydroxynonenal (HNE)

The invention relates to compounds (e.g., a primary amine compound) for the treatment, prevention, and/or reduction of a risk of diseases, disorders, or conditions in which aldehyde toxicity is implicated in the pathogenesis.

Examples of the diseases, disorders, or conditions in which aldehyde toxicity is implicated include an ocular disease, disorder, or condition, including, but not limited to, a corneal disease (e.g., dry eye syndrome, cataracts, keratoconus, bullous and other keratopathy, and Fuch's endothelial dystrophy), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions associated with high aldehyde levels as a result of inflammation (e.g., uveitis, scleritis, ocular Stevens Johnson Syndrome, ocular rosacea (with or without meibomian gland dysfunction)). In one example, the ocular disease, disorder, or condition is not macular degeneration, such as age-related macular degeneration ("AMD"), or Stargardt's disease. In a further example, the ocular disease, disorder, or condition is dry eye syndrome, ocular rosacea, or uveitis.

Examples of the diseases, disorders, conditions, or indications in which aldehyde toxicity is implicated also include non-ocular disorders, including psoriasis, topical (discoid) lupus, contact dermatitis, atopic dermatitis, allergic dermatitis, radiation dermatitis, acne vulgaris, Sjogren-Larsson Syndrome and other ichthyosis, solar elastosis/wrinkles, skin tone firmness, puffiness, eczema, smoke or irritant induced skin changes, dermal incision, a skin condition associated burn and/or wound, lupus, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, multiple sclerosis, amyotrophic lateral sclerosis, diabetes, metabolic syndrome, and fibrotic diseases. In a further example, the non-ocular disorder is a skin disease, disorder, or condition selected from contact dermatitis, atopic dermatitis, allergic dermatitis, and. radiation dermatitis. In another example, the non-ocular disorder is a skin disease, disorder, or condition selected from Sjogren-Larsson Syndrome and a cosmetic indication associated burn and/or wound.

Examples of the diseases, disorders, or conditions in which aldehyde toxicity is implicated further include conditions associated with the toxic effects of blister agents or burns from alkali agents. The compounds described herein reduce or eliminate toxic aldehydes and thus treat, prevent, and/or reduce a risk of these diseases or disorders.

Certain compounds comprising primary amine groups (e.g., compounds described herein) are found to be useful in scavenging toxic aldehydes, such as MDA and HNE. The compounds described herein undergo a Schiff base condensation with MDA, HNE, or other toxic aldehydes, and form a complex with the aldehydes in an energetically favorable reaction, thus reducing or eliminating aldehydes available for reaction with a protein, lipid, carbohydrate, or DNA. Importantly, compounds described herein can react with aldehydes to form a compound having a closed-ring structure that contains the aldehydes, thus trapping the aldehydes and preventing the aldehydes from being released back into the cellular milieu. For example, Compound 9,

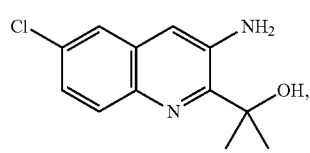 [SMILES: CC(C)(O)c1nc2ccc(Cl)cc2cc1N]

disclosed in PCT publication WO 2006/127945, rapidly traps MDA and HNE, even in the presence of peptides and phospholipids, which are the biological targets of these aldehydes.

In addition, primary amine compounds described in US 2012/0295895 and Maeda et al. (2012), the contents of each of which are incorporated herein by reference in their entirety, can reduce levels of all trans-retinal and prevent accumulation of conjugation products in the retina. The primary compounds described therein are thus useful in scavenging and trapping aldehydes, such as MDA and HNE. For example, compounds disclosed therein with an optical coherence tomography (OCT) grade of 2 or less are useful in scavenging and trapping aldehydes, such as MDA and HNE. In a further example, compounds disclosed therein with an OCT grade of 1 or less are useful in scavenging and trapping aldehydes, such as MDA and HNE. Particular examples include 3-(aminomethyl)-5-methylhexanoic acid (both stereoisomers), 6-(trifluromethoxy)benzothiazol-2-amine, and 3-ethyl-5-methyl-2-(aminoethoxy)methyl-4-(2-chlorophenyl)-6-methyl-1,4-dihydropyridine-3,5-dicarboxylate.

U.S. Pat. No. 7,982,071, the contents of which are incorporated herein by reference in their entirety, describes certain alkoxy derivatives containing a primary amine group. Those compounds are useful in the treatment of certain ophthalmic disorders, specifically AMD and Stargardt's disease. Compounds described in the 071 patent, particularly Compound (11)

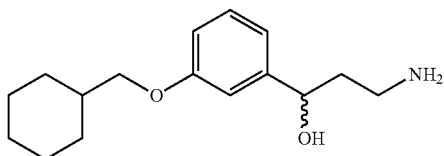

are found to be useful in treating a disease, disorder, or condition described herein, such as an ocular disease, disorder, or condition (e.g., dry eye syndrome, conditions associated with PRK or other corneal healing, uveitis, scleritis, ocular Stevens Johnson syndrome, ocular rosacea (with or without meibomian gland dysfunction), cataracts, keratoconus, bullous and other keratopathy, and endothelial dystrophy and related disorders).

Further, compounds described in PCT Application Nos. PCT/US2013/076592 and PCT/US2014/012356, the contents of each of which are incorporated herein by reference in their entirety, are effective in effective in scavenging and trapping MDA and HNE and other toxic aldehydes. Those compounds are found to be useful in treating a disease, disorder, or condition described herein, such as an ocular disease, disorder, or condition (e.g., dry eye syndrome, conditions associated with PRK or other corneal healing, uveitis, scleritis, ocular Stevens Johnson syndrome, ocular rosacea (with or without meibomian gland dysfunction), cataracts, keratoconus, bullous and other keratopathy, and endothelial dystrophy and related disorders).

In one embodiment, the invention relates to the treatment, prevention, and/or reduction of a risk of an ocular disease, disorder, or condition in which aldehyde toxicity is implicated in the pathogenesis, comprising administering to a subject in need thereof a compound described herein. The ocular disease, disorder, or condition includes, but is not limited to, a corneal disease (e.g., dry eye syndrome, cataracts, keratoconus, bullous and other keratopathy, and Fuch's endothelial dystrophy in the cornea), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions where inflammation leads to high aldehyde levels (e.g., uveitis, scleritis, ocular Stevens Johnson Syndrome, ocular rosacea (with or without meibomian gland dysfunction)). The ocular disease, disorder, or condition does not include macular degeneration, such as AMD, or Stargardt's disease. In one illustration, in the ocular disease, disorder, or condition, the amount or concentration of MDA or HNE is increased in the ocular tissues or cells. For example, the amount or concentration of aldehydes (e.g., MDA or HNE) is increased for at least 1.1 fold, 1.2 fold, 1.3 fold, 1.4 fold, 1.5 fold, 2 fold, 2.5 fold, 5 fold, 10 fold as compared to that in normal ocular tissues or cells. Compounds described herein, such as Compound 9, decrease aldehyde (e.g., MDA and HNE) concentration in a time-dependent manner. The amount or concentration of aldehydes (e.g., MDA or HNE) can be measured by methods or techniques known in the art, such as those described in Tukozkan et al., Furat Tip Dergisi 11: 88-92 (2006).

In one class, the ocular disease, disorder, or condition is dry eye syndrome. In a second class, the ocular disease, disorder, or condition is a condition associated with PRK healing and other corneal healing. For example, the invention is directed to advancing PRK healing or other corneal healing, comprising administering to a subject in need thereof a compound described herein. In a third class, the ocular disease, disorder, or condition is an ocular condition associated with high aldehyde levels as a result of inflammation (e.g., uveitis, scleritis, ocular Stevens Johnson Syndrome, and ocular rosacea (with or without meibomian gland dysfunction). In a fourth class, the ocular disease, disorder, or condition is keratoconus, cataracts, bullous and other keratopathy, Fuchs' endothelial dystrophy, ocular cicatricial pemphigoid, or allergic conjunctivitis. The compound described herein may be administered topically or systemically, as described herein below.

In a first aspect of this embodiment, the invention relates to the treatment, prevention, and/or reduction of a risk of each of the ocular diseases, disorders, or conditions described herein, comprising administering a compound of formula (I):

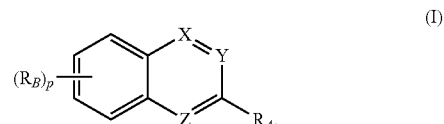

or a pharmaceutically acceptable salt thereof, wherein each of the variables in formula (I) is described in detail below.

In one exemplification, the invention relates to the treatment, prevention, and/or reduction of a risk of each of the ocular diseases, disorders, or conditions described herein, comprising administering a compound of each of the various illustrations and/or examples of the compounds of formula (I) described herein.

In one specific exemplification, the invention relates to the treatment, prevention, and/or reduction of a risk of each of the ocular diseases, disorders, or conditions described herein, comprising administering Compound (9):

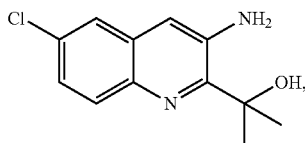
(9)

or a pharmaceutically acceptable salt thereof.

In a second aspect of this embodiment, the invention relates to the treatment, prevention, and/or reduction of a risk of each of the ocular diseases, disorders, or conditions described herein, comprising administering a compound of formula (II):

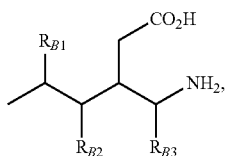
(II)

or a pharmaceutically acceptable salt thereof, wherein each of the variables in formula (II) is described in detail below.

In one exemplification, the invention relates to the treatment, prevention, and/or reduction of a risk of each of the ocular diseases, disorders, or conditions described herein, comprising administering a compound of each of the various illustrations and/or examples of the compounds of formula (II) described herein.

In one specific exemplification, the invention relates to the treatment, prevention, and/or reduction of a risk of each of the ocular diseases, disorders, or conditions described herein, comprising administering a compound selected from the compounds listed in Table 2. Preferably, the compound is (S)-3-(aminomethyl)-5-methylhexanoic acid or (R)-3-(aminomethyl)-5-methylhexanoic acid, or pharmaceutically acceptable salts or racemic mixtures thereof.

In a third aspect of this embodiment, the invention relates to the treatment, prevention, and/or reduction of a risk of each of the ocular diseases, disorders, or conditions described herein, comprising administering Compound (11):

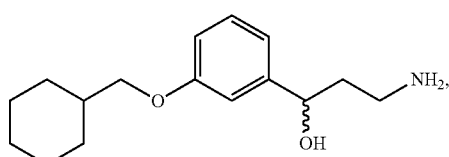
(11)

or a pharmaceutically acceptable salt thereof.

In one illustration of this aspect, the compound is:

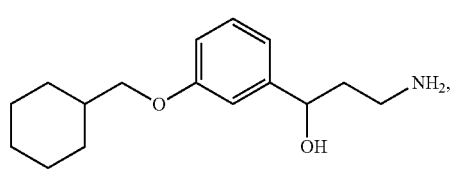

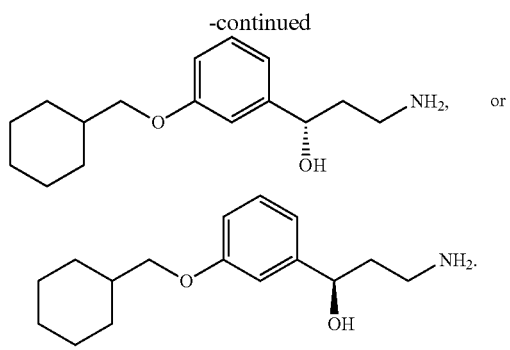

In a fourth aspect of this embodiment, the invention relates to the treatment, prevention, and/or reduction of a risk of each of the ocular diseases, disorders, or conditions described herein, comprising administering a compound of any one of formulae (IIIa)-(IIIf):

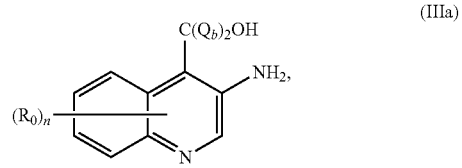
(IIIa)

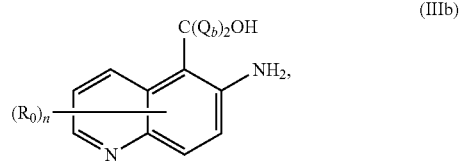
(IIIb)

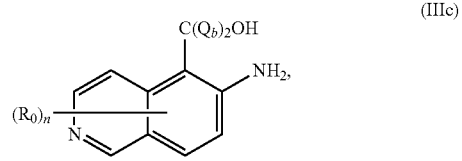
(IIIc)

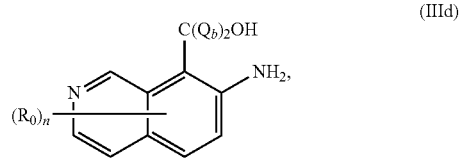
(IIId)

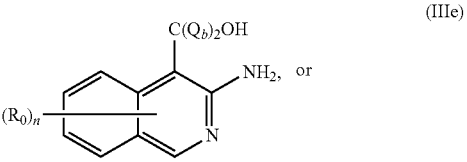
(IIIe)

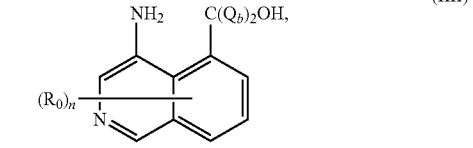
(IIIf)

or a pharmaceutically acceptable salt thereof, wherein each of the variables in formulae (IIIa)-(IIIf) is described in detail below.

In one exemplification, the invention relates to the treatment, prevention, and/or reduction of a risk of each of the ocular diseases, disorders, or conditions described herein, comprising administering a compound of each of the various illustrations and/or examples of the compounds of each of formulae (IIIa)-(IIIf) described herein.

In one specific exemplification, the invention relates to the treatment, prevention, and/or reduction of a risk of each of the ocular diseases, disorders, or conditions described herein, comprising administering a compound selected from Compounds (1)-(8):

(1)
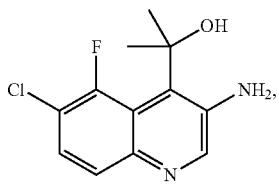

(2)
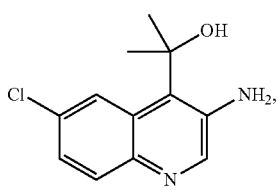

(3)
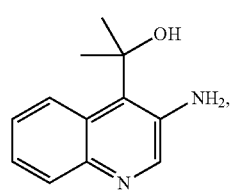

(4)
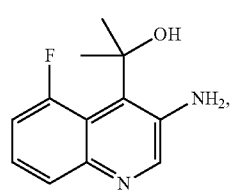

(5)
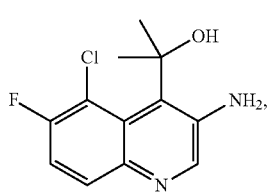

(6)
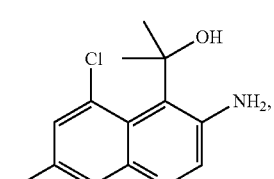

(7)
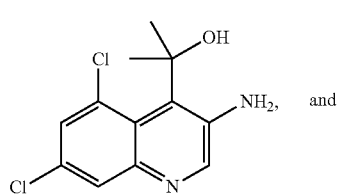 and (8)

or a pharmaceutically acceptable salt thereof. Preferably, the compound is Compound (1) or (2).

In another specific exemplification, the invention relates to the treatment, prevention, and/or reduction of a risk of each of the ocular diseases, disorders, or conditions described herein, comprising administering Compound (10):

(10)
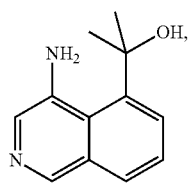

or a pharmaceutically acceptable salt thereof.

In a fifth aspect of this embodiment, the invention relates to the treatment, prevention, and/or reduction of a risk of each of the ocular diseases, disorders, or conditions described herein, comprising administering a compound of formula (IV):

(IV)
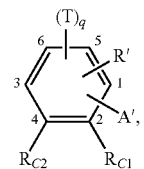

or a pharmaceutically acceptable salt thereof, wherein each of the variables in formula (IV) is described in detail below.

In one class of this aspect, the invention relates to the treatment, prevention, and/or reduction of a risk of each of the ocular diseases, disorders, or conditions described herein, comprising administering a compound of formula (IVa) or formula (IVb):

(IVa)
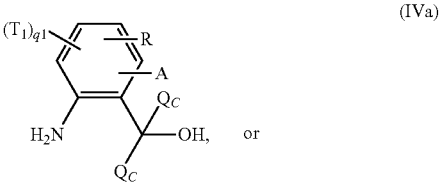 or

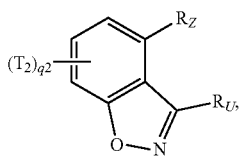

(IVb)

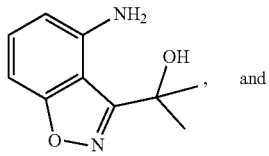

(17)

and

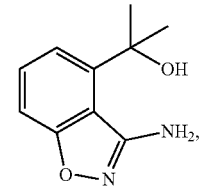

(18)

or a pharmaceutically acceptable salt thereof, wherein each of the variables in formulae (IVa) and (IVb) is described in detail below.

In one exemplification, the invention relates to the treatment, prevention, and/or reduction of a risk of each of the ocular diseases, disorders, or conditions described herein, comprising administering a compound of each of the various illustrations and/or examples of the compounds of each of formula (IV), (IVa), and (IVb) described herein.

In one specific exemplification, the invention relates to the treatment, prevention, and/or reduction of a risk of each of the ocular diseases, disorders, or conditions described herein, comprising administering a compound selected from Compounds (12)-(18):

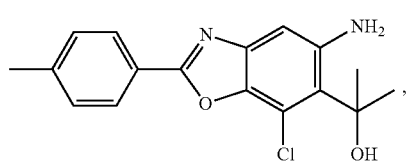

(12)

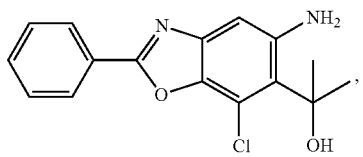

(13)

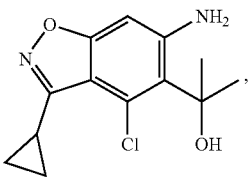

(14)

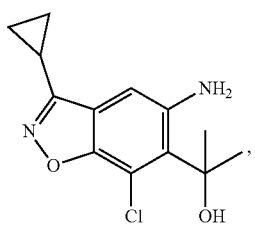

(15)

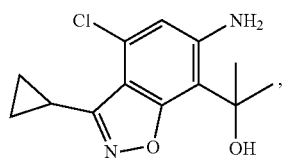

(16)

or a pharmaceutically acceptable salt thereof.

In a second embodiment, the invention relates to the treatment, prevention, and/or reduction of a risk of a skin disorder or condition or a cosmetic indication, in which aldehyde toxicity is implicated in the pathogenesis, comprising administering to a subject in need thereof a compound described herein. The skin disorder or condition includes, but is not limited to, psoriasis, scleroderma, topical (discoid) lupus, contact dermatitis, atopic dermatitis, allergic dermatitis, radiation dermatitis, acne vulgaris, and Sjogren-Larsson Syndrome and other ichthyosis, and the cosmetic indication is solar elastosis/wrinkles, skin tone firmness, puffiness, eczema, smoke or irritant induced skin changes, dermal incision, or a skin condition associated burn and/or wound.

Various skin disorders or conditions, such as atopic dermatitis, topical (discoid) lupus, psoriasis and scleroderma, are characterized by high MDA and HNE levels (Br J Dermatol 149: 248 (2003); JEADV 26: 833 (2012); Clin Rheumatol 25: 320 (2006)). In addition, ichthyosis characteristic of the Sjogren-Larsson Syndrome (SLS) originates from accumulation of fatty aldehydes, which disrupts the normal function and secretion of lamellar bodies (LB) and leads to intercellular lipid deposits in the Strateum Corneum (SC) and a defective water barrier in the skin layer (W. B. Rizzo et al. (2010)). The enzyme, fatty aldehyde dehydrogenase, that metabolizes aldehydes is dysfunctional in SLS patients. Thus, compounds that reduce or eliminate aldehydes, such as the compounds described herein, can be used to treat, prevent, and/or reduction of a risk of skin disorders or conditions in which aldehyde toxicity is implicated in the pathogenesis, such as those described herein. Furthermore, with an improvement to the water barrier and prevention of aldehyde-mediated inflammation (including fibrosis and elastosis (Chairpotto et al. (2005)), many cosmetic indications, such as solar elastosis/wrinkles, skin tone, firmness (puffiness), eczema, smoke or irritant induced skin changes and dermal incision cosmesis, and skin conditions associated with burn and/or wound can be treated using the method of the invention. For example, Compound (9) is effective against contact dermatitis in a phorbol myristate acetate model and allergic dermatitis in an oxazolone model.

In one class, the skin disease, disorder, or condition is psoriasis, scleroderma, topical (discoid) lupus, contact dermatitis, atopic dermatitis, allergic dermatitis, radiation dermatitis, acne vulgaris, or Sjogren-Larsson Syndrome and other ichthyosis. In one exemplification, the skin disease, disorder, or condition is contact dermatitis, atopic dermatitis, allergic dermatitis, radiation dermatitis, or Sjogren-Larsson Syndrome and other ichthyosis. In a second class, the cosmetic indication is solar elastosis/wrinkles, skin tone firmness, puffiness, eczema, smoke or irritant induced skin changes, dermal incision, or a skin condition associated burn and/or wound.

In a first aspect of this embodiment, the invention relates to the treatment, prevention, and/or reduction of a risk of each of the skin disorders or conditions or cosmetic indications described herein, comprising administering a compound of formula (I):

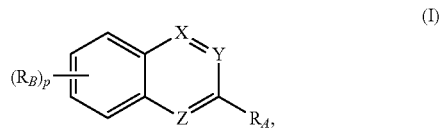

(I)

or a pharmaceutically acceptable salt thereof, wherein each of the variables in formula (I) is described in detail below.

In one exemplification, the invention relates to the treatment, prevention, and/or reduction of a risk of each of the skin disorders or conditions or cosmetic indications described herein, comprising administering a compound of each of the various illustrations and/or examples of the compounds of formula (I) described herein.

In one specific exemplification, the invention relates to the treatment, prevention, and/or reduction of a risk of each of the skin disorders or conditions or cosmetic indications described herein, comprising administering Compound (9):

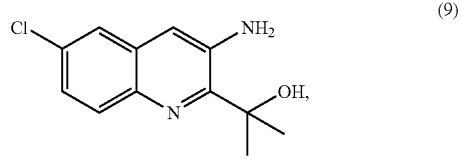 [SMILES: CC(C)(O)c1nc2ccc(Cl)cc2cc1N]

(9)

or a pharmaceutically acceptable salt thereof.

In a second aspect of this embodiment, the invention relates to the treatment, prevention, and/or reduction of a risk of each of the skin disorders or conditions or cosmetic indications described herein, comprising administering a compound of formula (II):

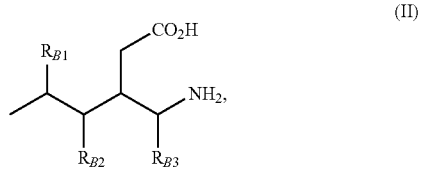

(II)

or a pharmaceutically acceptable salt thereof, wherein each of the variables in formula (II) is described in detail below.

In one exemplification, the invention relates to the treatment, prevention, and/or reduction of a risk of each of the skin disorders or conditions or cosmetic indications described herein, comprising administering a compound of each of the various illustrations and/or examples of the compounds of formula (II) described herein.

In one specific exemplification, the invention relates to the treatment, prevention, and/or reduction of a risk of each of the skin disorders or conditions or cosmetic indications described herein, comprising administering a compound selected from the compounds listed in Table 2. Preferably, the compound is (S)-3-(aminomethyl)-5-methylhexanoic acid or (R)-3-(aminomethyl)-5-methylhexanoic acid, or pharmaceutically acceptable salts or racemic mixtures thereof.

In a third aspect of this embodiment, the invention relates to the treatment, prevention, and/or reduction of a risk of each of the skin disorders or conditions or cosmetic indications described herein, comprising administering Compound (11):

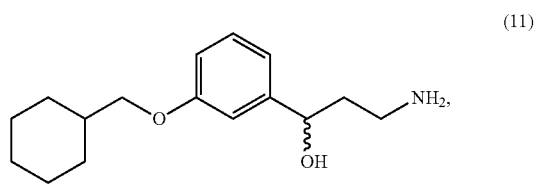

(11)

or a pharmaceutically acceptable salt thereof.

In one illustration of this aspect, the compound is:

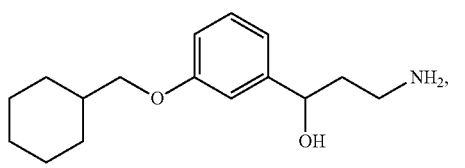

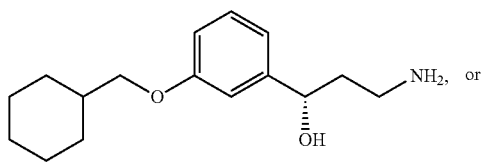

or

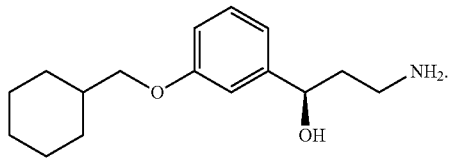

In a fourth aspect of this embodiment, the invention relates to the treatment, prevention, and/or reduction of a risk of each of the skin disorders or conditions or cosmetic indications described herein, comprising administering a compound of any one of formulae (IIIa)-(IIIf):

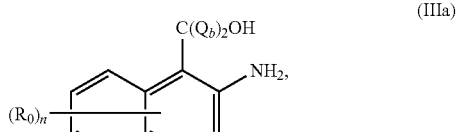

(IIIa)

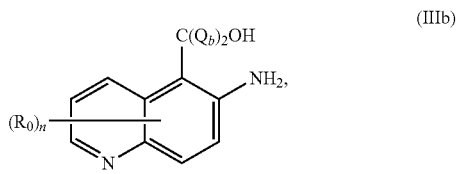

(IIIb)

15

-continued

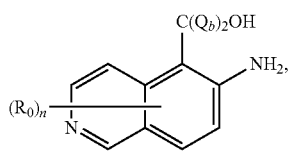
(IIIc)

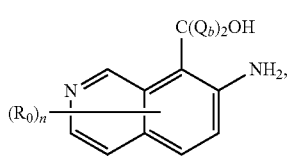
(IIId)

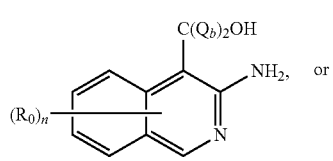
(IIIe)

or

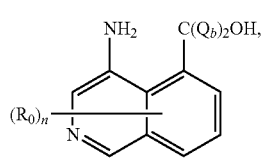
(IIIf)

or a pharmaceutically acceptable salt thereof, wherein each of the variables in formulae (IIIa)-(IIIf) is described in detail below.

In one exemplification, the invention relates to the treatment, prevention, and/or reduction of a risk of each of the skin disorders or conditions or cosmetic indications described herein, comprising administering a compound of each of the various illustrations and/or examples of the compounds of each of formulae (IIIa)-(IIIf) described herein.

In one specific exemplification, the invention relates to the treatment, prevention, and/or reduction of a risk of each of the skin disorders or conditions or cosmetic indications described herein, comprising administering a compound selected from Compounds (1)-(8):

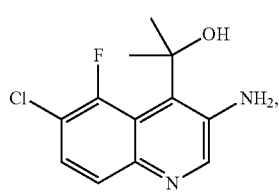
(1)

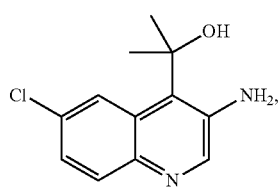
(2)

16

-continued

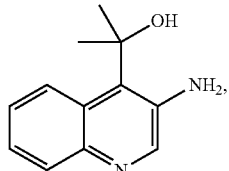
(3)

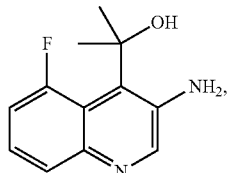
(4)

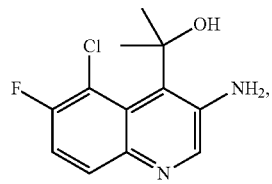
(5)

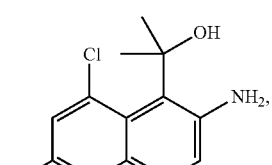
(6)

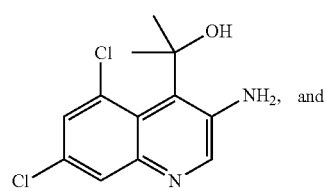
(7)
and

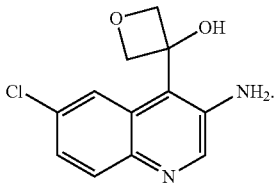
(8)

or a pharmaceutically acceptable salt thereof. Preferably, the compound is Compound (1) or (2).

In another specific exemplification, the invention relates to the treatment, prevention, and/or reduction of a risk of each of the skin disorders or conditions or cosmetic indications described herein, comprising administering Compound (10):

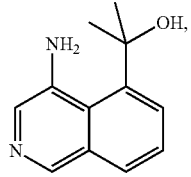
(10)

or a pharmaceutically acceptable salt thereof.

In a fifth aspect of this embodiment, the invention relates to the treatment, prevention, and/or reduction of a risk of each of the skin disorders or conditions or cosmetic indications described herein, comprising administering a compound of formula (IV):

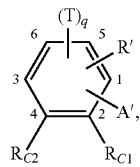
(IV)

or a pharmaceutically acceptable salt thereof, wherein each of the variables in formula (IV) is described in detail below.

In one class of this aspect, the invention relates to the treatment, prevention, and/or reduction of a risk of each of the skin disorders or conditions or cosmetic indications described herein, comprising administering a compound of formula (IVa) or formula (IVb):

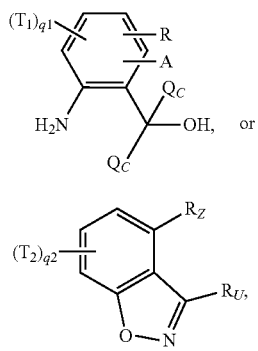
(IVa)
(IVb)

or a pharmaceutically acceptable salt thereof, wherein each of the variables in formulae (IVa) and (IVb) is described in detail below.

In one exemplification, the invention relates to the treatment, prevention, and/or reduction of a risk of each of the skin disorders or conditions or cosmetic indications described herein, comprising administering a compound of each of the various illustrations and/or examples of the compounds of each of formula (IV), (IVa), and (IVb) described herein.

In one specific exemplification, the invention relates to the treatment, prevention, and/or reduction of a risk of each of the skin disorders or conditions or cosmetic indications described herein, comprising administering a compound selected from Compounds (12)-(18):

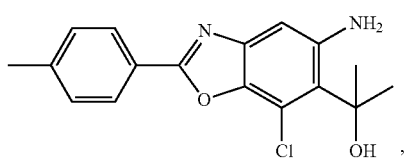
(12)

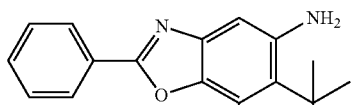
(13)

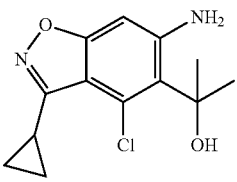
(14)

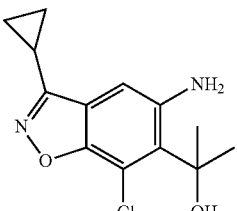
(15)

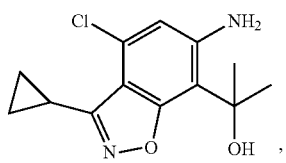
(16)

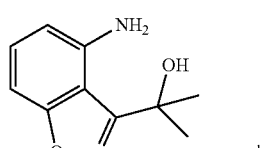
(17)

and

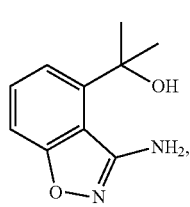
(18)

or a pharmaceutically acceptable salt thereof.

In a third embodiment, the invention relates to the treatment, prevention, and/or reduction of a risk of a condition associated with the toxic effects of blister agents or burns from alkali agents in which aldehyde toxicity is implicated in the pathogenesis, comprising administering to a subject in need thereof a compound described herein.

Blister agents include, but are not limited to, sulfur mustard, nitrogen mustard, and phosgene oxime. Toxic or injurious effects of blister agents include pain, irritation, and/or tearing in the skin, eye, and/or mucous, and conjunctivitis and/or corneal damage to the eye. Sulfur mustard is the compound bis(2-chlorethyl) sulfide. Nitrogen mustard includes the compounds bis(2-chlorethyl)ethylamine, bis(2-chlorethyl)methylamine, and tris(2-chlorethyl)amine. Sulfur mustard or its analogs can cause an increase in oxidative stress and in particular in FINE levels, and by depleting the antioxidant defense system and thereby increasing lipid peroxidation, may induce an oxidative stress response and thus increase aldehyde levels (Jafari et al. (2010); Pal et al.

(2009)). Antioxidants, such as Silibinin, when applied topically, attenuate skin injury induced from exposure to sulfur mustard or its analogs, and increased activities of antioxidant enzymes may be a compensatory response to reactive oxygen species generated by the sulfur mustard (Jafari et al. (2010); Tewari-Singh et al. (2012)). Further, intervention to reduce free radical species was an effective treatment post exposure for phosgene induced lung injury (Sciuto et al. (2004)). Thus, compounds that reduce or eliminate aldehydes, such as compounds described herein, can be used to treat, prevent, and/or reduce a risk of a condition associated with the toxic effects of blister agents, such as sulfur mustard, nitrogen mustard, and phosgene oxime.

Alkali agents include, but are not limited to, lime, lye, ammonia, and drain cleaners. Compounds that reduce or eliminate aldehydes, such as compounds described herein, can be used to treat, prevent, and/or reduce a risk of a condition associated with burns from an alkali agent.

In a first aspect of this embodiment, the invention relates to the treatment, prevention, and/or reduction of a risk of the condition associated with the toxic effects of blister agents or burns from alkali agents described herein, comprising administering a compound of formula (I):

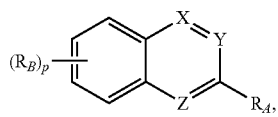

or a pharmaceutically acceptable salt thereof, wherein each of the variables in formula (I) is described in detail below.

In one exemplification, the invention relates to the treatment, prevention, and/or reduction of a risk of the condition associated with the toxic effects of blister agents or burns from alkali agents described herein, comprising administering a compound of each of the various illustrations and/or examples of the compounds of formula (I) described herein.

In one specific exemplification, the invention relates to the treatment, prevention, and/or reduction of a risk of the condition associated with the toxic effects of blister agents or burns from alkali agents described herein, comprising administering Compound (9):

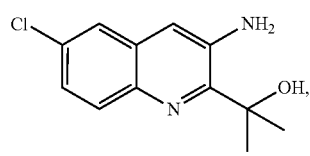

or a pharmaceutically acceptable salt thereof.

In a second aspect of this embodiment, the invention relates to the treatment, prevention, and/or reduction of a risk of the condition associated with the toxic effects of blister agents or burns from alkali agents described herein, comprising administering a compound of formula (II):

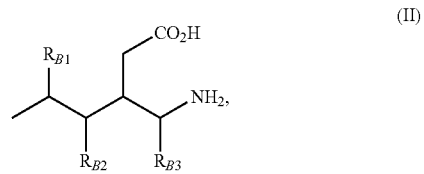

or a pharmaceutically acceptable salt thereof, wherein each of the variables in formula (II) is described in detail below.

In one exemplification, the invention relates to the treatment, prevention, and/or reduction of a risk of the condition associated with the toxic effects of blister agents or burns from alkali agents described herein, comprising administering a compound of each of the various illustrations and/or examples of the compounds of formula (II) described herein.

In one specific exemplification, the invention relates to the treatment, prevention, and/or reduction of a risk of the condition associated with the toxic effects of blister agents or burns from alkali agents described herein, comprising administering a compound selected from the compounds listed in Table 2. Preferably, the compound is (S)-3-(aminomethyl)-5-methylhexanoic acid or (R)-3-(aminomethyl)-5-methylhexanoic acid, or pharmaceutically acceptable salts or racemic mixtures thereof.

In a third aspect of this embodiment, the invention relates to the treatment, prevention, and/or reduction of a risk of the condition associated with the toxic effects of blister agents or burns from alkali agents described herein, comprising administering Compound (11):

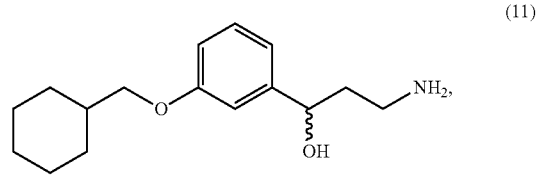 [SMILES: NCCC(O)c1cccc(OCC2CCCCC2)c1]

or a pharmaceutically acceptable salt thereof.

In one illustration of this aspect, the compound is:

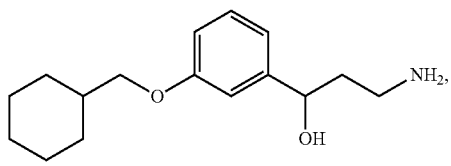

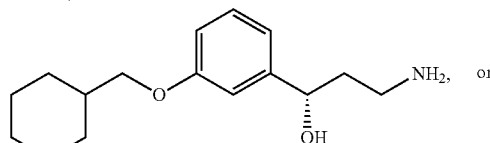

or

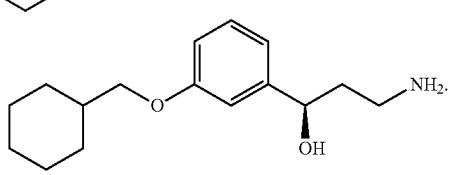

In a fourth aspect of this embodiment, the invention relates to the treatment, prevention, and/or reduction of a risk of the condition associated with the toxic effects of blister agents or burns from alkali agents described herein, comprising administering a compound of any one of formulae (IIIa)-(IIIf):

(IIIa)

[chemical structure: quinoline with $C(Q_b)_2OH$ at 4-position, $NH_2$ at 3-position, $(R_0)_n$ substituents]

(IIIb)

[chemical structure: quinoline with $C(Q_b)_2OH$, $NH_2$, $(R_0)_n$]

(IIIc)

[chemical structure: isoquinoline with $C(Q_b)_2OH$, $NH_2$, $(R_0)_n$]

(IIId)

[chemical structure: isoquinoline variant with $C(Q_b)_2OH$, $NH_2$, $(R_0)_n$]

(IIIe)

[chemical structure: isoquinoline with $C(Q_b)_2OH$, $NH_2$, $(R_0)_n$], or (IIIf)

[chemical structure: isoquinoline with $NH_2$, $C(Q_b)_2OH$, $(R_0)_n$], or a pharmaceutically acceptable salt thereof, wherein each of the variables in formulae (IIIa)-(IIIf) is described in detail below.

In one exemplification, the invention relates to the treatment, prevention, and/or reduction of a risk of the condition associated with the toxic effects of blister agents or burns from alkali agents described herein, comprising administering a compound of each of the various illustrations and/or examples of the compounds of each of formulae (IIIa)-(IIIf) described herein.

In one specific exemplification, the invention relates to the treatment, prevention, and/or reduction of a risk of the condition associated with the toxic effects of blister agents or burns from alkali agents described herein, comprising administering a compound selected from Compounds (1)-(8):

(1)

[chemical structure: 6-Cl, 5-F quinoline with C(CH3)2OH and NH2]

(2)

[chemical structure: 6-Cl quinoline with C(CH3)2OH and NH2]

(3)

[chemical structure: quinoline with C(CH3)2OH and NH2]

(4)

[chemical structure: 5-F quinoline with C(CH3)2OH and NH2]

(5)

[chemical structure: 6-Cl, 5-F quinoline with C(CH3)2OH and NH2]

(6)

[chemical structure: 5-Cl, 7-F quinoline with C(CH3)2OH and NH2]

(7)

[chemical structure: 5-Cl, 7-Cl quinoline with C(CH3)2OH and NH2], and (8)

[chemical structure: 6-Cl quinoline with oxetanyl-OH and NH2].

or a pharmaceutically acceptable salt thereof. Preferably, the compound is Compound (1) or (2).

In another specific exemplification, the invention relates to the treatment, prevention, and/or reduction of a risk of the condition associated with the toxic effects of blister agents or burns from alkali agents described herein, comprising administering Compound (10):

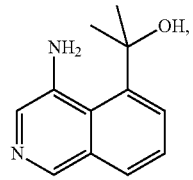

or a pharmaceutically acceptable salt thereof.

In a fifth aspect of this embodiment, the invention relates to the treatment, prevention, and/or reduction of a risk of the condition associated with the toxic effects of blister agents or burns from alkali agents described herein, comprising administering a compound of formula (IV):

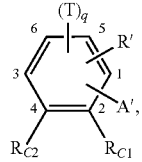

or a pharmaceutically acceptable salt thereof, wherein each of the variables in formula (IV) is described in detail below.

In one class of this aspect, the invention relates to the treatment, prevention, and/or reduction of a risk of the condition associated with the toxic effects of blister agents or burns from alkali agents described herein, comprising administering a compound of formula (IVa) or formula (IVb):

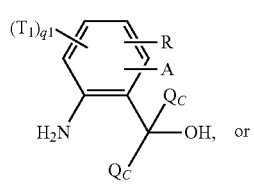

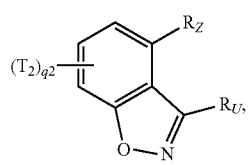

or a pharmaceutically acceptable salt thereof, wherein each of the variables in formulae (IVa) and (IVb) is described in detail below.

In one exemplification, the invention relates to the treatment, prevention, and/or reduction of a risk of the condition associated with the toxic effects of blister agents or burns from alkali agents described herein, comprising administering a compound of each of the various illustrations and/or examples of the compounds of each of formula (IV), (IVa), and (IVb) described herein.

In one specific exemplification, the invention relates to the treatment, prevention, and/or reduction of a risk of the condition associated with the toxic effects of blister agents or burns from alkali agents described herein, comprising administering a compound selected from Compounds (12)-(18):

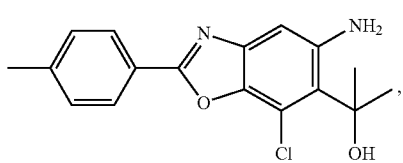

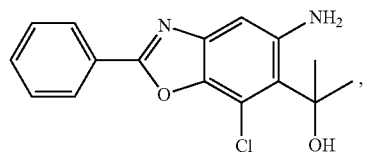

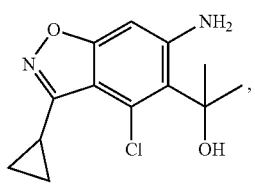

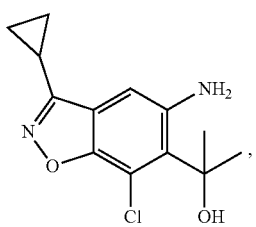

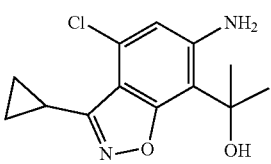

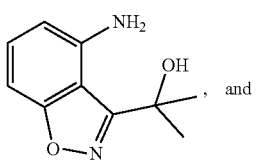

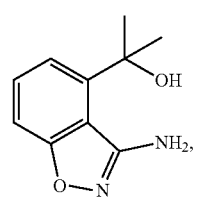

or a pharmaceutically acceptable salt thereof.

In a fourth embodiment, the invention relates to the treatment, prevention, and/or reduction of a risk of an autoimmune, immune-mediated, inflammatory, cardiovascular, or neurological disease, disorder, or condition, or metabolic syndrome, or diabetes, in which aldehyde toxicity is implicated in the pathogenesis, comprising administering to a subject in need thereof a compound described herein. The autoimmune or immune-mediated disease, disorder, or condition includes, but is not limited to, lupus, scleroderma, asthma, chronic obstructive pulmonary disease (COPD), and rheumatoid arthritis. The inflammatory disease, disorder, or condition includes, but is not limited to, rheumatoid arthritis, inflammatory bowel disease (e.g., Crohn's disease and ulcerative colitis), sepsis, and fibrosis (e.g., renal, hepatic, pulmonary, and cardiac fibrosis). The cardiovascular disease, disorder, or condition includes, but is not limited to, atherosclerosis and ischemic-reperfusion injury. The neurological disease, disorder, or condition includes, but is not limited to, Parkinson's disease, Alzheimer's disease, multiple sclerosis, amyotrophic lateral sclerosis, and the neurological aspects of Sjogren-Larsson Syndrome (cognitive delay and spasticity).

A skilled person would understand that the disease, disorder, or condition listed herein may involve more than one pathological mechanisms. For example, a disease, disorder, or condition listed herein may involve dysregulation in the immunological response and inflammatory response. Thus, the above categorization of a disease, disorder, or condition is not absolute, and the disease, disorder, or condition may be considered an immunological, an inflammatory, a cardiovascular, a neurological, and/or metabolic disease, disorder, or condition.

Individuals with deficiencies in aldehyde dehydrogenase are found to have high aldehyde levels and increased risk of Parkinson's disease (PNAS 110:636 (2013)) and Alzheimer's disease (BioChem Biophys Res Commun. 273:192 (2000)). In Parkinson's disease, aldehydes specifically interfere with dopamine physiology (Free Radic Biol Med, 51: 1302 (2011); Mol Aspects Med, 24: 293 (2003); Brain Res, 1145: 150 (2007)). In addition, aldehydes levels are elevated in multiple sclerosis, amyotrophic lateral sclerosis, autoimmune diseases such as lupus, rheumatoid arthritis, lupus, psoriasis, scleroderma, and fibrotic diseases, and increased levels of HNE and MDA are implicated in the progression of atherosclerosis and diabetes (J. Cell. Mol. Med., 15: 1339 (2011); Arthritis Rheum 62: 2064 (2010); Clin Exp Immunol, 101: 233 (1995); Int J Rheum Dis, 14: 325 (2011); JEADV 26: 833 (2012); Clin Rheumatol 25: 320 (2006); Gut 54: 987 (2005); J Am Soc Nephrol 20: 2119 (2009)). MDA is further implicated in the increased formation of foam cells leading to atherosclerosis (Leibundgut et al., Current Opinion in Pharmacology 13: 168 (2013)). Also, aldehyde-related toxicity plays an important role in the pathogenesis of many inflammatory lung diseases, such as asthma and chronic obstructive pulmonary disease (COPD) (Bartoli et al., Mediators of Inflammation 2011, Article 891752). Thus, compounds that reduce or eliminate aldehydes, such as compounds described herein, can be used to treat, prevent, and/or reduce a risk of an autoimmune, immune-mediated, inflammatory, cardiovascular, or neurological disease, disorder, or condition, or metabolic syndrome, or diabetes. For example, compounds described herein, such as Compound 9, prevent aldehyde-mediated cell death in neurons. Further, compounds described herein, such as Compound 9, down-regulate a broad spectrum of pro-inflammatory cytokines and/or upregulate anti-inflammatory cytokines, which indicates that compounds described herein are useful in treating inflammatory diseases, such as multiple sclerosis and amyotrophic lateral sclerosis.

In a first aspect of this embodiment, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering a compound of formula (I):

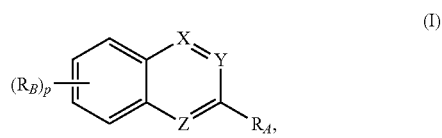

or a pharmaceutically acceptable salt thereof, wherein each of the variables in formula (I) is described in detail below.

In one exemplification, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering a compound of each of the various illustrations and/or examples of the compounds of formula (I) described herein.

In one specific exemplification, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering Compound (9):

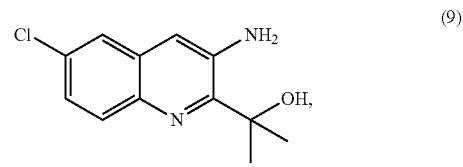 [SMILES: CC(C)(O)c1nc2ccc(Cl)cc2cc1N]

or a pharmaceutically acceptable salt thereof.

In a second aspect of this embodiment, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering a compound of formula (II):

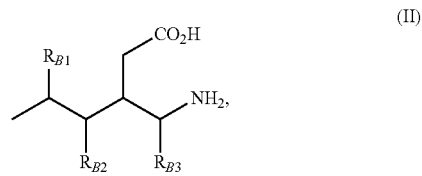

or a pharmaceutically acceptable salt thereof, wherein each of the variables in formula (II) is described in detail below.

In one exemplification, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering a compound of each of the various illustrations and/or examples of the compounds of formula (II) described herein.

In one specific exemplification, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering a compound selected from the compounds listed in Table 2. Preferably, the compound is (S)-3-(aminomethyl)-5-methylhexanoic acid or (R)-3-(aminomethyl)-5-methylhexanoic acid, or pharmaceutically acceptable salts or racemic mixtures thereof.

In a third aspect of this embodiment, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering Compound (11):

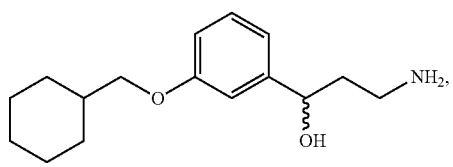

(11)

or a pharmaceutically acceptable salt thereof.

In one illustration of this aspect, the compound is:

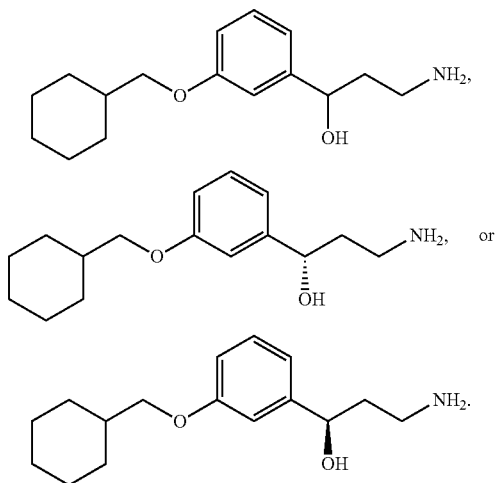

In a fourth aspect of this embodiment, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering a compound of any one of formulae (IIIa)-(IIIf):

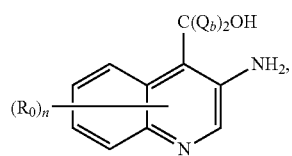

(IIIa)

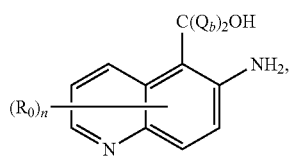

(IIIb)

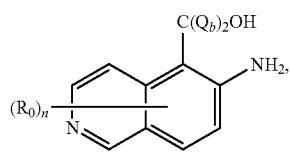

(IIIc)

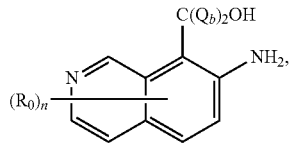

(IIId)

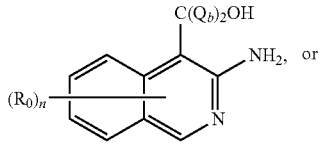

(IIIe)

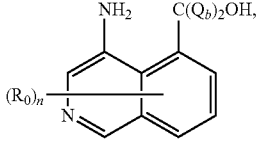

(IIIf)

or a pharmaceutically acceptable salt thereof, wherein each of the variables in formulae (IIIa)-(IIIf) is described in detail below.

In one exemplification, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering a compound of each of the various illustrations and/or examples of the compounds of each of formulae (IIIa)-(IIIf) described herein.

In one specific exemplification, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering a compound selected from Compounds (1)-(8):

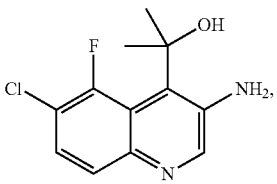

(1)

(2)
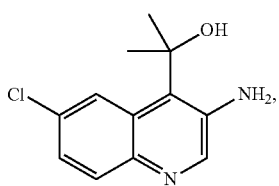

(3)
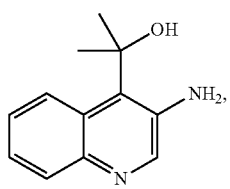

(4)
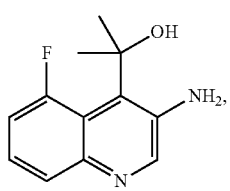

(5)
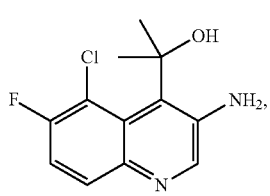

(6)
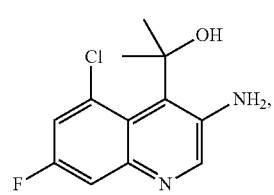

(7)
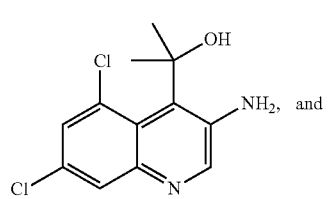

(8)
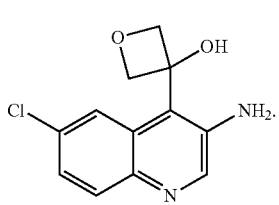

or a pharmaceutically acceptable salt thereof. Preferably, the compound is Compound (1) or (2).

In another specific exemplification, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering Compound (10):

(10)
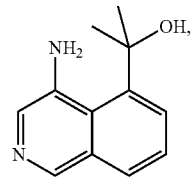

or a pharmaceutically acceptable salt thereof.

In a fifth aspect of this embodiment, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering a compound of formula (IV):

(IV)
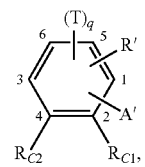

or a pharmaceutically acceptable salt thereof, wherein each of the variables in formula (IV) is described in detail below.

In one class of this aspect, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering a compound of formula (IVa) or formula (IVb):

(IVa)
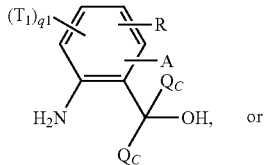

(IVb)
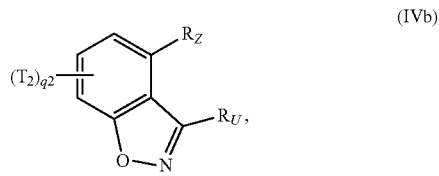

or a pharmaceutically acceptable salt thereof, wherein each of the variables in formulae (IVa) and (IVb) is described in detail below.

In one exemplification, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering a compound of each of the various illustrations and/or examples of the compounds of each of formula (IV), (IVa), and (IVb) described herein.

In one specific exemplification, the invention relates to the treatment, prevention, and/or reduction of a risk of each of the autoimmune, immune-mediated, inflammatory, cardiovascular, or neurological diseases, disorders, or conditions, or metabolic syndromes, or diabetes described herein, comprising administering a compound selected from Compounds (12)-(18):

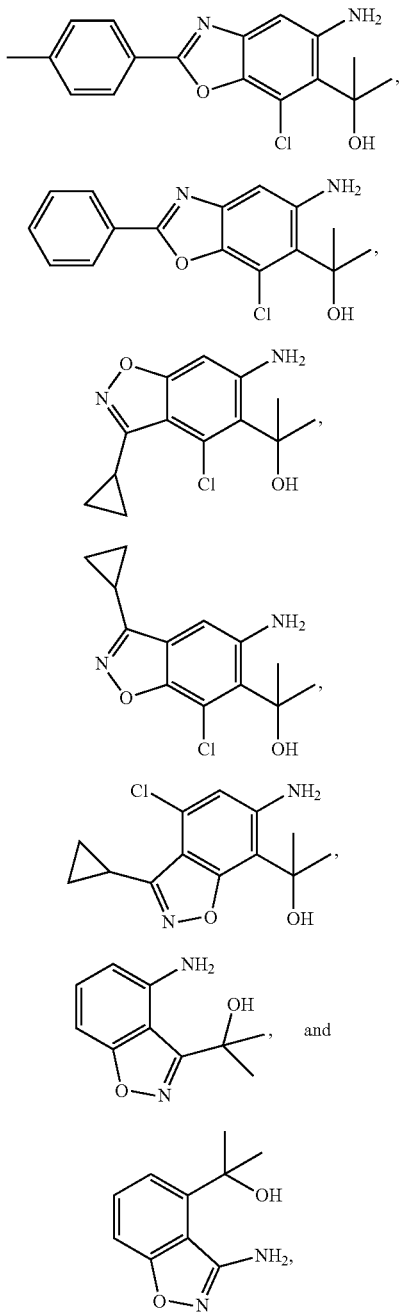

or a pharmaceutically acceptable salt thereof.

Compounds Useful in the Invention

Compounds that can be used in the invention are compounds that contain one or more primary amine groups and react with aldehydes (e.g., MDA and HNE) to form a complex, for example, through a Schiff base condensation mechanism. Preferably, the aldehyde complex so formed has a closed-ring structure, thus preventing the aldehyde from being released from the complex and back into the cellular milieu, where the aldehyde can react with various cellular targets, such as a protein, lipid, carbohydrate, and DNA, and interfere with numerous normal physiological processes, thus resulting in diseases, disorders, and other undesirable conditions. Thus, compounds that can be used in the invention are compounds which react with and thus decrease or eliminate aldehydes (e.g., MDA and HNE). For example, the compounds decrease the amount or concentration of aldehydes by at least 10%, 20%, 30%, 40%, 50%, 60%, 70%, 80%, or 90%, as compared to the amount or concentration of aldehydes in the absence of the compounds.

In addition, compounds described in the invention may possess activities in addition to reacting with aldehydes. In one example, compounds described herein may affect the expression or amount of chemokines in the cells. In a further example, compounds described herein may downregulate a broad spectrum of pro-inflammatory cytokines, including but not limited to, IL-5 and IL-1β, IL-12, IL-17, and TNF. In another example, compounds described herein may upregulate anti-inflammatory cytokines, including but not limited to, IL-10. In another example, compounds described herein may downregulate other cytokines involved in inflammation, including but not limited to, eotaxin, IP-10, LIF, MCP-1, MIG, MIP, and RANTES. In another example, compounds described herein may prevent aldehyde-mediated death of various types of cells, such as neurons.

In one aspect, compounds that can be used in the invention include a compound of formula (I):

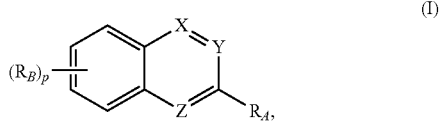

or a pharmaceutically acceptable salt thereof, wherein:

X, Y, and Z are each independently N, CH, or C(NH$_2$), provided that one of X, Y, and Z is N;

p is 0, 1, 2, or 3;

each R$_B$ is independently halogen, hydroxyl, carbamoyl, amino, or unsubstituted or substituted aryl;

R$_A$ is

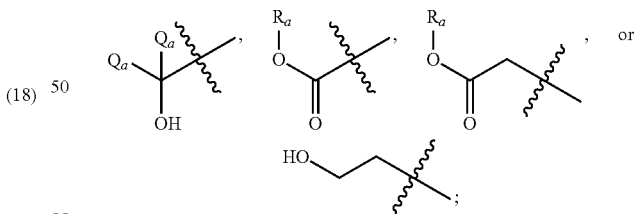

Q$_a$ is C$_1$-C$_6$ straight chain alkyl; and

R$_a$ is unsubstituted or substituted C$_1$-C$_8$ straight chain or C$_3$-C$_8$ branched alkyl.

In one illustration, R$_a$ is C$_1$-C$_8$ straight chain or C$_3$-C$_8$ branched alkyl substituted with one or more substituents independently selected from alkenyl, alkynyl, halogen, hydroxyl, alkylcarbonyloxy, arylcarbonyloxy, alkoxycarbonyloxy, aryloxycarbonyloxy, carboxylate, alkylcarbonyl, aryl carbonyl, alkoxycarbonyl, aminocarbonyl, alkylaminocarbonyl, di alkylaminocarbonyl, alkylthiocarbonyl, alkoxyl, phosphate, phosphonato, phosphinato, cyano, NH$_2$, alkylamino, dialkylamino, arylamino, diarylamino, alkylarylamino, acylamino, alkylcarbonylamino, arylcarbonylamino, carbamoyl, ureido, amidino, imino, sulfhydryl, alkylthio, arylthio, thiocarboxylate, sulfate, alkylsulfinyl, sulfamoyl, sulfonamido, trifluoromethyl, azido, heterocyclyl, alkylaryl, and an aromatic or heteroaromatic moiety.

In one illustration, $R_B$ is aryl substituted with one or more substituents independently selected from halogen, hydroxyl, alkoxy, alkylcarbonyloxy, arylcarbonyloxy, alkoxycarbonyloxy, aryloxycarbonyloxy, carboxylate, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, $NH_2$, alkylamino, dialkylamino, arylamino, diarylamino, alkylarylamino, acylamino, alkylcarbonylamino, arylcarbonylamino, carbamoyl, ureido, amidino, imino, sulfhydryl, alkylthio, arylthio, thiocarboxylate, sulfate, alkylsulfinyl, sulfonato, sulfamoyl, sulfonamido, nitro, trifluoromethyl, azido, heterocyclyl, alkylaryl, and an aromatic or heteroaromatic moiety.

In one illustration, the compounds of formula (I) are the compounds wherein X is CH; Z is N; Y is $C(NH_2)$.

In another illustration, the compounds of formula (I) are the compounds wherein p is 1. In another illustration, the compounds of formula (I) are the compounds wherein $R_A$ is

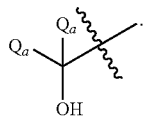

In a further illustration, the compounds of formula (I) are the compounds wherein p is 1 and $R_A$ is

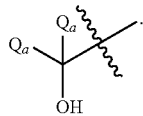

In yet a further illustration, the compounds of formula (I) are the compounds wherein p is 1; $R_A$ is

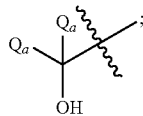

and each $Q_a$ is methyl.

In another illustration, the compounds of formula (I) are the compounds wherein $R_B$ is halogen, hydroxyl, carbamoyl, amino, or aryl.

In another illustration, the compounds of formula (I) are the compounds wherein $R_B$ is halogen. In a further illustration, the compounds of formula (I) are the compounds wherein p is 1; $R_A$ is

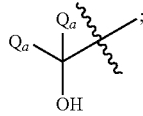

and $R_B$ is halogen. In yet a further illustration, the compounds of formula (I) are the compounds wherein p is 1; $R_A$ is

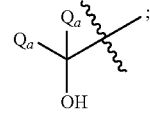

each $Q_a$ is methyl; and $R_B$ is halogen. In one exemplification, $R_B$ is Cl.

In one exemplification, a compound of formula (I) is Compound (9):

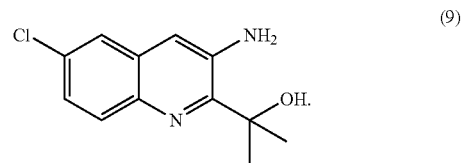 [SMILES: CC(C)(O)c1nc2ccc(Cl)cc2cc1N]

In a second aspect, compounds that can be used in the invention include a compound of formula (II):

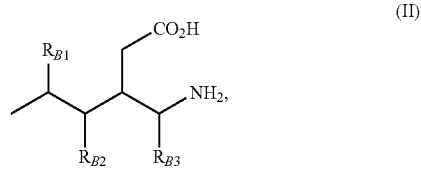

or a pharmaceutically acceptable salt thereof, wherein:

$R_{B1}$ is unsubstituted or substituted $C_1$-$C_8$ straight chain or $C_3$-$C_8$ branched alkyl, $C_2$-$C_8$ straight chain or $C_3$-$C_8$ branched alkenyl, $C_1$-$C_6$ alkoxy, $C_3$-$C_7$ cycloalkyl, $C_1$-$C_6$ alkyl-$C_3$-$C_7$ cycloalkyl, hydroxyl, $C_1$-$C_6$ alkylphenoxy, phenyl, or substituted phenyl;

$R_{B2}$ is H, unsubstituted or substituted $C_1$-$C_6$ straight chain or $C_3$-$C_6$ branched alkyl, phenyl, or substituted phenyl; and $R_{B3}$ is H, unsubstituted or substituted $C_1$-$C_6$ straight chain or branched $C_3$-$C_6$ alkyl, or carboxyl.

In one illustration, the compounds of formula (II) are the compounds wherein $R_{B3}$ is H.

In one illustration, the compounds of formula (II) are the compounds wherein $R_{B2}$ is H. In another illustration, the compounds of formula (II) are the compounds wherein $R_{B2}$ is unsubstituted $C_1$-$C_6$ straight chain alkyl. In a further illustration, the compounds of formula (II) are the compounds wherein $R_{B2}$ is unsubstituted methyl. In another illustration, the compounds of formula (II) are the compounds wherein $R_{B2}$ is unsubstituted $C_3$-$C_6$ branched alkyl. In another illustration, the compounds of formula (II) are the compounds wherein $R_{B2}$ is unsubstituted phenyl.

In one illustration, the compounds of formula (II) are the compounds wherein $R_{B1}$ is unsubstituted $C_1$-$C_8$ straight chain or $C_3$-$C_8$ branched alkyl, or $C_1$-$C_8$ straight chain or $C_3$-$C_8$ branched alkyl substituted with one or more substituents independently selected from hydroxyl, F, Cl,
unsubstituted $C_1$-$C_6$ alkoxy, $C_1$-$C_6$ alkoxy substituted with halogen or phenyl, unsubstituted phenyl, phenyl substituted with one or more substituents independently selected from F, Cl, and unsubstituted $C_1$-$C_6$ alkoxy, unsubstituted phenoxy, and phenoxy substituted with one or more substituents independently selected from F, Cl, unsubstituted $C_1$-$C_6$ alkyl, $C_1$-$C_6$ alkyl substituted with F or Cl, unsubstituted $C_1$-$C_6$ alkoxy, and nitro.

In another illustration, the compounds of formula (II) are the compounds wherein $R_{B1}$ is unsubstituted $C_1$-$C_6$ alkoxy, or $C_1$-$C_6$ alkoxy substituted with F or Cl.

In another illustration, the compounds of formula (II) are the compounds wherein $R_{B1}$ is unsubstituted phenyl, or phenyl substituted with one or more substituents independently selected from F, Cl, unsubstituted $C_1$-$C_6$ alkoxy, and nitro.

In another illustration, the compounds of formula (II) are the compounds wherein $R_{B1}$ is unsubstituted phenoxy, or phenoxy substituted with one or more substituents independently selected from F, Cl, unsubstituted $C_1$-$C_6$ alkoxy, and nitro.

In another illustration, the compounds of formula (II) are the compounds wherein $R_{B1}$ is unsubstituted $C_3$-$C_6$ cycloalkyl.

In another illustration, the compounds of formula (II) are the compounds wherein $R_{B1}$ is unsubstituted $C_2$-$C_8$ straight chain alkenyl.

In a further illustration, the compounds of formula (II) are the compounds wherein $R_{B3}$ is H; $R_{B2}$ is H; and $R_{B1}$ is one of the substituents described above.

In a further illustration, the compounds of formula (II) are the compounds wherein $R_{B3}$ is H; $R_{B2}$ is unsubstituted $C_1$-$C_6$ straight chain alkyl or unsubstituted phenyl; and $R_{B1}$ is unsubstituted methyl.

Specific examples of the compounds of formula (II) include the compounds in Table 2. Yet further the compounds of formula (II) are (S)-3-(aminomethyl)-5-methylhexanoic acid and (R)-3-(aminomethyl)-5-methylhexanoic acid, or pharmaceutically acceptable salts or racemic mixtures thereof.

In a third aspect, compounds that can be used in the invention include Compound (11):

(11)

or a pharmaceutically acceptable salt thereof.

In a fourth aspect, compounds that can be used in the invention include a compound of one of formulae (IIIa)-(IIIf):

(IIIa)

(IIIb)

(IIIc)

(IIId)

(IIIe)

(IIIf)

or a pharmaceutically acceptable salt thereof, wherein:

each $R_0$ is independently halogen, $CF_2H$, $CF_3$, $R_{b2}$, $OR_{b1}$, $COOR_{b1}$, $CON(R_{b1})_2$, $N(R_{b2})_2$, $NR_{b1}COR_{b1}$, $NR_{b1}COOR_{b2}$, $NR_{b1}CON(R_{b1})_2$, $NR_{b1}SO_2R_{b2}$, $SO_2R_{b2}$, $SO_2N(R_{b1})_2$, unsubstituted phenyl, or phenyl substituted with 1-3 substituents independently selected from F, Cl, $CF_2H$, $CF_3$, $OR_{b1}$, and $R_{b2}$, or two such substituents, together with the carbon atoms of the phenyl rings to which they are attached, form a five- or six-membered ring having a structure selected from wherein "*" denotes the positions of the carbon atoms to which the substituents are attached on the phenyl ring, or alternatively, when attached to adjacent atoms, any two $R_0$, together with the atoms to which they are attached, form a five- or six-membered ring having a structure selected from

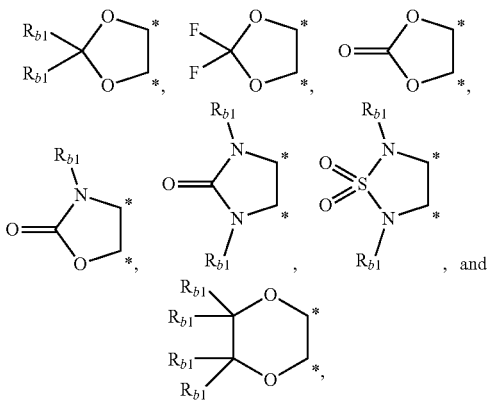

wherein "*" denotes the positions of the atoms to which the two $R_0$ are attached, or each $R_{b1}$ is independently H, $C_1$-$C_6$ straight chain or $C_3$-$C_6$ branched alkyl, or $C_3$-$C_6$ cycloalkyl;

each $R_{b2}$ is independently $C_1$-$C_6$ straight chain or $C_3$-$C_6$ branched alkyl, or $C_3$-$C_6$ cycloalkyl;

each $R_{b3}$ is independently H, $C_1$-$C_6$ straight chain or $C_3$-$C_6$ branched alkyl, or halogen;

each $Q_b$ is independently H, $C_1$-$C_6$ straight chain or $C_3$-$C_6$ branched alkyl, or $C_1$-$C_6$ straight chain or $C_3$-$C_6$ branched alkyl substituted with 1-6 F, or both $Q_b$, together with the carbon atom to which they are attached, form a $C_3$-$C_6$ carbocycle or a saturated heterocycle selected from

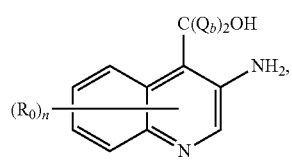

wherein "*" denotes the position of the carbon atom to which both $Q_b$ are attached, wherein the carbocycle or the heterocycle is optionally substituted with one or more $R_{b3}$; and n is 0, 1, 2, or 3.

One class of this aspect are the compounds of formula (IIIa):

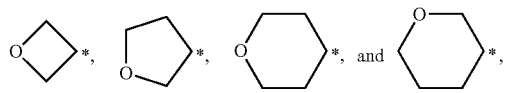

(IIIa)

or a pharmaceutically acceptable salt thereof.

Further illustrating this exemplification are the compounds of formula (IIIa), wherein n is 0, 1 or 2. Yet a further illustration includes the compounds of formula (IIIa) wherein $R_0$, which can be attached to either ring of formula (IIIa), is F or Cl. Further defining formula (IIIa) are the compounds wherein $Q_b$ is selected from $C_1$-$C_6$ straight chain or $C_3$-$C_6$ branched alkyl, or wherein both $Q_b$, together with the carbon atom to which they are attached, form a ring selected from

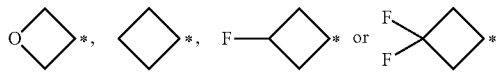

wherein "*" denotes the position of the carbon atom to which both $Q_b$ are attached.

Specific examples of formula (IIIa) include Compounds (1)-(8) and pharmaceutically acceptable salts thereof:

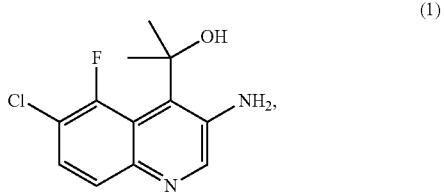

(1)

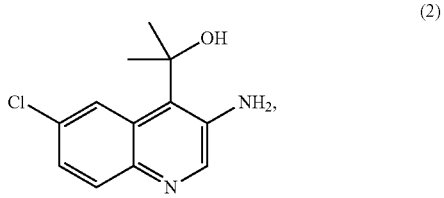

(2)

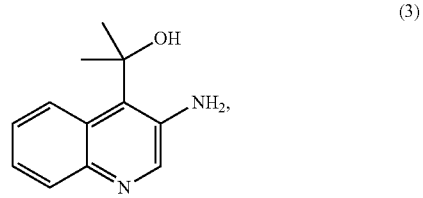

(3)

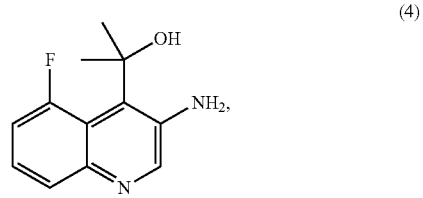

(4)

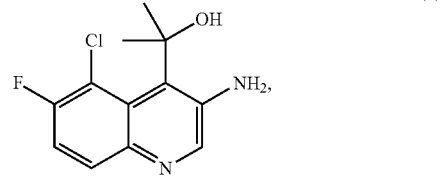

(5)

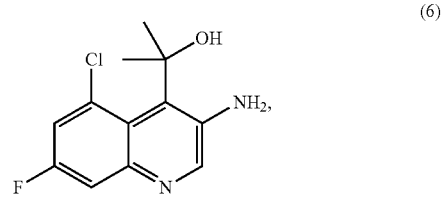

(6)

-continued

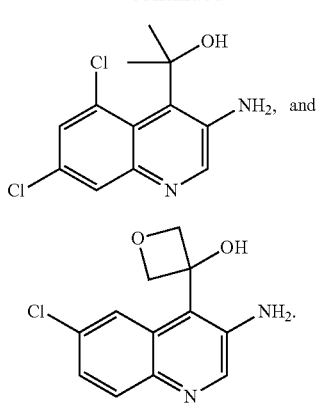

Preferably, the compound is Compound (1) or (2).

Another class of this aspect are the compounds of formula (IIIf):

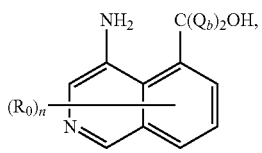

or a pharmaceutically acceptable salt thereof.

Specific examples of formula (IIIf) include Compound (10) and pharmaceutically acceptable salts thereof:

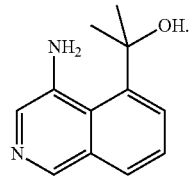

Examples of the compounds of this aspect include a compound of any one of formulae (IIIa)-(IIIf), wherein n is 0, 1 or 2. For example, n is 1.

Examples of the compounds of this aspect include a compound of any one of formulae wherein each $R_0$ is independently selected from F, Cl, Br, $CF_2H$, $CF_3$, $R_{b2}$, $OR_{b1}$, $COOR_{b1}$, $CON(R_{b1})_2$, $N(R_{b2})_2$, $NR_{b1}COR_{b1}$, $NR_{b1}COOR_{b2}$, $NR_{b1}CON(R_{b1})_2$, $NR_{b1}SO_2R_{b2}$, $SO_2R_{b2}$, $SO_2N(R_{b1})_2$, unsubstituted phenyl, and phenyl substituted with 1-3 substituents as listed above. For example, each $R_0$ is independently selected from F, Cl, Br, $CF_2H$, $CF_3$ and $R_{b2}$. For example, each $R_0$ is independently selected from F, Cl and Br. For example, n is 0, 1 or 2 and each $R_0$ is independently selected from F, Cl, Br, $CF_2H$, $CF_3$, $R_{b2}$, $OR_{b1}$, $COOR_{b1}$, $CON(R_{b1})_2$, $N(R_{b2})_2$, $NR_{b1}COR_{b1}$, $NR_{b1}COOR_{b2}$, $NR_{b1}CON(R_{b1})_2$, $NR_{b1}SO_2R_{b2}$, $SO_2R_{b2}$, $SO_2N(R_{b1})_2$, unsubstituted phenyl, and phenyl substituted with 1-3 substituents as listed above. For example, n is 0, 1 or 2 and each $R_0$ is independently selected from F, Cl, Br, $CF_2H$, $CF_3$ and $R_{b2}$. For example, n is 0, 1 or 2 and each $R_0$ is independently selected from F, Cl and Br.

Examples of the compounds of this aspect include a compound of any one of formulae (IIIa)-(IIIf), wherein at least one $Q_b$ is $C_1$-$C_6$ straight chain alkyl. For example, in certain compounds, at least one $Q_b$ is methyl, ethyl or propyl. For example, each $Q_b$ is methyl. For example, n is 0, 1 or 2 and at least one $Q_b$ is $C_1$-$C_6$ straight chain alkyl (e.g., methyl, ethyl and propyl). For example, n is 0, 1 or 2 and each $Q_b$ is methyl. In another example, at least one $Q_b$ is $C_1$-$C_6$ straight chain alkyl substituted with 1-6 F. For example, in certain compounds, at least one $Q_b$ is methyl, ethyl or propyl substituted with 1-6 F. For example, at least one $Q_b$ is $CH_2F$, $CHF_2$, or $CF_3$. For example, each $Q_b$ is $CF_3$. For example, n is 0, 1 or 2 and at least one $Q_b$ is $C_1$-$C_6$ straight chain alkyl substituted with 1-6 F (e.g., methyl, ethyl or propyl substituted with 1-6 F). For example, n is 0, 1 or 2 and each $Q_b$ is $CF_3$.

Examples of the compounds of this aspect include a compound of any one of formula (IIIa)-(IIIf), wherein both $Q_b$, together with the carbon atom to which they are attached, form a $C_3$-$C_6$ carbocycle or a saturated heterocycle, each of which is optionally substituted with one or more $R_{b3}$, wherein each $R_{b3}$ is independently methyl, ethyl, propyl, fluorine, chlorine or bromine (e.g., each $R_{b3}$ is independently methyl or fluorine). For example, both $Q_b$, together with the carbon atom to which they are attached, form

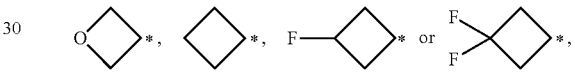

wherein "*" denotes the position of the carbon atom to which the two $Q_b$ are attached.

Examples of the compounds of this aspect include a compound of any one of formula (IIIa)-(IIIf), wherein each $R_{b1}$ is independently H or $C_1$-$C_6$ straight chain alkyl. For example, each $R_{b1}$ is independently H, methyl, ethyl or propyl.

Examples of the compounds of this aspect include a compound of any one of formula wherein each $R_{b2}$ is independently methyl, ethyl or propyl.

In a fifth aspect, compounds that can be used in the invention include a compound of formula (IV):

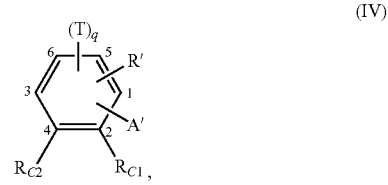

or a pharmaceutically acceptable salt thereof, wherein:

A' and R', together with the two adjacent carbon atoms to which they are attached, form a five-membered heteroaryl ring containing one nitrogen atom and one oxygen atom, wherein the heteroaryl ring is substituted with $R_{C'}$, wherein "1", "2", "3", "4", "5", and "6" denote the points of attachment of the heteroaryl ring to the phenyl ring, provided that when the heteroaryl ring is

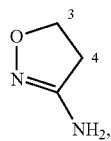

then $R_{C1}$ is $C(Q_C)_2OH$, $R_{C2}$ is absent, and $R_C'$ is absent, and that when the heteroaryl ring is

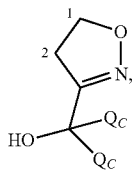

then $R_{C1}$ is absent, $R_{C2}$ is $NH_2$, and $R_C'$ is absent;

$R_{C1}$ is $C(Q_C)_2OH$, or $R_{C1}$ is absent when A' and R', together with the two adjacent carbon atoms to which they are attached, form

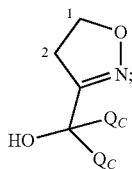

$R_{C2}$ is $NH_2$, or $R_{C2}$ is absent when A' and R', together with the two adjacent carbon atoms to which they are attached, form

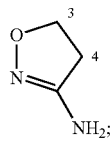

each $Q_C$ is independently $C_1$-$C_6$ alkyl or $C_3$-$C_6$ cycloalkyl, or two $Q_C$, together with the carbon atom to which they are attached, form a $C_3$-$C_6$ carbocyclic ring or a saturated heterocycle selected from

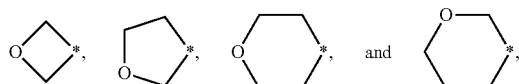

wherein "*" denotes the position of the carbon atom to which the two $Q_C$ are attached;

$R_C'$ is $C_1$-$C_{10}$ alkyl, $C_1$-$C_{10}$ alkyl substituted with $C_3$-$C_6$ cycloalkyl, $C_3$-$C_6$ cycloalkyl, aryl, aryl substituted with $C_1$-$C_6$ alkyl, or $C_1$-$C_6$ alkoxy, or $R_C'$ is absent when A' and R', together with the two adjacent carbon atoms to which they are attached, form

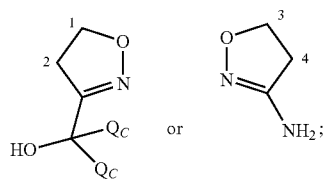

q is 0, 1, or 2, provided that when $R_C'$ is phenyl, q is not 0; and each T is independently halogen, $C_1$-$C_{10}$ alkyl, $C_1$-$C_{10}$ alkyl substituted with $C_3$-$C_6$ cycloalkyl, $C_3$-$C_6$ cycloalkyl, or cyano.

In one example, A' and R', together with the two adjacent carbon atoms to which they are attached, form a five-membered heteroaryl ring containing one nitrogen atom and one oxygen atom, wherein the heteroaryl ring is substituted with $R_C'$. In one example, $R_C'$ is $C_3$-$C_6$ cycloalkyl (e.g., cyclopropyl and cyclobutyl), aryl (e.g., phenyl), or aryl (e.g., phenyl) substituted with $C_1$-$C_6$ alkyl (e.g., methyl, ethyl, propyl, and butyl). In a further example, $R_C'$ is phenyl, phenyl substituted with methyl, cyclopropyl, or cyclobutyl. In another example, $R_C'$ is $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, $R_C'$ is $C_1$-$C_6$ alkoxy (e.g., methoxy, ethoxy, and propoxy).

In one example, $R_{C1}$ is $C(Q_C)_2OH$ and $R_{C2}$ is $NH_2$. In one example, each $Q_C$ is independently $C_1$-$C_6$ alkyl (e.g., methyl, ethyl, propyl, and butyl). In a further example, each $Q_C$ is methyl.

In one example, A' and R', together with the two adjacent carbon atoms to which they are attached, form

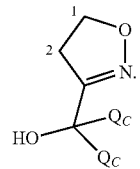

In another example, A' and R', together with the two adjacent carbon atoms to which they are attached, form

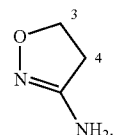

In one example, each $Q_C$ is independently $C_1$-$C_6$ alkyl (e.g., methyl, ethyl, propyl, and butyl). In a further example, each $Q_C$ is methyl.

In one example, q is 1 or 2. In a further example, q is 1. In one example, each T is independently halogen (e.g., F, Cl, and Br). In a further example, each T is independently F or Cl. In another example, each T is independently $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, each T is independently $C_3$-$C_6$ cycloalkyl (e.g., cyclopropyl and cyclobutyl).

In one example, A' and R', together with the two adjacent carbon atoms to which they are attached, form a five-membered heteroaryl ring containing one nitrogen atom and one oxygen atom, wherein the heteroaryl ring is substituted with $R_C$; $R_C'$ is aryl, aryl substituted with methyl, or cyclopropyl; q is 1; T is Cl; $R_{C1}$ is $C(Q_C)_2OH$; $R_{C2}$ is $NH_2$; and each $Q_C$ is methyl.

In a further example of formula (IV), A' and R', together with the two adjacent carbon atoms to which they are attached, form

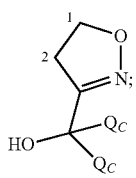

$R_{C2}$ is $NH_2$; each $Q_C$ is methyl; and q is 0. In another further example of formula (IV), A' and R', together with the two adjacent carbon atoms to which they are attached, form

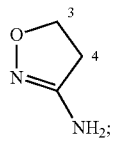

$R_{C1}$ is $C(Q_C)_2OH$; each $Q_C$ is methyl; and q is 0.

In one class of this aspect, the compounds of formula (IV) are the compounds of formula (IVa):

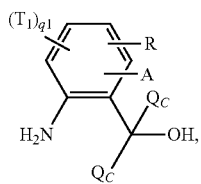

(IVa)

or a pharmaceutically acceptable salt thereof, wherein:

A and R, together with the two adjacent carbon atoms to which they are attached, form a five-membered heteroaryl ring containing one nitrogen atom and one oxygen atom, wherein the heteroaryl ring is substituted with $R_C$;

$R_C$ is $C_1$-$C_{10}$ alkyl, $C_1$-$C_{10}$ alkyl substituted with $C_3$-$C_6$ cycloalkyl, $C_3$-$C_6$ cycloalkyl, aryl, aryl substituted with $C_1$-$C_6$ alkyl, or $C_1$-$C_6$ alkoxy;

$q_1$ is 1 or 2;

each $T_1$ is independently halogen, $C_1$-$C_{10}$ alkyl, $C_1$-$C_{10}$ alkyl substituted with $C_3$-$C_6$ cycloalkyl, $C_3$-$C_6$ cycloalkyl, or cyano; and each $Q_C$ is independently $C_1$-$C_6$ alkyl or $C_3$-$C_6$ cycloalkyl, or two $Q_C$, together with the carbon atom to which they are attached, form a $C_3$-$C_6$ carbocyclic ring or a saturated heterocycle selected from

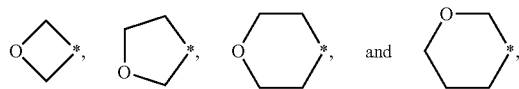

wherein "*" denotes the position of the carbon atom to which the two $Q_C$ are attached.

In one example, $R_C$ is $C_3$-$C_6$ cycloalkyl (e.g., cyclopropyl and cyclobutyl), aryl (e.g., phenyl), or aryl (e.g., phenyl) substituted with $C_1$-$C_6$ alkyl (e.g., methyl, ethyl, propyl, and butyl). In a further example, $R_C$ is phenyl, phenyl substituted with methyl, cyclopropyl, or cyclobutyl. In yet another example, $R_C$ is $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, $R_C$ is $C_1$-$C_6$ alkoxy (e.g., methoxy, ethoxy, and propoxy).

In one example, each $Q_C$ is independently $C_1$-$C_6$ alkyl (e.g., methyl, ethyl, propyl, and butyl). In a further example, each $Q_C$ is methyl.

In one example, $q_1$ is 1.

In one example, each $T_1$ is independently halogen (e.g., F, Cl, and Br). In a further example, each $T_1$ is independently F or Cl. In another example, each $T_1$ is independently $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, each $T_1$ is independently $C_3$-$C_6$ cycloalkyl (e.g., cyclopropyl and cyclobutyl).

In a further example of formula (IVa), $R_C$ is aryl, aryl substituted with methyl, or cyclopropyl; $q_1$ is 1; $T_1$ is Cl; and each $Q_C$ is methyl.

One illustration of this class are the compounds of formula (IVa1):

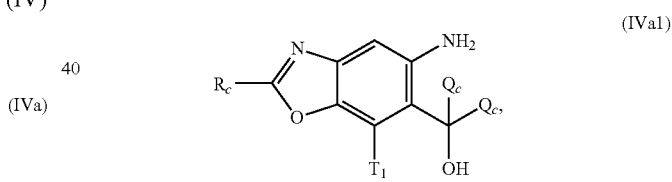

(IVa1)

or a pharmaceutically acceptable salt thereof, wherein:

$R_C$ is $C_1$-$C_{10}$ alkyl, $C_1$-$C_{10}$ alkyl substituted with $C_3$-$C_6$ cycloalkyl, $C_3$-$C_6$ cycloalkyl, aryl, aryl substituted with $C_2$-$C_6$ alkyl, or $C_1$-$C_6$ alkoxy;

$T_1$ is F, Cl, $C_1$-$C_{10}$ alkyl, $C_1$-$C_{10}$ alkyl substituted with $C_3$-$C_6$ cycloalkyl, $C_3$-$C_6$ cycloalkyl, or cyano; and each $Q_C$ is independently $C_1$-$C_6$ alkyl or $C_3$-$C_6$ cycloalkyl, or two $Q_C$, together with the carbon atom to which they are attached, form a $C_3$-$C_6$ carbocyclic ring or a saturated heterocycle selected from

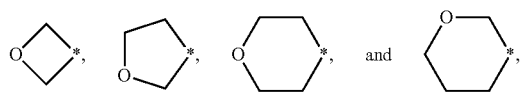

wherein "*" denotes the position of the carbon atom to which the two $Q_C$ are attached.

In one example, $R_C$ is $C_3$-$C_6$ cycloalkyl (e.g., cyclopropyl and cyclobutyl), aryl (e.g., phenyl), or aryl (e.g., phenyl) substituted with $C_1$-$C_6$ alkyl (e.g., methyl, ethyl, propyl, and butyl). In a further embodiment, $R_C$ is phenyl, phenyl substituted with methyl, cyclopropyl, or cyclobutyl. In a further embodiment, $R_C$ is phenyl or phenyl substituted with methyl. In another example, $R_C$ is $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, $R_C$ is $C_1$-$C_6$ alkoxy (e.g., methoxy, ethoxy, and propoxy).

In one example, each $Q_C$ is independently $C_1$-$C_6$ alkyl (e.g., methyl, ethyl, propyl, and butyl). In a further example, each $Q_C$ is methyl.

In one example, $T_1$ is Cl. In another example, $T_1$ is $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, $T_1$ is independently $C_3$-$C_6$ cycloalkyl (e.g., cyclopropyl and cyclobutyl).

In a further example of formula (IVa1), $R_C$ is aryl or aryl substituted with methyl; $T_1$ is Cl; and each $Q_C$ is methyl.

Further defining the compounds of formula (IVa1) are the compounds wherein: $R_C$ is $C_3$-$C_6$ cycloalkyl, aryl, or aryl substituted with $C_1$-$C_6$ alkyl;
$T_1$ is F, Cl, methyl, cyclopropyl, cyclobutyl, or cyano; and each $Q_C$ is independently $C_1$-$C_6$ alkyl or $C_3$-$C_6$ cycloalkyl, or a pharmaceutically acceptable salt thereof.

In one subclass are the compounds wherein:
$T_1$ is F, Cl, methyl, or cyano; and
$Q_C$ is methyl,
or a pharmaceutically acceptable salt thereof.

Further illustrating the compounds of formula (IVa1) are compounds 12 and 13:

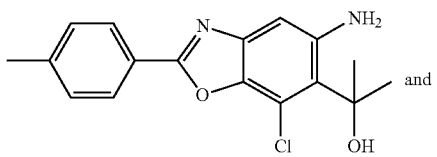

and

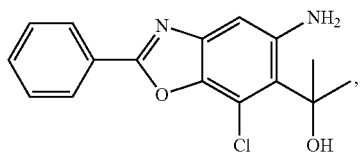

or a pharmaceutically acceptable salt thereof.

Another illustration of this class are the compounds of formula (IVa2) or (IVa3):

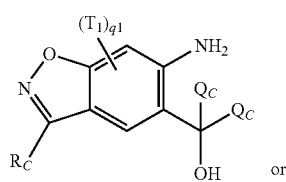

(IVa2)

or

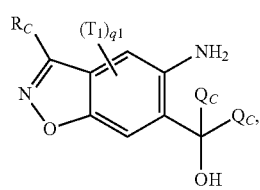

(IVa3)

or a pharmaceutically acceptable salt thereof, wherein:

$R_C$ is $C_1$-$C_{10}$ alkyl, $C_1$-$C_{10}$ alkyl substituted with $C_3$-$C_6$ cycloalkyl, $C_3$-$C_6$ cycloalkyl, aryl, aryl substituted with $C_1$-$C_6$ alkyl, or $C_1$-$C_6$ alkoxy;

$q_1$ is 1 or 2;

each $T_1$ is independently F, Cl, $C_1$-$C_{10}$ alkyl, $C_1$-$C_{10}$ alkyl substituted with $C_3$-$C_6$ cycloalkyl, $C_3$-$C_6$ cycloalkyl, or cyano; and each $Q_C$ is independently $C_1$-$C_6$ alkyl or $C_3$-$C_6$ cycloalkyl, or two $Q_C$, together with the carbon atom to which they are attached, form a $C_3$-$C_6$ carbocyclic ring or a saturated heterocycle selected from

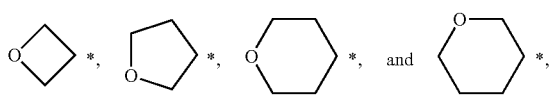

wherein "*" denotes the position of the carbon atom to which the two $Q_C$ are attached.

In one example, $R_C$ is $C_3$-$C_6$ cycloalkyl (e.g., cyclopropyl and cyclobutyl), aryl (e.g., phenyl), or aryl (e.g., phenyl) substituted with $C_1$-$C_6$ alkyl (e.g., methyl, ethyl, propyl, and butyl). In a further embodiment, $R_C$ is phenyl, phenyl substituted with methyl, cyclopropyl, or cyclobutyl. In a further example, $R_C$ is cyclopropyl or cyclobutyl. In another example, $R_C$ is $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, $R_C$ is $C_1$-$C_6$ alkoxy (e.g., methoxy, ethoxy, and propoxy).

In one example, each $Q_C$ is independently $C_1$-$C_6$ alkyl (e.g., methyl, ethyl, propyl, and butyl). In a further example, each $Q_C$ is methyl.

In one example, $q_1$ is 1.

In one example, each $T_1$ is Cl. In another example, each $T_1$ is independently $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, each $T_1$ is independently $C_3$-$C_6$ cycloalkyl (e.g., cyclopropyl and cyclobutyl).

In a further example of formula (IVa2) or (IVa3), $R_C$ is cyclopropyl; $q_1$ is 1; $T_1$ is Cl; and each $Q_C$ is methyl.

Further defining the compounds of formulae (IVa2) and (IVa3) are the compounds wherein:

$R_C$ is $C_3$-$C_6$ cycloalkyl, aryl, or aryl substituted with $C_1$-$C_6$ alkyl;

$q_1$ is 1;

$T_1$ is F, Cl, methyl, cyclopropyl, cyclobutyl, or cyano; and each $Q_C$ is independently $C_1$-$C_6$ alkyl or $C_1$-$C_6$ cycloalkyl, or a pharmaceutically acceptable salt thereof.

Further illustrating the compounds of formula (IVa2) or (IVa3) are the compounds of formula (IVa2A) or (IVa3A):

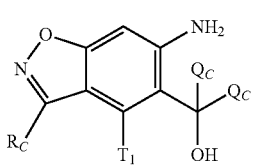

(IVa2A)

or

-continued

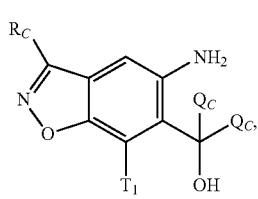
(IVa3A)

or a pharmaceutically acceptable salt thereof, wherein $R_C$, $T_1$, and $Q_C$ are defined above in formula (IVa2) or (IVa3).

Further defining the compounds of formula (IVa2A) or (IVa3A) are the compounds wherein:

$R_C$ is $C_3$-$C_6$ cycloalkyl, aryl, or aryl substituted with $C_1$-$C_6$ alkyl;

$T_1$ is F, Cl, methyl, cyclobutyl, cyclopropyl, or cyano; and each $Q_C$ is independently $C_1$-$C_6$ alkyl or $C_1$-$C_6$ cycloalkyl, or a pharmaceutically acceptable salt thereof.

For example, $R_C$ is cyclopropyl or cyclobutyl; $T_1$ is F or Cl; and each $Q_C$ is independently $C_1$-$C_6$ alkyl.

Further illustrating the compounds of formula (IVa2) or (IVa3) are compounds 14 and 15:

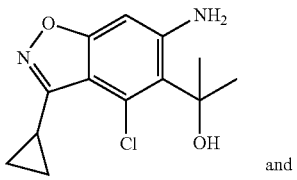
(14)

and

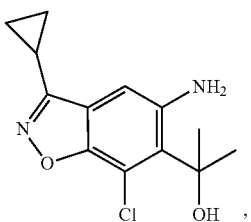
(15)

or a pharmaceutically acceptable salt thereof.

A third illustration of this class are the compounds of formula (IVa4):

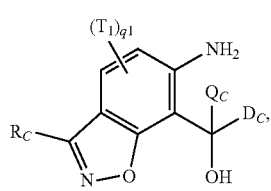
(IVa4)

or a pharmaceutically acceptable salt thereof, wherein:

$R_C$ is $C_1$-$C_{10}$ alkyl, $C_1$-$C_{10}$ alkyl substituted with $C_3$-$C_6$ cycloalkyl, $C_3$-$C_6$ cycloalkyl, aryl, aryl substituted with $C_1$-$C_6$ alkyl, or $C_1$-$C_6$ alkoxy;

$q_1$ is 1 or 2;

each $T_1$ is independently F, Cl, $C_1$-$C_{10}$ alkyl, $C_3$-$C_6$ cycloalkyl, $C_1$-$C_{10}$ alkyl substituted with $C_3$-$C_6$ cycloalkyl, or cyano; and each $Q_C$ is independently $C_1$-$C_6$ alkyl or $C_3$-$C_6$ cycloalkyl, or two $Q_C$, together with the carbon atom to which they are attached, form a $C_3$-$C_6$ carbocyclic ring or a saturated heterocycle selected from

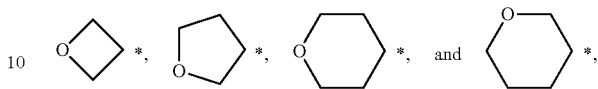

wherein "*" denotes the position of the carbon atom to which the two $Q_C$ are attached.

In one example, $R_C$ is $C_3$-$C_6$ cycloalkyl (e.g., cyclopropyl and cyclobutyl), aryl (e.g., phenyl), or aryl (e.g., phenyl) substituted with $C_1$-$C_6$ alkyl (e.g., methyl, ethyl, propyl, and butyl). In a further embodiment, $R_C$ is phenyl, phenyl substituted with methyl, cyclopropyl, or cyclobutyl. In a further embodiment, $R_C$ is cyclopropyl or cyclobutyl. In another example, $R_C$ is $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, $R_C$ is $C_1$-$C_6$ alkoxy (e.g., methoxy, ethoxy, and propoxy).

In one example, each $Q_C$ is independently $C_1$-$C_6$ alkyl (e.g., methyl, ethyl, propyl, and butyl). In a further example, each $Q_C$ is methyl.

In one example, $q_1$ is 1.

In one example, each $T_1$ is Cl. In another example, each $T_1$ is independently $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, each $T_1$ is independently $C_3$-$C_6$ cycloalkyl (e.g., cyclopropyl and cyclobutyl).

In a further example of formula (IVa4), $R_C$ is cyclopropyl; $q_1$ is 1; $T_1$ is Cl; and each $Q_C$ is methyl.

Further defining the compounds of formula (IVa4) are the compounds wherein:

$R_C$ is $C_3$-$C_6$ cycloalkyl, aryl, or aryl substituted with $C_1$-$C_6$ alkyl;

$q_1$ is 1;

$T_1$ is F, Cl, methyl, cyclopropyl, cyclobutyl, or cyano; and each $Q_C$ is independently $C_1$-$C_6$ alkyl or $C_1$-$C_6$ cycloalkyl, or a pharmaceutically acceptable salt thereof.

Further illustrating this class is compound 16:

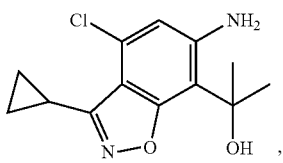
(16)

or a pharmaceutically acceptable salt thereof.

In a second class of this aspect, the compounds of formula (IV) are the compounds of formula (IVb):

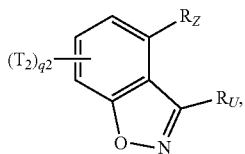

(IVb)

or a pharmaceutically acceptable salt thereof, wherein:
one of $R_U$ and $R_Z$ is $C(Q_C)_2OH$, and the other is $NH_2$;
each $Q_C$ is independently $C_1$-$C_6$ alkyl or $C_3$-$C_6$ cycloalkyl, or two $Q_C$, together with the carbon atom to which they are attached, form a $C_3$-$C_6$ carbocyclic ring or a saturated heterocycle selected from

wherein "*" denotes the position of the carbon atom to which the two $Q_C$ are attached;
$q_2$ is 0, 1, or 2; and
each $T_2$ is independently halogen, $C_1$-$C_{10}$ alkyl, $C_1$-$C_{10}$ alkyl substituted with $C_3$-$C_6$ cycloalkyl, $C_3$-$C_6$ cycloalkyl, or cyano.

In one example, each $Q_C$ is independently $C_1$-$C_6$ alkyl (e.g., methyl, ethyl, propyl, and butyl). In a further example, each $Q_C$ is methyl.

In one example, $q_2$ is 0 or 1. In a further example, $q_2$ is 0.

In one example, each $T_2$ is independently halogen (e.g., F, Cl, and Br). In a further example, each $T_2$ is independently F or Cl. In another example, each $T_2$ is independently $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, each $T_2$ is independently $C_3$-$C_6$ cycloalkyl (e.g., cyclopropyl and cyclobutyl).

In a further example of formula (IVb), $q_2$ is 0; and each $Q_C$ is methyl.

One illustration of this class are the compounds of formula (IVb1) or (IVb2):

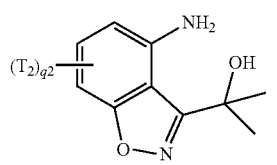

(IVb1)

or

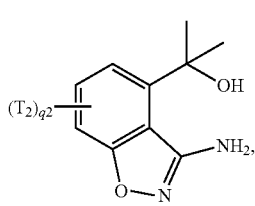

(IVb2)

or a pharmaceutically acceptable salt thereof, wherein:
$q_2$ is 0, 1, or 2; and
each $T_2$ is independently F, Cl, $C_1$-$C_{10}$ alkyl, $C_1$-$C_{10}$ alkyl substituted with $C_3$-$C_6$ cycloalkyl, $C_3$-$C_6$ cycloalkyl, or cyano.

In one example, $q_2$ is 0 or 1. In a further example, $q_2$ is 0.

In one example, each $T_2$ is Cl. In another example, each $T_2$ is independently $C_1$-$C_{10}$ alkyl (e.g., methyl, ethyl, propyl, and butyl) or $C_1$-$C_{10}$ alkyl (e.g., methyl, ethyl, propyl, and butyl) substituted with $C_3$-$C_6$ cycloalkyl (e.g., cyclopropyl and cyclobutyl). In another example, each $T_2$ is independently $C_3$-$C_6$ cycloalkyl (e.g., cyclopropyl and cyclobutyl).

Further illustrating the compounds of formula (IVb1) or (IVb2) are compounds 17 and 18:

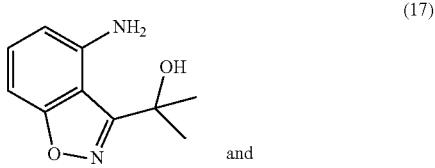

and

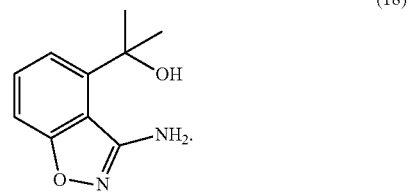

Compounds that can be used in the invention include the compounds listed in Tables 1 and 2.

TABLE 1

| Compound # | |
|---|---|
| 1 | 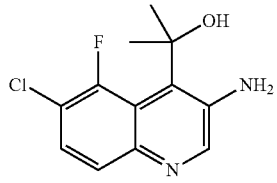 [SMILES: CC(C)(O)c1c(N)cnc2ccc(Cl)c(F)c12] |
| 2 | 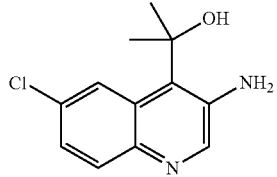 [SMILES: CC(C)(O)c1c(N)cnc2ccc(Cl)cc12] |
| 3 | 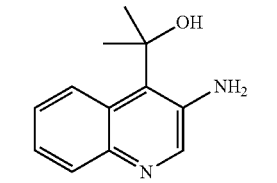 |
| 4 | 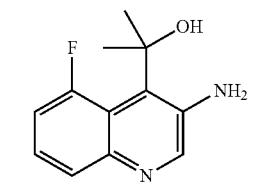 [SMILES: CC(C)(O)c1c(N)cnc2cccc(F)c12] |

TABLE 1-continued

| Compound # | |
|---|---|
| 5 | (structure: 5-chloro-6-fluoro-4-(2-hydroxypropan-2-yl)quinolin-3-amine) |
| 6 | (structure: 5-chloro-7-fluoro-4-(2-hydroxypropan-2-yl)quinolin-3-amine) |
| 7 | (structure: 5,7-dichloro-4-(2-hydroxypropan-2-yl)quinolin-3-amine) |
| 8 | (structure: 6-chloro-4-(3-hydroxyoxetan-3-yl)quinolin-3-amine) |
| 9 | (structure: 6-chloro-2-(2-hydroxypropan-2-yl)quinolin-3-amine) |
| 10 | (structure: 5-(2-hydroxypropan-2-yl)isoquinolin-1-amine) |
| 11 | (structure: 3-amino-1-(3-(cyclohexylmethoxy)phenyl)propan-1-ol) |
| 12 | (structure: 7-chloro-6-(2-hydroxypropan-2-yl)-2-(p-tolyl)benzo[d]oxazol-5-amine) |
| 13 | (structure: 7-chloro-6-(2-hydroxypropan-2-yl)-2-phenylbenzo[d]oxazol-5-amine) |
| 14 | (structure: 4-chloro-3-cyclopropyl-5-(2-hydroxypropan-2-yl)benzo[d]isoxazol-6-amine) |
| 15 | (structure: 7-chloro-3-cyclopropyl-6-(2-hydroxypropan-2-yl)benzo[d]isoxazol-5-amine) |
| 16 | (structure: 4-chloro-3-cyclopropyl-7-(2-hydroxypropan-2-yl)benzo[c]isoxazol-6-amine) |
| 17 | (structure: 3-(2-hydroxypropan-2-yl)benzo[d]isoxazol-4-amine) |
| 18 | (structure: 4-(2-hydroxypropan-2-yl)benzo[d]isoxazol-3-amine) |

TABLE 2

3-aminomethyl-5-methylhexanoic acid, 3-aminomethyl-5-methylheptanoic acid, 3-aminomethyl-5-methyl-octanoic acid, 3-aminomethyl-5-methyl-nonanoic acid, 3-aminomethyl-5-methyl-decanoic acid, 3-aminomethyl-5-methyl-undecanoic acid, 3-aminomethyl-5-methyl-dodecanoic acid, 3-aminomethyl-5-methyl-tridecanoic acid, 3-aminomethyl-5-cyclopropyl-hexanoic acid, 3-aminomethyl-5-cyclobutyl-hexanoic acid, 3-aminomethyl-5-cyclopentyl-hexanoic acid, 3-aminomethyl-5-cyclohexyl-hexanoic acid, 3-aminomethyl-5-trifluoromethyl-hexanoic acid, 3-aminomethyl-5-phenyl-hexanoic acid, 3-aminomethyl-5-(2-chlorophenyl)-hexanoic acid, 3-aminomethyl-5-(3-chlorophenyl)-hexanoic acid, 3-aminomethyl-5-(4-chlorophenyl)-hexanoic acid, 3-aminomethyl-5-(2-methoxyphenyl)-hexanoic acid, 3-aminomethyl-5-(3-methoxyphenyl)-hexanoic acid, 3-

TABLE 2-continued aminomethyl-5-(4-methoxyphenyl)-hexanoic acid, 3-aminomethyl-5-benzyl-hexanoic acid, (S)-3-aminomethyl-5-methylhexanoic acid, (R)-3-aminomethyl-5-methylhexanoic acid, (3R,4S)-3-aminomethyl-4,5-dimethyl-hexanoic acid, 3-aminomethyl-4,5-dimethyl-hexanoic acid, (3R,4S)-3-aminomethyl-4,5-dimethyl-hexanoic acid MP; (3S,4S)-3-aminomethyl-4,5-dimethyl-hexanoic acid, (3R,4R)-3-aminomethyl-4,5-dimethyl-hexanoic acid MP; 3-aminomethyl-4-isopropyl-hexanoic acid, 3-aminomethyl-4-isopropyl-heptanoic acid, 3-aminomethyl-4-isopropyl-octanoic acid, 3-aminomethyl-4-isopropyl-nonanoic acid, 3-aminomethyl-4-isopropyl-decanoic acid, 3-aminomethyl-4-phenyl-5-methyl-hexanoic acid, (3S,5S)-3-aminomethyl-5-methoxy-hexanoic acid, (3S,5S)-3-aminomethyl-5-ethoxy-hexanoic acid, (3S,5S)-3-aminomethyl-5-propoxy-hexanoic acid, (3S,5S)-3-aminomethyl-5-isopropoxy-hexanoic acid, (3S,5S)-3-aminomethyl-5-tert-butoxy-hexanoic acid, (3S,5S)-3-aminomethyl-5-fluoromethoxy-hexanoic acid, (3S,5S)-3-aminomethyl-5-(2-fluoro-ethoxy)-hexanoic acid, (3S,5S)-3-aminomethyl-5-(3,3,3-trifluoro-propoxy)-hexanoic acid, (3S,5S)-3-aminomethyl-5-phenoxy-hexanoic acid, (3S,5S)-3-aminomethyl-5-(4-chloro-phenoxy)-hexanoic acid, (3S,5S)-3-aminomethyl-5-(3-chloro-phenoxy)-hexanoic acid, (3S,5S)-3-aminomethyl-5-(2-chloro-phenoxy)-hexanoic acid, (3S,5S)-3-aminomethyl-5-(4-fluoro-phenoxy)-hexanoic acid, (3S,5S)-3-aminomethyl-5-(3-fluoro-phenoxy)-hexanoic acid, (3S,5S)-3-aminomethyl-5-(2-fluoro-phenoxy)-hexanoic acid, (3S,5S)-3-aminomethyl-5-(4-methoxy-phenoxy)-hexanoic acid, (3S,5S)-3-aminomethyl-5-(3-methoxy-phenoxy)-hexanoic acid, (3S,5S)-3-aminomethyl-5-(2-methoxy-phenoxy)-hexanoic acid, (3S,5S)-3-aminomethyl-5-(4-nitro-phenoxy)-hexanoic acid, (3S,5S)-3-aminomethyl-5-(3-nitro-phenoxy)-hexanoic acid, (3S,5S)-3-aminomethyl-5-(2-nitro-phenoxy)-hexanoic acid, (3S,5S)-3-aminomethyl-6-hydroxy-5-methyl-hexanoic acid, (3S,5S)-3-aminomethyl-6-methoxy-5-methyl-hexanoic acid, (3S,5S)-3-aminomethyl-6-ethoxy-5-methyl-hexanoic acid, (3S,5S)-3-aminomethyl-5-methyl-6-propoxy-hexanoic acid, (3S,5S)-3-aminomethyl-6-isopropoxy-5-methyl-hexanoic acid, (3S,5S)-3-aminomethyl-6-tert-butoxy-5-methyl-hexanoic acid, (3S,5S)-3-aminomethyl-6-fluoromethoxy-5-methyl-hexanoic acid, (3S,5S)-3-aminomethyl-6-(2-fluoro-ethoxy)-5-methyl-hexanoic acid, (3S,5S)-3-aminomethyl-5-methyl-6-(3,3,3-trifluoro-propoxy)-hexanoic acid, (3S,5S)-3-aminomethyl-5-methyl-6-phenoxy-hexanoic acid, (3S,5S)-3-aminomethyl-6-(4-chloro-phenoxy)-5-methyl-hexanoic acid, (3S,5S)-3-aminomethyl-6-(3-chloro-phenoxy)-5-methyl-hexanoic acid, (3S,5S)-3-aminomethyl-6-(2-chloro-phenoxy)-5-methyl-hexanoic acid, (3S,5S)-3-aminomethyl-6-(4-fluoro-phenoxy)-5-methyl-hexanoic acid, (3S,5S)-3-aminomethyl-6-(3-fluoro-phenoxy)-5-methyl-hexanoic acid, (3S,5S)-3-aminomethyl-6-(2-fluoro-phenoxy)-5-methyl-hexanoic acid, (3S,5S)-3-aminomethyl-6-(4-methoxy-phenoxy)-5-methyl-hexanoic acid, (3S,5S)-3-aminomethyl-6-(3-methoxy-phenoxy)-5-methyl-hexanoic acid, (3S,5S)-3-aminomethyl-6-(2-methoxy-phenoxy)-5-methyl-hexanoic acid, (3S,5S)-3-aminomethyl-5-methyl 6-(4-trifluoromethyl-phenoxy)-hexanoic acid, (3S,5S)-3-aminomethyl-5-methyl 6-(3-trifluoromethyl-phenoxy)-hexanoic acid, (3S,5S)-3-aminomethyl-5-methyl 6-(2-trifluoromethyl-phenoxy)-hexanoic acid, (3S,5S)-3-aminomethyl-5-methyl 6-(4-nitro-phenoxy)-hexanoic acid, (3S,5S)-3-aminomethyl-5-methyl 6-(3-nitro-phenoxy)-hexanoic acid, (3S,5S)-3-aminomethyl-5-methyl 6-(2-nitro-phenoxy)-hexanoic acid, (3S,5S)-3-aminomethyl-6-benzyloxy-5-methyl-hexanoic acid, (3S,5S)-3-aminomethyl-7-hydroxy-5-methyl-heptanoic acid, (3S,5S)-3-aminomethyl-7-methoxy-5-methyl-heptanoic acid, (3S,5S)-3-aminomethyl-7-ethoxy-5-methyl-heptanoic acid, (3S,5S)-3-aminomethyl-5-methyl-7-propoxy-heptanoic acid, (3S,5S)-3-aminomethyl-7-isopropoxy-5-methyl-heptanoic acid, (3S,5S)-3-aminomethyl-7-tert-butoxy-5-methyl-heptanoic acid, (3S,5S)-3-aminomethyl-7-fluoromethoxy-5-methyl-heptanoic acid, (3S,5S)-3-aminomethyl-7-(2-fluoro-ethoxy)-5-methyl-heptanoic acid, (3S,5S)-3-aminomethyl-5-methyl-7-(3,3,3-trifluoro-propoxy)-heptanoic acid, (3S,5S)-3-aminomethyl-7-benzyloxy-5-methyl-heptanoic acid, (3S,5S)-3-aminomethyl-5-methyl-7-phenoxy-heptanoic acid, (3S,5S)-3-aminomethyl-7-(4-chloro-phenoxy)-5-methyl-heptanoic acid, (3S,5S)-3-aminomethyl-7-(3-chloro-phenoxy)-5-methyl-heptanoic acid, (3S,5S)-3-aminomethyl-7-(2-chloro-phenoxy)-5-methyl-heptanoic acid, (3S,5S)-3-aminomethyl-7-(4-fluoro-phenoxy)-5-methyl-heptanoic acid, (3S,5S)-3-aminomethyl-7-(3-fluoro-phenoxy)-5-methyl-heptanoic acid, (3S,5S)-3-aminomethyl-7-(2-fluoro-phenoxy)-5-methyl-heptanoic acid, (3S,5S)-3-aminomethyl-7-(4-methoxy-phenoxy)-5-methyl-heptanoic acid, (3S,5S)-3-aminomethyl-7-(3-methoxy-phenoxy)-5-methyl-heptanoic acid, (3S,5S)-3-aminomethyl-7-(2-methoxy-phenoxy)-5-methyl-heptanoic acid, (3S,5S)-3-aminomethyl-5-methyl-7-(4-trifluoromethyl-phenoxy)-heptanoic acid, (3S,5S)-3-aminomethyl-5-methyl-7-(3-trifluoromethyl-phenoxy)-heptanoic acid, (3S,5S)-3-aminomethyl-5-methyl-7-(2-trifluoromethyl-phenoxy)-heptanoic acid, (3S,5S)-3-aminomethyl-5-methyl-7-(4-nitro-phenoxy)-heptanoic acid, (3S,5S)-3-aminomethyl-5-methyl-7-(3-nitro-phenoxy)-heptanoic acid, (3S,5S)-3-aminomethyl-5-methyl-7-(2-nitro-phenoxy)-heptanoic acid, (3S,5S)-3-aminomethyl-5-methyl-6-phenyl-hexanoic acid, (3S,5S)-3-aminomethyl-6-(4-chloro-phenyl)-5-methyl-hexanoic acid, (3S,5S)-3-aminomethyl-6-(3-chloro-phenyl)-5-methyl-hexanoic acid, (3S,5S)-3-aminomethyl-6-(2-chloro-phenyl)-5-methyl-hexanoic acid, (3S,5S)-3-aminomethyl-6-(4-methoxy-phenyl)-5-methyl-hexanoic acid, (3S,5S)-3-aminomethyl-6-(3-methoxy-phenyl)-5-methyl-hexanoic acid, (3S,5S)-3-aminomethyl-6-(2-methoxy-phenyl)-5-methyl-hexanoic acid, (3S,5S)-3-aminomethyl-6-(4-fluoro-phenyl)-5-methyl-hexanoic acid, (3S,5S)-3-aminomethyl-6-(3-fluoro-phenyl)-5-methyl-hexanoic acid, (3S,5S)-3-aminomethyl-6-(2-fluoro-phenyl)-5-methyl-hexanoic acid, (3S,5R)-3-aminomethyl-5-methyl-7-phenyl-heptanoic acid, (3S,5R)-3-aminomethyl-7-(4-chloro-phenyl)-5-methyl-heptanoic acid, (3S,5R)-3-aminomethyl-7-(3-chloro-phenyl)-5-methyl-heptanoic acid, (3S,5R)-3-aminomethyl-7-(2-chloro-phenyl)-5-methyl-heptanoic acid, (3S,5R)-3-aminomethyl-7-(4-methoxy-phenyl)-5-methyl-heptanoic acid, (3S,5R)-3-aminomethyl-7-(3-methoxy-phenyl)-5-methyl-heptanoic acid, (3S,5R)-3-aminomethyl-7-(2-methoxy-phenyl)-5-methyl-heptanoic acid, (3S,5R)-3-aminomethyl-7-(4-fluoro-phenyl)-5-methyl-heptanoic acid, (3S,5R)-3-aminomethyl-7-(3-fluoro-phenyl)-5-methyl-heptanoic acid, (3S,5R)-3-aminomethyl-7-(2-fluoro-phenyl)-5-methyl-heptanoic acid, (3S,5R)-3-aminomethyl-5-methyl-oct-7-enoic acid, (3S,5R)-3-aminomethyl-5-methyl-non-8-enoic acid,

TABLE 2-continued (E)-(3S,5S)-3-aminomethyl-5-methyl-oct-6-enoic acid, (Z)-(3S,5S)-3-aminomethyl-5-methyl-oct-6-enoic acid, (Z)-(3S,5S)-3-aminomethyl-5-methyl-non-6-enoic acid, (E)-(3S,5S)-3-aminomethyl-5-methyl-non-6-enoic acid, (E)-(3S,5R)-3-aminomethyl-5-methyl-non-7-enoic acid, (Z)-(3S,5R)-3-aminomethyl-5-methyl-non-7-enoic acid, (Z)-(3S,5R)-3-aminomethyl-5-methyl-dec-7-enoic acid, (E)-(3S,5R)-3-aminomethyl-5-methyl-undec-7-enoic acid, (3S,5S)-3-aminomethyl-5,6,6-trimethyl-heptanoic acid, (3S,5S)-3-aminomethyl-5,6-dimethyl-heptanoic acid, (3S,5S)-3-aminomethyl-5-cyclopropyl-hexanoic acid, (3S,5S)-3-aminomethyl-5-cyclobutyl-hexanoic acid, (3S,5S)-3-aminomethyl-5-cyclopentyl-hexanoic acid, (3S,5S)-3-aminomethyl-5-cyclohexyl-hexanoic acid, (3S,5R)-3-aminomethyl-5-methyl-heptanoic acid, (3S,5R)-3-aminomethyl-5-methyl-octanoic acid, (3S,5R)-3-aminomethyl-5-methyl-nonanoic acid, (3S,5R)-3-aminomethyl-5-methyl-decanoic acid, (3S,5R)-3-aminomethyl-5-methyl-undecanoic acid, (3S,5R)-3-aminomethyl-5-methyl-dodecanoic acid, (3S,5R)-3-aminomethyl-5,9-dimethyl-decanoic acid, (3S,5R)-3-aminomethyl-5,7-dimethyl-octanoic acid, (3S,5R)-3-aminomethyl-5,8-dimethyl-nonanoic acid, (3S,5R)-3-aminomethyl-6-cyclopropyl-5-methyl-hexanoic acid, (3S,5R)-3-aminomethyl-6-cyclobutyl-5-methyl-hexanoic acid, (3S,5R)-3-aminomethyl-6-cyclopentyl-5-methyl-hexanoic acid, (3S,5R)-3-aminomethyl-6-cyclohexyl-5-methyl-hexanoic acid, (3S,5R)-3-aminomethyl-7-cyclopropyl-5-methyl-heptanoic acid, (3S,5R)-3-aminomethyl-7-cyclobutyl-5-methyl-heptanoic acid, (3S,5R)-3-aminomethyl-7-cyclopentyl-5-methyl-heptanoic acid, (3S,5R)-3-aminomethyl-7-cyclohexyl-5-methyl-heptanoic acid, (3S,5R)-3-aminomethyl-8-cyclopropyl-5-methyl-octanoic acid, (3S,5R)-3-aminomethyl-8-cyclobutyl-5-methyl-octanoic acid, (3S,5R)-3-aminomethyl-8-cyclopentyl-5-methyl-octanoic acid, (3S,5R)-3-aminomethyl-8-cyclohexyl-5-methyl-octanoic acid, (3S,5S)-3-aminomethyl-6-fluoro-5-methyl-hexanoic acid, (3S,5S)-3-aminomethyl-7-fluoro-5-methyl-heptanoic acid, (3S,5R)-3-aminomethyl-8-fluoro-5-methyl-octanoic acid, (3S,5R)-3-aminomethyl-9-fluoro-5-methyl-nonanoic acid, (3S,5S)-3-aminomethyl-7,7,7-trifluoro-5-methyl-heptanoic acid, (3S,5R)-3-aminomethyl-8,8,8-trifluoro-5-methyl-octanoic acid, (3S,5R)-3-aminomethyl-5-methyl-8-phenyl-octanoic acid, (3S,5S)-3-aminomethyl-5-methyl-6-phenyl-hexanoic acid, (3S,5R)-3-aminomethyl-5-methyl-7-phenyl-heptanoic acid.

Compounds described in the invention can be prepared by methods known in the art. For examples, compounds described in the invention can be prepared according to the methods described in PCT Publication WO 2006/127945 and PCT Application Nos. PCT/US2013/076592 and PCT/US2014/012356, the contents of each of which are incorporated herein by reference in their entirety.

Compounds within the scope of the instant invention may contain chiral centers and thus are capable of existing as racemates, racemic mixtures, diastereomers and single enantiomers. All such forms should be understood as within the scope of this invention.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl", "$C_3$, $C_4$, $C_5$, $C_6$, $C_7$ or $C_8$ cycloalkyl" or "$C_3$-$C_8$ cycloalkyl" is intended to include hydrocarbon rings having from three to eight carbon atoms in their ring structure. In one embodiment, a cycloalkyl group has five or six carbons in the ring structure.

The term "substituted alkyl" refers to alkyl moieties having substituents replacing one or more hydrogen atoms on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, $NH_2$, alkylamino, dialkylamino, arylamino, diarylamino, alkylarylamino, acylamino (the term "acylamino" includes alkylcarbonylamino, arylcarbonylamino, carbamoyl, and ureido), amidino, imino, sulfhydryl, alkylthio, arylthio, thiocarboxylate, sulfate, alkylsulfinyl, sulfamoyl, sulfonamido, trifluoromethyl, azido, heterocyclyl, alkylaryl, and an aromatic or heteroaromatic moiety.

"Alkenyl" includes unsaturated aliphatic groups analogous in length and possible substitution to the alkyls described above, but that contain at least one double bond. For example, the tem' "alkenyl" includes straight chain alkenyl groups (e.g., ethenyl, propenyl, butenyl, pentenyl, hexenyl, heptenyl, octenyl, nonenyl, decenyl), branched alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched alkenyl group has six or fewer carbon atoms in its backbone (e.g., $C_2$-$C_6$ for straight chain, $C_3$-$C_6$ for branched chain). Likewise, cycloalkenyl groups may have from five to eight carbon atoms in their ring structure, and in one embodiment, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

"Aryl" includes groups with aromaticity, including "conjugated", or multicyclic, systems with at least one aromatic ring. Examples include phenyl, benzyl, etc.

"Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and Spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran. Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromenyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The present invention is also directed to the use of a compound described herein in the manufacture of a medicament for the treatment, prevention, and/or reduction of a risk of a disease, disorder, or condition in which aldehyde toxicity is implicated in the pathogenesis. More specifically this aspect of the invention is directed to the use of a compound described herein in the manufacture of a medicament for the treatment, prevention, and/or reduction of a risk of (1) an ocular disease, disorder, or condition, including, but not limited to, a corneal disease (e.g., dry eye syndrome, cataracts, keratoconus, bullous and other keratopathy, and Fuch's endothelial dystrophy), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions associated with high aldehyde levels as a result of inflammation (e.g., uveitis, scleritis, ocular Stevens Johnson Syndrome, and ocular rosacea (with or without meibomian gland dysfunction)), (2) a skin disorder or condition or a cosmetic indication. For example, the disease, disorder, or condition includes, but is not limited to, psoriasis, topical (discoid) lupus, contact dermatitis, atopic dermatitis, allergic dermatitis, radiation dermatitis, acne vulgaris, Sjogren-Larsson Syndrome and other ichthyosis, solar elastosis/wrinkles, skin tone firmness, puffiness, eczema, smoke or irritant induced skin changes, dermal incision, and a skin condition associated burn and wound, (3) a condition associated with the toxic effects of blister agents or burns from alkali agents, or (4) an autoimmune, immune-mediated, inflammatory, cardiovascular, or neurological disease (e.g., lupus, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, multiple sclerosis, amyotrophic lateral sclerosis, diabetes, metabolic syndrome, and fibrotic diseases).

A "patient," "subject," or "host" to be treated by the subject method may mean either a human or non-human animal, such as primates, mammals, and vertebrates.

The terms "administering of" or "administering a" should be understood to mean providing a compound or a salt thereof or a pharmaceutical composition to a patient in need of treatment, prevention, or reduction in risk or a symptom.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease, disorder or condition includes ameliorating at least one symptom of the particular disease, disorder or condition, even if the underlying pathophysiology is not affected.

The term "preventing" is art-recognized and includes stopping a disease, disorder or condition from occurring in a subject which may be predisposed to the disease, disorder and/or condition but has not yet been diagnosed as having it. Preventing a condition related to a disease includes stopping the condition from occurring after the disease has been diagnosed but before the condition has been diagnosed.

The term "reducing the risk of" means that the likelihood of a subject to suffer from a disease, disorder or condition is decreased, for example, from between 50% and 100% to between 0 and 90%, between 0 and 80%, between 0 and 70%, between 0 and 60%, or between 0 and 50%, or decreased by 10%, 20%, 30%, 40%, 50%, 60%, 70%, 80%, or 90%.

The term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom.

The term "symptom" is defined as an indication of disease, illness, injury, or that something is not right in the body. Symptoms are felt or noticed by the individual experiencing the symptom, but may not easily be noticed by others. Others are defined as non-health-care professionals.

The present invention is also directed to the use of a compound described herein in treating, preventing, and/or reducing a risk of a disease, disorder, or condition in which aldehyde toxicity is implicated in the pathogenesis. More specifically this aspect of the invention is directed to the use of a compound described herein in treating, preventing, and/or reducing a risk of (1) an ocular disease, disorder, or condition, including, but not limited to, a corneal disease (e.g., dry eye syndrome, cataracts, keratoconus, bullous and other keratopathy, and Fuch's endothelial dystrophy), other ocular disorders or conditions (e.g., allergic conjunctivitis, ocular cicatricial pemphigoid, conditions associated with PRK healing and other corneal healing, and conditions associated with tear lipid degradation or lacrimal gland dysfunction), and other ocular conditions associated with high aldehyde levels as a result of inflammation (e.g., uveitis, scleritis, ocular Stevens Johnson Syndrome, and ocular rosacea (with or without meibomian gland dysfunction)), (2) a skin disorder or condition or a cosmetic indication. For example, the disease, disorder, or condition includes, but is not limited to, psoriasis, topical (discoid) lupus, contact dermatitis, atopic dermatitis, allergic dermatitis, radiation dermatitis, acne vulgaris, Sjogren-Larsson Syndrome and other ichthyosis, solar elastosis/wrinkles, skin tone firmness, puffiness, eczema, smoke or irritant induced skin changes, dermal incision, and a skin condition associated burn and wound, (3) a condition associated with the toxic effects of blister agents or burns from alkali agents, or (4) an autoimmune, immune-mediated, inflammatory, cardiovascular, or neurological disease (e.g., lupus, scleroderma, asthma, chronic obstructive pulmonary disease (COPD), rheumatoid arthritis, inflammatory bowel disease, sepsis, atherosclerosis, ischemic-reperfusion injury, Parkinson's disease, Alzheimer's disease, multiple sclerosis, amyotrophic lateral sclerosis, diabetes, metabolic syndrome, and fibrotic diseases).

The term "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" is art-recognized, and includes relatively non-toxic, inorganic and organic acid addition salts, and inorganic and organic base addition salts, including without limitation, the compounds described herein. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, J. Pharm. Sci. 66:1-19 (1977).

The compounds described herein may be administered in the parent form or as a pharmaceutically acceptable salt. A compound described herein should be understood to include both. Pharmaceutically acceptable salts can be prepared from a parent compound that contains basic or acidic moieties by conventional chemical methods. Acid addition salts would include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds described herein can form pharmaceutically acceptable salts with various amino acids. Suitable base salts include, but are not limited to, aluminum, calcium, lithium, magnesium, potassium, sodium, zinc, and diethanolamine salts. For reviews on pharmaceutically acceptable salts see S. M. Berge, L. D. Bighley and D. C. Monkhouse, Pharmaceutical salts, J. Pharm. Sci., 66, 1-19 (1977) and P. H. Stahl and C. G. Wermuth (eds.), Pharmaceutical Salts: Properties, Selection, and Use, Weinheim, Germany: Wiley and Verlag Helvetica Chimica Acta, 2002 [ISBN 3-906390-26-8], incorporated herein by reference. Reference to the parent compound or a salt thereof should be understood to include all hydrates of the compound and all polymorphic forms of the parent compound.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A "pharmaceutical composition" is a formulation containing the disclosed compounds in a form suitable for administration to a subject. In a preferred embodiment, the pharmaceutical composition is in bulk or in unit dosage form. The unit dosage form is any of a variety of forms, including, for example, a tablet, a capsule, an IV bag, a vial, or a single pump on an aerosol inhaler. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. In a preferred embodiment, the active compound is mixed under sterile conditions with a pharmaceutically acceptable carrier, and optionally with any preservatives, buffers, or propellants that may be required.

The compounds described herein may be administered with a pharmaceutically acceptable carrier in a pharmaceutical composition. The pharmaceutical compositions of the present invention encompass any composition made by admixing a therapeutically effective amount of a compound described herein with a pharmaceutically acceptable carrier. The administration may be by systemic means.

"Systemic administration" or "administered systemically" refers to a route of administration of the compounds or pharmaceutical compositions described therein such that the effect associated with the administration of the compounds or pharmaceutical composition is felt throughout the body, and is not limited to a specific location at which or a particular means by which the compounds or pharmaceutical compositions are administered. For example, a systemic administration includes, but is not limited to, an oral, a nasal, a parenteral, a subcutaneous, an intraocular, an intradermal, an intramuscular, an intravenous, an intraperitoneal, an intrathecal, intra-vesicular, intra-ventricular, intra-peritoneal, intra-parenchymal, a transdermal, and a transmucosal administration.

The compounds described herein can also be administered topically, such as directly to the eye, e.g., as an eye-drop or ophthalmic ointment. Eye drops typically comprise an effective amount of at least one compound described herein and a carrier capable of being safely applied to an eye. For example, the eye drops are in the form of an isotonic solution, and the pH of the solution is adjusted so that there is no irritation of the eye. In many instances, the epithelial barrier interferes with penetration of molecules into the eye. Thus, most currently used ophthalmic drugs are supplemented with some form of penetration enhancer. These penetration enhancers work by loosening the tight junctions of the most superior epithelial cells (Burstein, Trans Ophthalmol Soc UK 104: 402 (1985); Ashton et al., J Pharmacol Exp Ther 259: 719 (1991); Green et al., Am J Ophthalmol 72: 897 (1971)). The most commonly used penetration enhancer is benzalkonium chloride (Tang et al., J Pharm Sci 83: 85 (1994); Burstein et al, Invest Ophthalmol Vis Sci 19: 308 (1980)), which also works as preservative against microbial contamination.

Topical administration may be in the form of a cream, suspension, emulsion, ointment, drops, oil, lotion, patch, tape, inhalant, spray, or controlled release topical formulations including gels, films, patches, and adhesives. Intraocular administration may take the form of subconjunctival, subtenon's capsule, retrobulbar or intravitreal injections, depots or implants. Compounds administered by these routes may be in solution or suspension form. Administration of compounds by depot injection may contain pharmaceutically acceptable carriers or excipients; these may be natural or synthetic and may be biodegradable or non-biodegradable and facilitate drug release in a controlled manner. Implants used for controlled release of compound may be composed of natural or synthetic, biodegradable or non-biodegradable materials. The carrier is acceptable in that it is compatible with the other components of the composition and is not injurious to the patient. Some examples of carriers include (1) sugars such as lactose glucose and sucrose, (2) starches such as corn starch and potato starch, (3) cellulose and (4) cyclodextrins. A useful topical formulation is described in PCT publication WO 2011/072141, the contents of which are herein incorporated by reference.

Formulations for topical administration to the skin can include, for example, ointments, creams, gels and pastes comprising the primary amine compound in a pharmaceutical acceptable carrier. The formulation of the primary amine compound for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

The formulations for topical administration may contain the compound used in the present application at a concentration in the range of 0.001-10%, 0.05-10%, 0.1-10%, 0.2-10%, 0.5-10%, 1-10%, 2-10%, 3-10%, 4-10%, 5-10%, or 7-10% (weight/volume), or in the range of 0.001-2.0%, 0.001-1.5%, or 0.001-1.0%, (weight/volume), or in the range of 0.05-2.0%, 0.05-1.5%, or 0.05-1.0%, (weight/volume), or in the range of 0.1-5.0%, 0.1-2.0%, 0.1-1.5%, or 0.1-1.0% (weight/volume), or in the range of 0.5-5.0%, 0.5-2.0%, 0.5-1.5%, or 0.5-1.0% (weight/volume), or in the range of 1-5.0%, 1-2.0%, or 1-1.5% (weight/volume). The formulations for topical administration may also contain the compound used in the present application at a concentration in the range of 0.001-2.5%, 0.01-2.5%, 0.05-2.0%, 0.1-2.0%, 0.2-2.0%, 0.5-2.0%, or 1-2.0% (weight/weight), or in the range of 0.001-2.0%, 0.001-1.5%, 0.001-1.0%, or 0.001-5% (weight/weight).

In an eye drop formulation the composition may contain the active compound at a concentration of 0.01-20%, 0.02-15%, 0.04-10%, 0.06-5%, 0.08-1%, or 0.09-0.5% (weight/volume) with or without pH and/or osmotic adjustment to the solution. More particularly, the eye drop formulation may contain a compound described herein at a concentration of 0.09-0.5% (weight/volume), such as 0.1%.

In one exemplification, the pharmaceutical compositions encompass a composition made by admixing a therapeutically effective amount of a compound described herein with an oligomeric or a polymeric carrier such as a cyclodextrin, or chemically modified cyclodextrin, including trimethyl-β-cyclodextrin, 2-hydroxyethyl-β-cyclodextrin, 2-hydroxypropyl-β-cyclodextrin, 3-hydroxypropyl-β-cyclodextrin, and β-cyclodextrin sulfobutylether sodium salt (or potassium salt). Exemplifying an oligomeric or a polymeric carrier is β-cyclodextrin sulfobutylether sodium salt. The amount of β-cyclodextrin sulfobutylether sodium salt in the composition may range from about 0.01% to 30% weight/volume. In one illustration, the concentration of β-cyclodextrin sulfobutylether sodium salt is 5-25% weight/volume. Further illustrating the concentration of β-cyclodextrin sulfobutylether sodium salt is 6-20% weight/volume. In one exemplification the concentration of β-cyclodextrin sulfobutylether is 6-12% weight/volume. Further exemplifying the concentration of β-cyclodextrin sulfobutylether is 9-10% weight/volume, including 9.5% weight/volume. The amount of the compound described herein in the composition may range 0.01-20%, 0.02-15%, 0.04-10%, 0.06-5%, 0.08-1%, or 0.09-0.5% (weight/volume). More particularly, the composition may contain a compound described herein at a concentration of 0.09-0.5% (weight/volume), such as 0.1%.

The compounds described herein may be administered orally and as such the pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

For oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, croscarmellose or its sodium salt, and the like. Diluents, include, e.g., lactose, dextrose, sucrose, mannitol, sorbitol, cellulose and/or glycine.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A therapeutically effective dose, of a compound described herein in an oral formulation, may vary from 0.01 mg/kg to 50 mg/kg patient body weight per day, more particularly 0.01 to 10 mg/kg, which can be administered in single or multiple doses per day. For oral administration the drug can be delivered in the form of tablets or capsules containing 1 mg to 500 mg of the active ingredient specifically, 1 mg, 5 mg, 10 mg, 20 mg, 50 mg, 100 mg, 250 mg, and 500 mg, or in the forms of tables or capsules containing at least 1%, 2%, 5%, 10%, 15%, 20%, 25%, 30%, 40%, 50% (w/w) of the active ingredient. For example, the capsules may contain 50 mg of the active ingredient, or 5-10% (w/w) of the active ingredient. For example, the tablets may contain 100 mg of the active ingredient, or 20-50% (w/w) of the active ingredient. For example, the tablet may contain, in addition to the active ingredient, a disintegrant (e.g., croscarmellose or its sodium salt and methyl cellulose), a diluent (e.g., microcrystalline cellulose), and a lubricant (e.g., sodium stearate and magnesium stearate). The drug can be administered on a daily basis either once, twice or more per day.

For administration by inhalation, the compounds are delivered in the form of an aerosol spray from pressured container or dispenser, which contains a suitable propellant, e.g., a gas such as carbon dioxide, or a nebulizer.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Parenteral formulations comprising a compound described herein can be prepared in aqueous isotonic solutions or suspensions, and suppositories are advantageously prepared from fatty emulsions or suspensions. The formulations may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional methods, and may contain about 0.1 to 75%, preferably about 1 to 50%, of a compound described herein.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

EXAMPLES

Example 1

Figure 2:
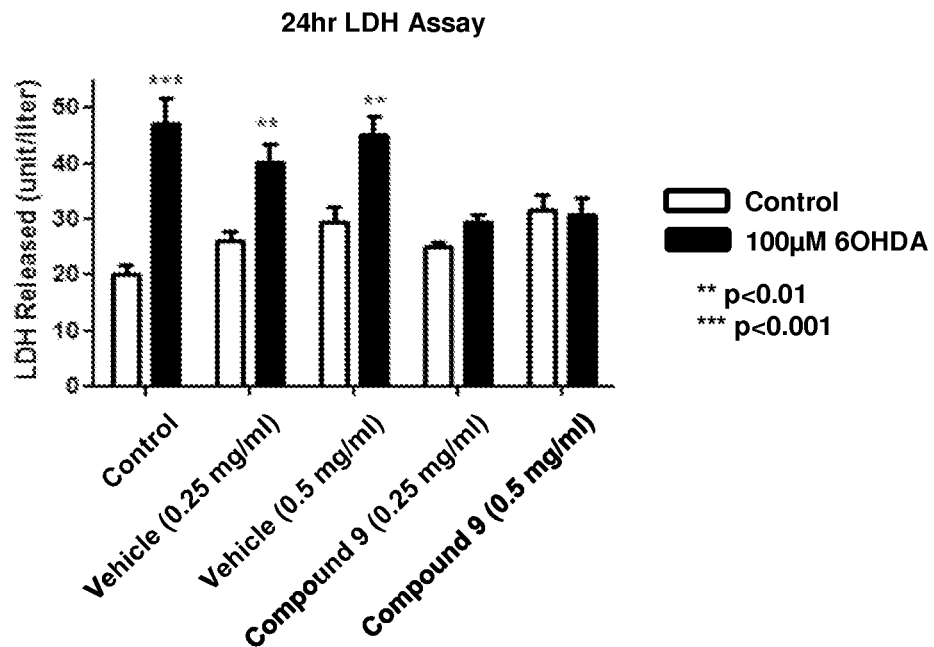
FIG. 2. Bar graphs showing that Compound 9 prevents aldehyde-mediated cell death in neurons FIG. 3. A bar graph showing broad downregulation of inflammatory cytokines by a single dose of Compound 9
Figure 2:
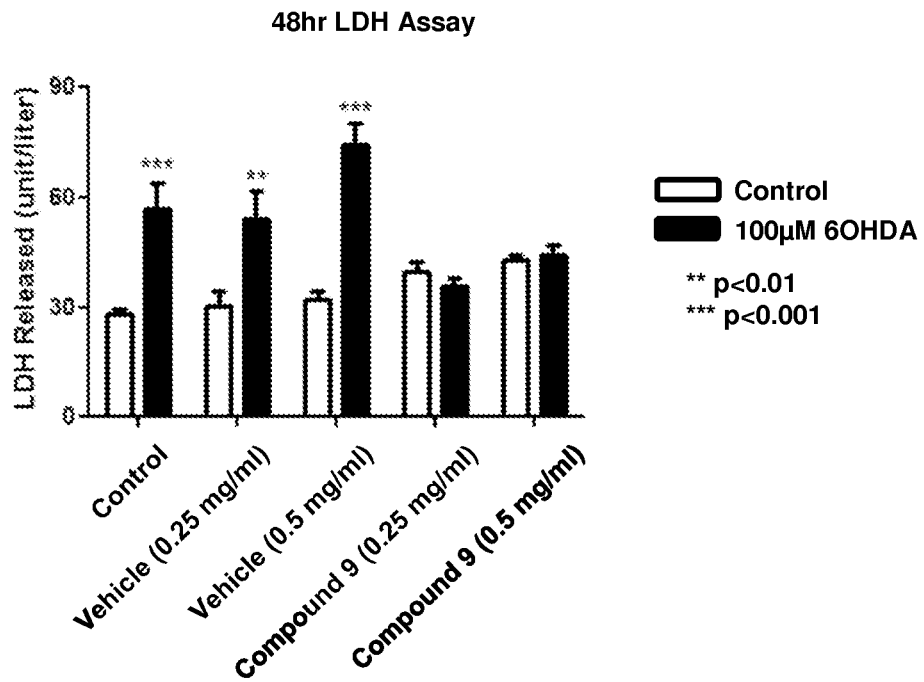

Primary rat cortical cultures were placed in an incubator for 24 or 48 hours and treated with various concentrations of Compound 9. Then 20 µL of the culture media was removed for an LDH assay as described in Bergmeyer et al., Methods of Enzymatic Analysis, $3^{rd}$ ed. (1983). As shown in FIG. 2, Compound 9 prevented aldehyde-mediated cell death in neurons.

Example 2

Figure 3:
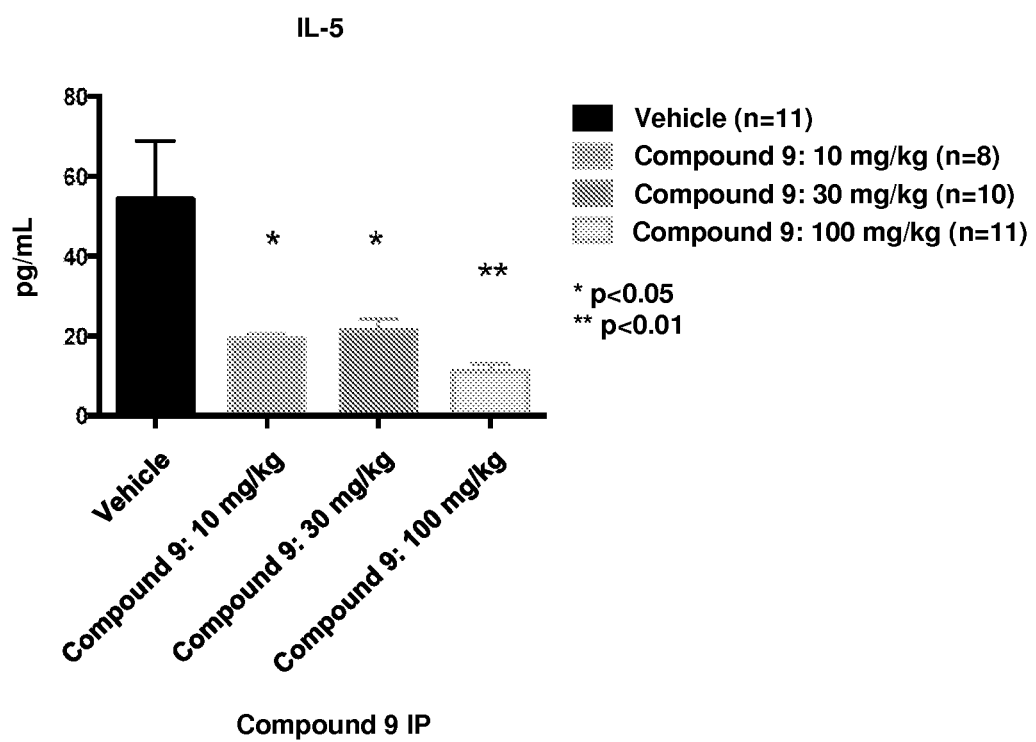
Figure 4:
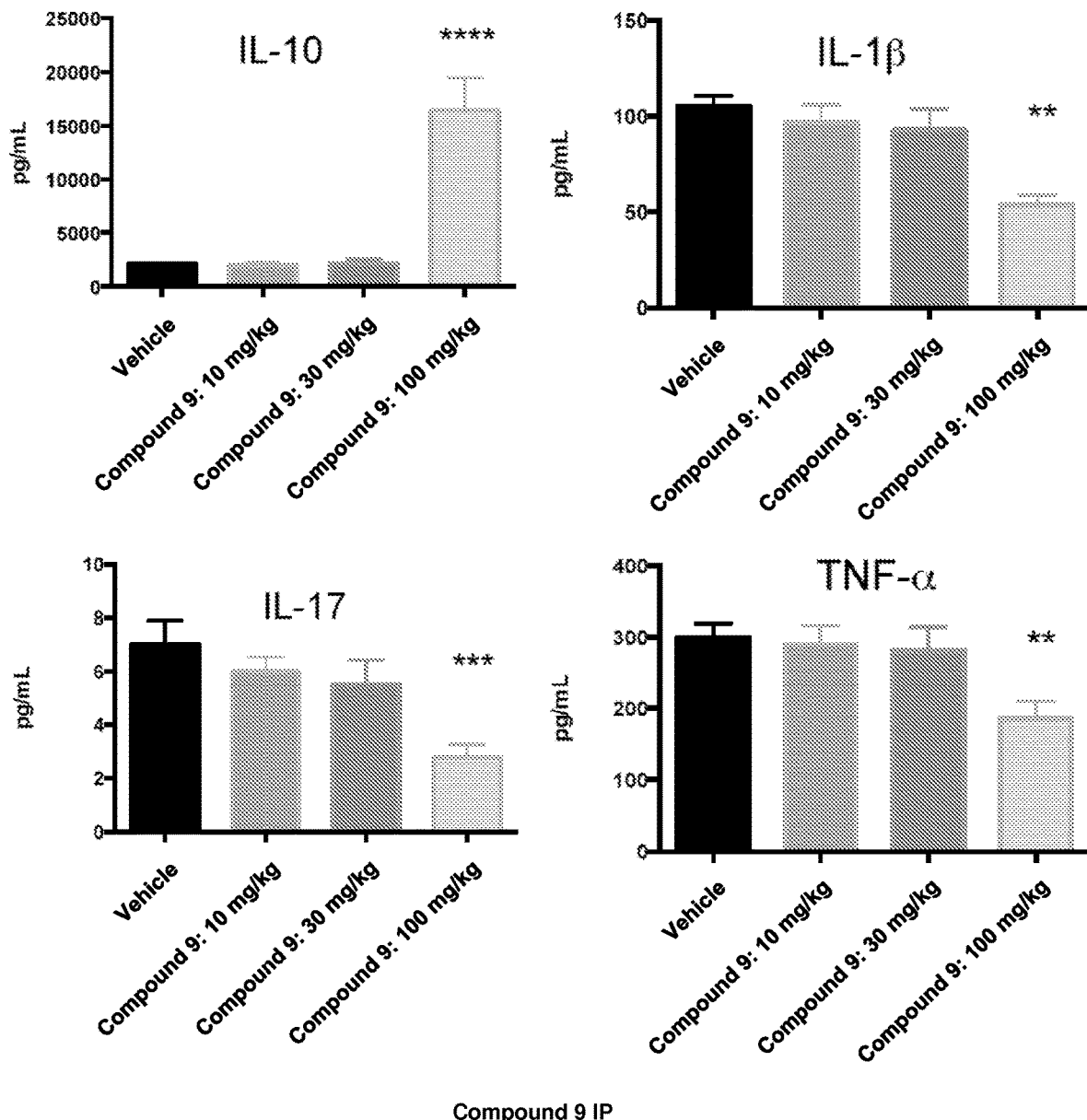
FIG. 4. Bar graphs showing the anti-inflammatory profile of a single-dose of Compound 9 in response to LPS treatment FIG. 5. Bar graphs showing the efficacy of a single dose of Compound 9 in (A) contact dermatitis and (B) allergic dermatitis FIG. 6. (A) a plot and a table showing the mucositis score over time in hamsters subject to 40 Gy irradiation and treated with or without Compound 9, (B) photographs of cheeks of hamsters subject to 40 Gy irradiation and treated with or without Compound 9

Male C57Bl/6 mice were dosed with Compound 9 30 minutes before they were exposed to LPS (20 mg/kg). Two hours after the LPS exposure, blood was collected from the mice and an ELISA was conducted to determine the amount of circulating cytokines. As shown in FIGS. 3 and 4, Compound 9 treatment led to reduction in proinflammatory cytokines, such as IL-5 and IL-1l3, IL-17, and TNF. Also, FIG. 4 shows that Compound 9 treatment resulted in elevated anti-inflammatory cytokines, such as IL-10. In addition, various other chemokines, such as eotaxin, IL-12, IP-10, LIF, MCP-1, MIG, MIP, and RANTES, were also decreased by Compound 9 treatment.

Example 3

Figure 5:
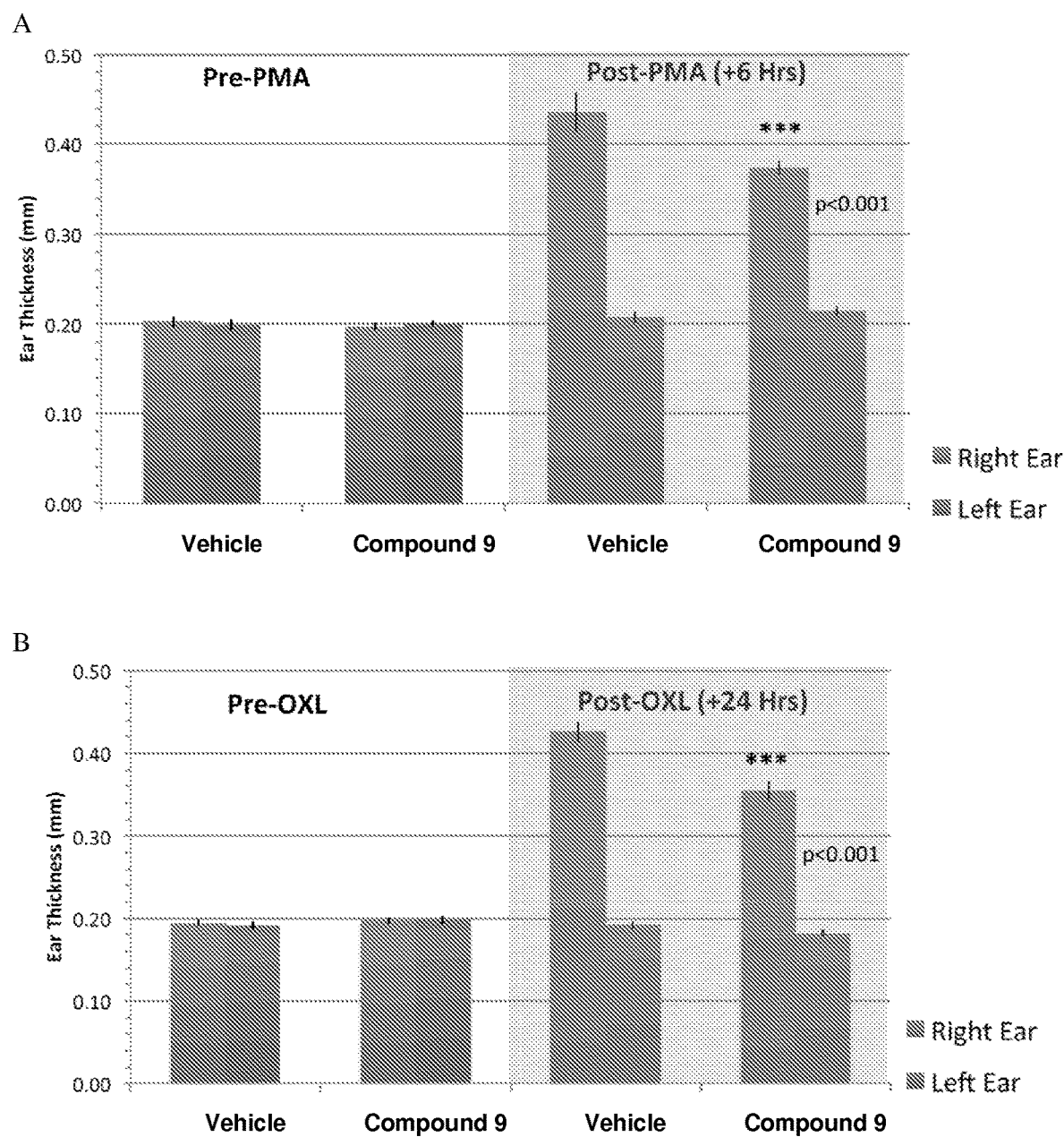
Figure 6:
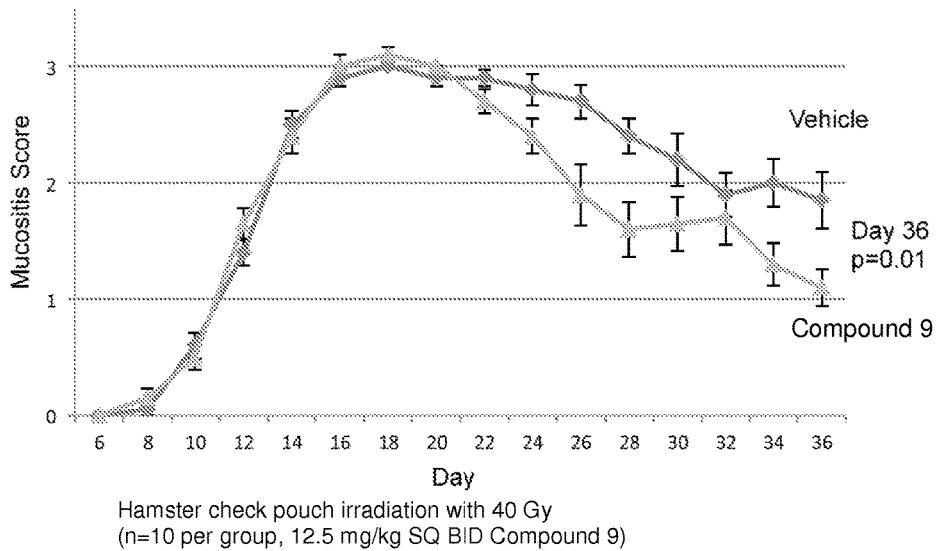
Figure 6:
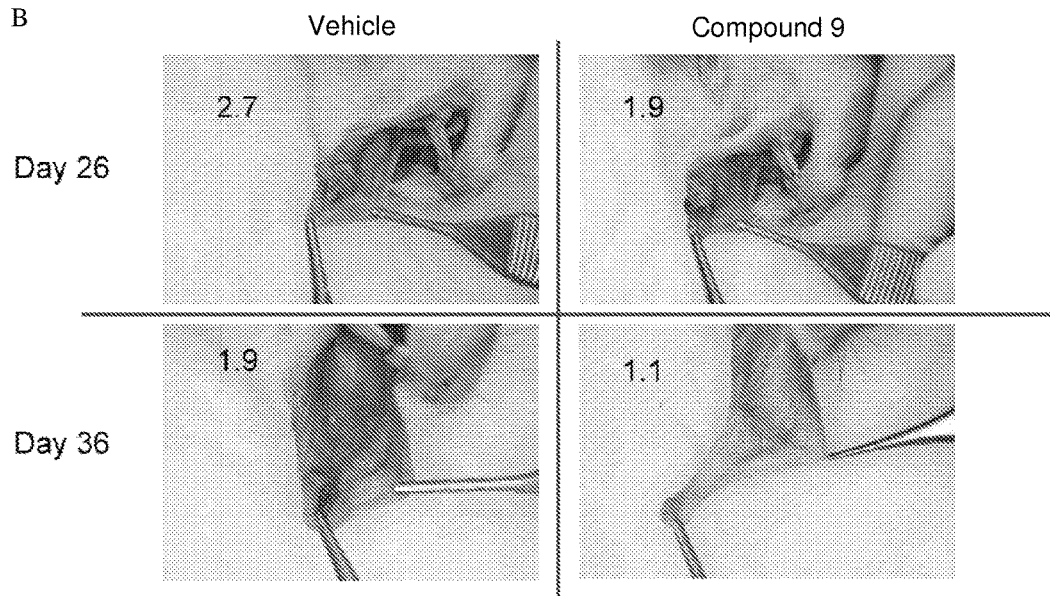
Figure 7:
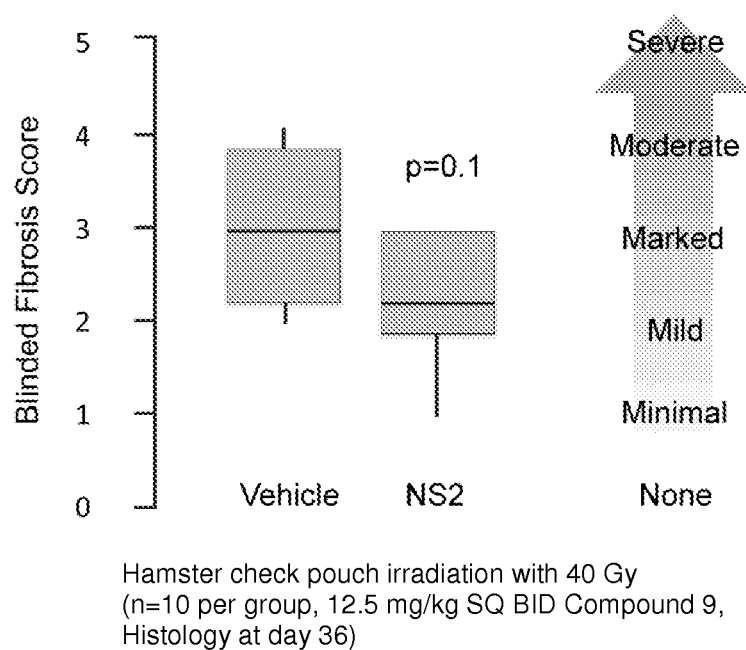
FIG. 7. A bar plot showing that Compound 9 treatment diminishes radiation induced fibrosis in hamsters subject to 40 Gy irradiation

To determine the efficacy of Compound 9 in treating contact dermatitis, phorbol myristate acetate ("PMA") was applied topically (2.5 µg in 20 µL) to both the anterior and posterior portions of the right pinna of mice (N=10 per group). As a control, the left pinna received 20 µL of ethanol (PMA excipient) to both the anterior and posterior portions. Six hours after the PMA application, both the right and left pinna thickness was determined. Measurements were determined at least twice from the same region of both ears, with care taken not to include hair or folded pinna. The results are shown in FIG. 5A.

Example 4

To measure the efficacy of Compound 9 in treating allergic dermatitis, oxazolone ("OXL") was applied (1.5%, 100 µL in acetone) to the shaved abdomens of mice. Seven days later, the thickness of the pinna of the OXL treated mice was determined. Then Compound 9 (100 mg/kg) or the vehicle (i.e., Captisol) was administered intraperitoneally to mice followed by topical application of OXL (1%, 20 µL) 30 min later to both the anterior and posterior portions of the right pinna. As a control, the left pinna received 20 µL of acetone (OXL excipient) to both the anterior and posterior portions. The thickness of the pinna of both ears was measured again 24 hours later. N=10 per group. The results are shown in FIG. 5B.

Example 5

To five separate reaction vials was added Compounds 1, 2, 12, 14, and 16, respectively (0.064 mmol), MDA salt (22.7% MDA, 0.064 mmol), and glyceryl trioleate (600 mg). To the mixture was added 20 wt % Captisol in aqueous PBS (~2.5 ml), followed by linoleic acid (600 mg). The reaction mixture was stirred vigorously at ambient temperature and monitored by LC/MS. The Compounds quickly react with MDA to form MDA adducts. For Compounds 1, 12, 14, and 16, a majority of the adducts were bis-oxaminal. Other MDA adducts were also formed at different time points of the reactions.

Compound 9 also reacted with MDA and formed MDA adducts, in both the imine form and the oxaminal form.

Thus, each of Compounds 1, 2, 9, 12, 14, and 16 reacts and traps MDA.

Example 6. Synthesis of 2-(3-amino-6-chloro-5-fluoroquinolin-4-yl)propan-2-ol (Compound (1))

(E)- and (Z)-3-chloro-2-fluoro-6-(2-nitrovinylamino)benzoic acid (1-1). 37.19 g crude wet methazonic acid (prepared by the method of G. B. Bachman et al., J Am. Chem. Soc. 69, 365-371 (1947)) was mixed with 50 g 6-amino-3-chloro-2-fluorobenzoic acid (Butt Park Ltd., Camelford, Cornwall, UK) and 750 mL acetone and shaken until a clear solution was formed. To the solution was added sequentially 200 mL water and 200 mL 12 N HCl, and the solution was kept 3 days at room temperature. The mixture was diluted with 2 L water and filtered. The filtrate was evaporated to remove acetone and filtered. The combined solids were washed with water (4×200 mL) and dried at 60° C. under high vacuum to afford 1-1 as a 4.5:1 mixture of E- and Z-isomers.

$^1$H NMR (400 MHz, DMSO-$d_6$) δ: E-isomer 6.79 (d, 1H, J=6.4 Hz), 7.58 (d, 1H, J=8.4 Hz), 7.83 (t, 1H, J=8.4 Hz), 7.99 (dd, 1H, J=6.4, 13.2 Hz), 12.34 (d, 1H, NH, J=13.2 Hz), 14.52 (br, 1H, OH). Z-isomer 7.39 (d, 1H, J=11.2 Hz), 7.42 (d, 1H, J=9.6 Hz), 7.71 (t, 1H, J=8.4 Hz), 8.49 (t, 1H, J=11.6 Hz), 10.24 (d, 1H, NH, J=12.4 Hz), 14.52 (br, 1H, OH). LC-MS: 259 [(M-H)$^-$].

6-chloro-5-fluoro-3-nitroquinolin-4-ol (1-2). A mixture of 62.0 g (1-1), 55.2 g N-ethyl-N'-(3-dimethylaminopropyl)carbodiimide hydrochloride (EDC) and 30.1 g N-hydroxysuccinimide (HOSu) in 1 L absolute dimethylformamide (DMF) was stirred at room temperature for 1 h. 4-dimethylaminopyridine (DMAP, 38.7 g) was added and the mixture was stirred at room temperature for 2 h. The mixture was filtered, and the solid was washed with 10% HOAc (4×200 mL), air-dried overnight, and then dried at 60° C. under high vacuum to give (1-2) as a pale yellow powder.

$^1$H NMR (400 MHz, DMSO-$d_6$) δ: 7.52 (dd, 1H, J=0.8, 8.8 Hz), 7.91 (dd, 1H, J=7.2, 8.8 Hz), 9.15 (s, 1H), 13.0 (br, 1H, OH). LC-MS: 242.9 (MH)$^+$, 264.9 (MNa)$^+$.

4-bromo-6-chloro-5-fluoro-3-nitroquinoline (1-3). A mixture of 40 g (1-2) and 71 g POBr$_3$ in 150 mL dry DMF was stirred at 80° C. for 1 h. The mixture was cooled to room temperature, diluted with 2 L CH$_2$Cl$_2$, and transferred to a separatory funnel containing 1.5 L ice water. The organic layer was separated, washed with ice water (3×1.5 L), dried with MgSO$_4$, and evaporated to give crude (1-3) as a light brown solid, which was used without further purification.

$^1$H NMR (400 MHz, CDCl$_3$) δ: 4.70 (br, 2H, NH$_2$), 7.42 (dd, 1H, J=6.0, 9.0 Hz), 7.73 (dd, 1H, J=1.8, 8.8 Hz). LC-MS: 274.8 (MH)$^+$, 276.8 [(M+2)H]$^+$, 278.8 [(M+4)H]$^+$.

4-bromo-6-chloro-5-fluoroquinolin-3-amine (1-4). Crude (1-3) (51.2 g) was dissolved in 40 mL glacial HOAc under Ar, 3 g Fe powder was added, and the mixture was stirred at 60° C. for 10 min. The mixture was diluted with 200 mL EtOAc, filtered through Celite, and the Celite was washed thoroughly with EtOAc. The combined filtrates were passed through a short silica gel column, and the column was washed with EtOAc until all (1-4) was recovered. The combined EtOAc fractions were evaporated to dryness to give crude (1-4) which was crystallized from hexanes-EtOAc to provide (1-4) as a pale brown solid.

$^1$H NMR (400 MHz, CDCl$_3$) δ: 4.70 (br, 2H, NH$_2$), 7.42 (dd, 1H, J=6.0, 9.0 Hz), 7.73 (dd, 1H, J=1.8, 8.8 Hz). LC-MS: 274.8 (MH)$^+$, 276.8 [(M+2)H]$^+$, 278.8 [(M+4)H]$^+$.

2-(3-amino-6-chloro-5-fluoroquinolin-4-yl)propan-2-ol (Compound (1)). A dry 1 L round bottom flask was flushed with argon and cooled to −78° C. in a dry ice/acetone bath. Dry tetrahydrofuran (THF, 300 mL) was injected, followed by 72.6 mL 2.5 M n-BuLi/hexanes. (1-4) (20 g) in 300 mL dry THF was added dropwise with vigorous stirring over 2 h, affording a dark red solution of the 4-quinolinelithium. Ultra dry acetone (27 mL) was added dropwise over 10 min, and the solution was stirred for an additional 10 min. A solution of 20 g NH$_4$Cl in 100 mL water was added and the mixture was warmed to room temperature, transferred to a separatory funnel containing 300 mL EtOAc, and shaken thoroughly. The organic layer was separated and the aqueous layer was extracted with EtOAc (2×250 mL). The combined organic layers were dried with anhydrous MgSO$_4$ and evaporated to a dark brown residue which was partially purified by chromatography on a silica gel column eluted with hexanes-EtOAc to afford a mixture containing 6-chloro-5-fluoroquinolin-3-amine and Compound (1). Compound (1) was isolated by crystallization from hexanes-EtOAc.

$^1$H NMR (400 MHz, CD$_3$OD) δ: 1.79 (s, 3H), 1.80 (s, 3H), 7.36 (dd, 1H, J=7.2, 8.8 Hz), 7.61 (dd, 1H, J=1.6, 9.0 Hz), 8.35 (s, 1H). $^{13}$C NMR (100 MHz, CD$_3$OD) δ: 29.8, 29.9, 76.7, 120.4 (d, $J_{C-F}$=12 Hz), 120.5 (d, $J_{C-F}$=4 Hz), 125.4, 126.1 (d, $J_{C-F}$=3 Hz), 126.6 (d, $J_{C-F}$=3 Hz), 143.1, 143.2 (d, $J_{C-F}$=5 Hz), 148.3, 152.7 (d, $J_{C-F}$=248 Hz). LC-MS: 254.9 (MH)$^+$, 256.9 [(M+2)H]$^+$.

Example 7. Synthesis of 2-(3-amino-6-chloroquinolin-4-yl)propan-2-ol (Compound (2))

6-chloro-3-nitroquinolin-4-ol (2-1). A mixture of cis- and trans-5-chloro-2-(2-nitrovinylamino)benzoic acid (68.4 g, Sus et al., Liebigs Ann. Chem. 583: 150 (1953)), 73 g EDC and 35.7 g HOSu in 1 L dry DMF was stirred at room temperature for 1 h. After adding 45.8 g DMAP the mixture was stirred at room temperature for 2 h. To the stirred mixture was slowly added 1 L 10% HOAc, and the resulting suspension was poured into 2 L 10% HOAc. The solid was filtered off, washed with 10% HOAc (4×400 mL) and dried at 80° C. under high vacuum to give (2-1) as a tan powder.

4-bromo-6-chloro-quinolin-3-amine (2-2). A mixture of 25 g (2-1) and 50 g POBr$_3$ in 100 mL dry DMF was stirred at 80° C. for 1 h. The reaction mixture was cooled to room temperature, diluted with 2 L CH$_2$Cl$_2$, and transferred to a separatory funnel containing 1 L ice water. The organic layer was separated, washed with ice water (3×1 L), dried with MgSO$_4$, and evaporated to provide crude 4-bromo-6-chloroquinolin-4-ol as a light brown solid (38 g, 100% crude yield). The quinolinol was dissolved in 750 mL glacial HOAc, 36 g iron powder was added, and the stirred mixture was heated under Ar at 60° C. until the color turned to grey. The mixture was diluted with 2 L EtOAc, filtered through Celite, and the Celite was washed with EtOAc. The combined filtrates were passed through a short silica gel column which was washed with EtOAc until all (2-2) was recovered. The combined fractions were evaporated to dryness and the residue was crystallized from hexanes-EtOAc to provide (2-2) as a tan solid.

¹H NMR (400 MHz, CDCl₃) δ: 4.47 (br, 2H, NH₂), 7.41 (dd, 1H, J=2.4, 8.8 Hz), 7.89 (d, 1H, J=9.2 Hz), 7.96 (d, 1H, J=2.4 Hz), 8.45 (s, 1H). LC-MS: 256.7 (MH)⁺, 258.7 [(M+2)H]⁺, 260.7 [(M+4)H]⁺.

Synthesis of 2-(3-amino-6-chloroquinolin-4-yl)propan-2-ol (Compound (2)). A mixture of 20 g (2-2) and 800 mL dioxane was stirred at 60° C. until a solution formed, cooled to room temperature, and sparged with dry HCl for 5 min. The solvent was evaporated, and 500 mL dioxane was added and evaporated to provide 4-bromo-6-chloroquinolin-3-aminium hydrochloride. The product was mixed with 100 g NaI and 600 mL dry MeCN and refluxed overnight. The solvent was evaporated and the residue was partitioned between 500 mL EtOAc and a solution of 10 g NaHCO₃ in 500 mL water. The organic layer was separated, and the aqueous layer was extracted with EtOAc (2×200 mL). The combined organic layers were dried with MgSO₄ and evaporated to provide 6-chloro-4-iodoquinolin-3-amine as a tan solid. A dry 1 L round bottom flask was flushed with Ar and cooled to −78° C. in a dry ice/acetone bath. Dry THF (350 mL) was added followed by 188 mL 1.7 M t-BuLi/pentane with vigorous stirring. A solution of 25.8 g crude 6-chloro-4-iodoquinolin-3-amine in 350 mL dry THF was added dropwise to the stirred mixture. When addition was complete the reaction mixture was stirred at −78° C. for 5 min. Ultra dry acetone (50 mL) was added dropwise and the solution was stirred at −78° C. for 10 min after addition was complete. A solution of 20 g NH₄Cl in 200 mL water was added and the mixture was warmed up to room temperature, transferred to a separatory funnel containing 300 mL EtOAc. The organic layer was separated and the aqueous layer extracted with EtOAc (2×250 mL). The combined organic layers were dried with MgSO₄ and evaporated to a dark brown residue. The residue was partially purified by column chromatography on silica gel eluted with hexanes-EtOAc. All fractions containing (2-3) were combined and evaporated to give crude (2-3) as a red oil. A batch of crude ii) (ca. 2 g) obtained from a separate synthesis was added to this product, and the combined batches were dissolved in 50 mL EtOAc and filtered. The filtrate and washings were combined and concentrated to an oil which was diluted with 10 mL hot hexanes, treated dropwise with EtOAc until a clear solution formed, and allowed to evaporate at room temperature overnight in the fume hood. The oily mother liquor was removed and the solid was washed with minimum volumes of 3:1 hexanes-EtOAc. After recrystallization twice from hexanes-EtOAc, a first crop of pure (Compound (2)) was obtained as off-white crystals. All the mother liquor and washings were pooled and EtOAc (ca. 50 mL) was added to form a clear solution which was extracted with 0.5 N aq. HCl (4×100 mL). The aqueous layers were pooled and neutralized with 20% NaOH to pH 8. The resulting suspension was extracted with EtOAc (3×50 mL) and the combined organic layers were dried with MgSO₄ and evaporated to dryness. The residue was purified by column chromatography and two crystallizations from hexanes-EtOAc to provide a second crop of (2-3). A third crop (2-3) was obtained by fractional crystallization of the combined mother liquor and washings from hexanes-EtOAc.

¹H NMR (400 MHz, CDCl₃) δ: 1.93 (s, 6H), 3.21 (br, 1H, OH), 5.39 (br, 2H, NH₂), 7.29 (dd, 1H, J=2.0, 8.8 Hz), 7.83 (d, 1H, J=8.8 Hz), 7.90 (d, 1H, J=2.0 Hz), 8.21 (s, 1H). ¹³C NMR (100 MHz, CDCl₃) δ: 31.5, 76.5, 123.2, 124.6, 125.7, 127.5, 131.5, 131.9, 138.8, 141.5, 146.5. LC-MS: 236.9 (MH)⁺, 238.9 [(M+2)H]⁺.

Example 8. Synthesis of 2-(5-amino-7-chloro-2-p-tolylbenzoxazol-6-yl)propan-2-ol (Compound (12))

3-Methoxy-4-(trifluoroacetylamino)benzoic acid (12-1). To a suspension of 5.0 g 4-amino-3-methoxybenzoic acid in 200 mL EtOAc was added under stirring a solution of 5.0 mL (CF₃CO)₂O in 50 mL of EtOAc. After complete addition, the reaction mixture was further stirred at room temperature for 2 h. The solution was filtered, and the filtrate was evaporated to dryness. The residue was dissolved and evaporated twice in EtOAc. The final residue was dried under high vacuum to afford pure (12-1) as a white solid.

5-Methoxy-2-nitro-4-(trifluoroacetylamino)benzoic acid (12-2). A suspension of 7.55 g (12-1) in 80 mL 96% H₂SO₄ was stirred at room temperature until a homogeneous solution was formed. The solution was cooled with an ice bath under stirring while a solution of 2.03 g 90.6% fuming HNO₃ in 20 mL 96% H₂SO₄ was added dropwise under cooling. The temperature was maintained below 10° C. After complete addition, the mixture was further stirred for 10 min, and then slowly added onto 200 g ice under vigorous stirring. The mixture was saturated with NaCl and extracted with EtOAc (3×100 mL). The combined organic layer was washed with brine (2×50 mL), dried with Na₂SO₄, and then evaporated to give pure (12-2) as a light brown solid.

4-Amino-5-hydroxy-2-nitrobenzoic acid (12-3). A mixture of 6.94 g (12-2) in 35 mL 20% aqueous NaOH was stirred under argon at 100° C. overnight. The mixture was cooled to room temperature. To it was added dropwise 20 mL 12 N HCl under ice bath cooling. After complete addition, the solution was evaporated, and the residue was extracted with 200 mL absolute EtOH. The solid NaCl was filtered off, and the filtrate was evaporated to give the crude HCl salt of (12-3) as a dark grey solid.

4-Amino-5-hydroxy-2-nitrobenzoic acid ethyl ester (12-4). The above 6.95 g crude HCl salt of (12-3) was dissolved in 250 mL absolute EtOH. The solution was purged with dry HCl to nearly saturation, and then stirred at 80° C. for 36 h. The solvent was evaporated, and the residue was partitioned between 200 mL EtOAc and 200 mL brine. The aqueous layer was extracted with EtOAc (2×100 mL). The combined organic layer was dried with Na₂SO₄, acidified with 2 mL of HOAc, and then passed through a short silica gel column. The column was eluted with 1% HOAc/EtOAc. The combined yellow fraction was evaporated to give crude (12-4) as a red viscous oil.

5-Hydroxy-4-(4-methylbenzoylamino)-2-nitrobenzoic acid ethyl ester (12-5). A mixture of 2.26 crude (12-4) and 2.1 g p-toluoyl chloride in 25 mL 1,4-dioxane was stirred at 95° C. for 1.5 h. The solvent was removed, and the residue was evaporated twice with EtOH and then evaporated twice with EtOAc. The final residue was dried at 60° C. under high vacuum to give crude (12-5) as a tan solid.

2-Chloro-3-hydroxy-4-(4-methylbenzoylamino)-6-nitrobenzoic acid ethyl ester (12-6). A suspension of 3.35 g (12-5) in 100 mL dioxane was stirred until a clear solution was formed, and then 70 μL diisopropylamine (DIPA) was added. The solution was stirred at 50° C. while 1.96 mL SO₂Cl₂ was added. The reaction mixture was stirred under argon at 50° C. for 1 h, cooled to room temperature, diluted with 200 mL EtOAc, washed with water (3×100 mL), and dried with MgSO₄. The solvent was evaporated and the residue was dried at 60° C. under high vacuum to give crude (12-6) as a brown solid.

7-Chloro-5-nitro-2-(p-tolyl)benzoxazole-6-carboxylic acid ethyl ester (12-7). A mixture of 4.35 g crude (12-6) and 3.93 g Ph₃P in 50 mL dry THF was stirred at room temperature until a solution was formed. To the solution was added 6.7 mL 40% DEAD/toluene, and the mixture was stirred at 70° C. for 1 h. The mixture was diluted with 50 mL EtOH and evaporated. The residue was separated by silica gel column chromatography with hexane-EtOAc as eluent to give pure (12-7) as a white solid.

5-Amino-7-chloro-2-(p-tolyl)benzoxazole-6-carboxylic acid ethyl ester (12-8). A mixture of 1.17 g (12-7), 1.07 g iron powder and 25 mL glacial HOAc was heated at 60° C. under vigorous stirring for 3 h. The reaction mixture was diluted with 200 mL EtOAc. The slurry was passed through a celite pellet, and the celite was washed with EtOAc. The combined filtrates were passed through a short silica gel column, and the column was eluted with EtOAc. The combined yellow fractions were evaporated, and the residue was crystallized from hexanes-EtOAc to give pure (12-8) as a bright yellow solid.

2-(5-Amino-7-chloro-2-(p-tolyl)benzoxazol-6-yl)propan-2-ol (Compound (12)). A mixture of 7.0 mL 3.0 M MeMgCl/THF and 6 mL THF was protected under argon, and cooled in an ice bath with vigorous stirring. To it was added dropwise a solution of 886 mg (12-8) in 50 mL THF. After compete addition, the mixture was stirred at 0° C. for 5 min. To the mixture was added 100 mL saturated NH$_4$Cl with ice bath cooling and vigorous stirring. The organic layer was separated, and the aqueous layer was extracted with CH$_2$Cl$_2$ (DCM) (3×100 mL). The combined organic layers were dried with MgSO$_4$ and evaporated. The crude product was purified by silica gel column chromatography with MeOH-DCM as eluent and then crystallized from heptane/DCM to give pure (Compound (12)) as an off-white solid.

$^1$H NMR (400 MHz, CDCl$_3$) δ: 1.89 (s, 6H), 2.41 (s, 3H), 4.45 (br, 3H, NH$_2$ and OH), 6.81 (s, 1H), 7.27 (d, 1H, J=8.8 Hz), 8.07 (d, 1H, J=8.4 Hz). $^{13}$C NMR (100 MHz, CDCl$_3$) δ: 21.7, 31.0, 76.9, 106.2, 113.5, 124.0, 126.8, 127.6, 129.6, 140.9, 142.2, 142.9, 145.3, 164.1. LC-MS: 317.0 (MH)$^+$, 319.0 [(M+2)H]$^+$.

Example 9. Synthesis of 2-(5-amino-7-chloro-2-phenylbenzoxazol-6-yl)propan-2-ol (Compound (13))

4-Benzoylamino-5-hydroxy-2-nitrobenzoic acid ethyl ester (13-1). A mixture of 2.26 g crude 4-amino-5-hydroxy-2-nitrobenzoic acid ethyl ester (12-4) and 1.91 g benzoyl chloride in 25 mL 1,4-dioxane was stirred at 95° C. for 1 h. The solvent was removed and the residue was evaporated twice with EtOH. The residue was further evaporated twice with EtOAc, and then was dried at 60° C. under high vacuum to give crude (13-1) as a tan solid.

4-Benzoylamino-2-chloro-3-hydroxy-6-nitrobenzoic acid ethyl ester (13-2). A suspension of 3.23 g (13-1) in 100 mL dioxane was stirred until a clear solution was formed. To the solution was added 70 μL DIPA, and the solution was stirred to 50° C., followed by addition of 2.03 mL SO$_2$Cl$_2$. The reaction mixture was stirred under argon at 50° C. for 1 h, cooled to room temperature, diluted with 200 mL EtOAc, washed with water (3×100 mL), and then dried with MgSO$_4$. The solvent was evaporated and the residue was dried at 60° C. under high vacuum to give crude (13-2) as a brown solid.

7-Chloro-5-nitro-2-phenylbenzoxazole-6-carboxylic acid ethyl ester (13-3). A mixture of crude 3.74 g (13-2) and 3.93 g Ph$_3$P in 50 mL dry THF was stirred at room temperature until a solution was formed. To the solution was added 6.7 mL 40% DEAD/toluene, and the mixture was stirred at 70° C. for 1 h. The mixture was diluted with EtOH and evaporated. The residue was separated by silica gel column chromatography with hexane-EtOAc as eluent to give (13-3) as a white solid.

5-Amino-7-chloro-2-phenylbenzoxazole-6-carboxylic acid ethyl ester (13-4). A mixture of 0.89 g (13-3), 2.0 g iron powder and 25 mL glacial HOAc was heated at 60° C. under vigorous stirring for 1.5 h. The mixture was diluted with 200 mL EtOAc. The slurry was passed through a celite pellet, and the celite was washed with EtOAc. The combined filtrates were pass through a short silica gel column, and the column was eluted with EtOAc. The combined yellow fractions were evaporated, and the residue was crystallized from hexanes-EtOAc to give pure (13-4) as a bright yellow solid.

2-(5-Amino-7-chloro-2-phenylbenzoxazol-6-yl)propan-2-ol (Compound (13)). A mixture of 6 mL 3.0 M MeMgCl/THF and 6 mL THF was protected under argon, and cooled in an ice bath with vigorous stirring. To it was added dropwise a solution of 638 mg (13-4) in 50 mL THF. After complete addition, the mixture was stirred at 0° C. for 5 min. To the mixture was added 100 mL saturated NH$_4$Cl with cooling and vigorous stirring. The organic layer was separated, and the aqueous layer was extracted with DCM (3×100 mL). The combined organic layers were dried with MgSO$_4$ and evaporated. The crude product was purified by silica gel column chromatography with MeOH-DCM as eluent, and then crystallized from heptane-DCM to give pure (Compound (13)) as a pale yellow solid.

$^1$H NMR (400 MHz, CDCl$_3$) δ: 1.92 (s, 6H), 4.69 (br, 3H, NH$_2$ and OH), 6.87 (s, 1H), 7.48-7.54 (3H), 8.21 (m, 2H). $^{13}$C NMR (100 MHz, CDCl$_3$) δ: 31.0, 77.0, 106.3, 113.6, 126.8, 126.9, 127.7, 128.9, 131.6, 140.9, 143.0, 145.4, 163.9. LC-MS: 303.1 (MH)$^+$, 305.0 [(M+2)H]$^+$.

Example 10. Synthesis of 2-(6-amino-4-chloro-3-cyclopropylbenzisoxazol-5-yl)propan-2-ol (Compound (14))

(2-Chloro-4,6-dimethoxyphenyl)cyclopropylmethanone (14-1). A solution of 28.28 g 1-chloro-3,5-dimethoxybenzene and 17.8 mL cyclopropanecarbonyl chloride in 300 mL dry 1,2-dichloroethane (DCE) was protected with argon, and cooled in a dry ice/acetone bath to −30 to −40° C. To it was added in portions 32.4 g AlCl$_3$ powder under vigorous stirring. After complete addition, the solution was stirred at −30 to −40° C. for 30 min, and then allowed to warm up to room temperature. After further stirring at room temperature for 20 min, the mixture was added onto 1 kg ice under stirring. The mixture was extracted with ether (3×300 mL). The combined organic layers were dried with MgSO$_4$ and evaporated. The residue was separated by column chromatography with hexanes/EtOAc as eluent to give pure (14-1) as a white solid.

(2-Chloro-6-hydroxy-4-methoxyphenyl)cyclopropylmethanone (14-2). A solution of 13.45 g (14-1) in 100 mL dry DCM was protected with argon, and cooled at −78° C. (dry ice/acetone bath) under stirring. To it was added 62 mL 1 M BBr$_3$/DCM. After complete addition, the mixture was further stirred at −78° C. for 1 h. To the mixture was slowly injected 50 mL MeOH under dry ice/acetone bath cooling and vigorous stirring. After complete injection, the mixture was further stirred at −78° C. for 10 min, and then allowed to warm up to room temperature. The mixture was partitioned between 500 mL DCM and 500 mL brine. The organic layer was separated, washed with brine (2×100 mL), and then mixed with a solution of 4.0 g NaOH in 300 mL water. After stirring at room temperature for 1 h, the mixture was acidified with 10 mL 12 N aqueous HCl with stirring. The organic layer was separated, dried with MgSO$_4$, and evaporated. The residue was separated by silica gel column chromatography with hexanes-EtOAc as eluent to give (14-2) as a white solid.

(E)- and (Z)-(2-Chloro-6-hydroxy-4-methoxyphenyl)cyclopropylmethanone oxime (14-3). A mixture of 10.38 g (14-2) and 15.95 g NH$_2$OH.HCl in 150 mL dry pyridine was protected under argon, and stirred at 80° C. for 20 h. The solvent was evaporated, and the residue was partitioned between 400 mL 0.1 N HCl/brine and 400 mL Et$_2$O. The organic layer was separated, washed with water (2×50 mL), dried with MgSO$_4$ and evaporated. The residue was crystallized from heptane-EtOAc to give pure (14-3) as a white solid.

(E)- and (Z)-(2-Chloro-6-hydroxy-4-methoxyphenyl)cyclopropylmethanone 0-acetyl oxime (14-4). To a suspension of 9.75 g (14-3) in 40 mL EtOAc was added 6.5 mL Ac$_2$O under stirring at room temperature. After complete addition, the mixture was stirred at room temperature for 1 h. To the mixture was added 50 mL MeOH and 20 mL pyridine, and the mixture was stirred at room temperature for 30 min. The solvent was evaporated, and the residue was partitioned between 300 mL 1 N HCl/brine and 300 mL EtOAc. The organic layer was separated, washed with water (2×50 mL), dried with MgSO$_4$ and evaporated to give crude (14-4) as a light brown oil.

4-Chloro-3-cyclopropyl-6-methoxybenzisoxazole (14-5). Crude (14-4) was protected under argon, and heated in an oil bath at 150° C. for 3 h. The crude product was purified by silica gel column chromatography using hexanes-EtOAc as eluent to give pure (14-5) as a light tan solid.

4-Chloro-3-cyclopropylbenzisoxazol-6-ol (14-6). A solution of 7.61 g (14-5) in 75 mL dry DCM was protected under argon, and cooled to −78° C. in a dry ice/acetone bath. To it was added dropwise 80 mL 1 M BBr$_3$ in DCM with vigorous stirring. After compete addition, the mixture was allowed to warm to room temperature, and then stirred at room temperature for 1 h. The mixture was again cooled to −78° C. in a dry ice/acetone bath. To the mixture was added 20 mL MeOH under vigorous stirring. After complete addition, the reaction mixture was allowed to warm to room temperature, and then partitioned between 1.5 L brine and 1.5 L EtOAc. The organic layer was separated, and the aqueous layer was extracted with EtOAc (2×300 mL). The combined organic layers were dried with MgSO$_4$, and passed through a short silica gel column that was eluted with EtOAc. The combined fractions were evaporated to give pure (14-6) as a light brown oil, which solidified upon standing.

4-Chloro-3-cyclopropylbenzisoxazol-6-yltrifluoromethanesulfonate (14-7). A mixture of 6.88 g (14-6) and 4 mL pyridine in 50 mL DCM was protected under argon and stirred at 0° C. in an ice bath. To it was added dropwise 6.73 mL Tf$_2$O with vigorous stirring. After complete addition, the mixture was allowed to warm up to room temperature. After further stirring for 10 min at room temperature, the mixture was partitioned between 200 mL 1 N HCl and 300 mL DCM. The organic layer was separated, washed sequentially with 100 mL 1 N HCl, 100 mL brine, 100 mL 5% aqueous NaHCO$_3$ and 100 mL brine, dried with MgSO$_4$ and then evaporated. The residue was purified by column chromatography with hexanes-EtOAc as eluent to give pure (14-7) as an off-white solid.

tert-Butyl (4-chloro-3-cyclopropylbenzisoxazol-6-yl)carbamate (14-8). A mixture of 8.02 g (14-7), 2.87 g tert-butyl carbamate, 2.37 g tBuONa, 1.08 g tris(dibenzylideneacetone) dipalladium(0) (Pd$_2$dba$_3$), 2.0 g 2-di-tert-butylphosphino-2',4',6'-triisopropylbiphenyl (t-butyl Xphos) and 7 g 4 Å molecular sieves in 120 mL dry toluene was purged with argon, and then heated at 110° C. with vigorous stirring for 20 min. The reaction mixture was diluted with 300 mL EtOAc, and passed through a celite pellet which was then washed with EtOAc. The combined solutions were evaporated and the residue was separated by silica gel column chromatography with hexanes-EtOAc as eluent to give crude (14-8) as a light brown oil.

6-Amino-4-chloro-3-cyclopropylbenzisoxazole (14-9). The 4.09 g crude (14-8) was dissolved in 10 mL DCM, followed by addition of 10 mL TFA. The mixture was stirred at room temperature for 30 min. The solvent was removed, and the residue was partitioned between 200 mL DCM and 200 mL 10% NaHCO$_3$. The organic layer was separated, washed with water (2×50 mL), dried with MgSO$_4$ and evaporated. The residue was separated by silica gel column chromatography with hexanes-EtOAc as eluent to give pure (14-9) as a white solid.

5-Bromo-4-chloro-3-cyclopropylbenzisoxazol-6-ylamine (14-10) and 7-bromo-4-chloro-3-cyclopropylbenzisoxazol-6-ylamine (16-1). To a solution of 1.96 g (14-9) in 100 mL DCM was added 1.67 g solid NBS in small portions under vigorous stirring at room temperature. After complete addition, the mixture was further stirred at room temperature for 30 min, diluted with 100 mL DCM, washed sequentially with 10% aqueous NaHSO$_3$ (200 mL) and water (2×200 mL), dried with MgSO$_4$, and evaporated to give a 1:1 mixture of (14-10) and (16-1) as a tan oil, which solidified on standing.

6-Amino-4-chloro-3-cyclopropylbenzisoxazole-5-carbonitrile (14-11) and 6-amino-4-chloro-3-cyclopropylbenzisoxazole-7-carbonitrile (16-2). A suspension of 2.72 g of a mixture of (14-10) and (16-1), 1.70 g CuCN and 3.62 g CuI in 25 mL dry DMF was purged with argon, and then heated at 110° C. in an oil bath with vigorous stirring for 15 h. The mixture was cooled to room temperature. To it was added 100 mL 30% aqueous NH$_3$. After stirring at room temperature for 1 h, the mixture was diluted with 300 mL water, and extracted with EtOAc (2×500 mL). The combined organic layers were washed with water (3×200 mL), dried with MgSO$_4$ and evaporated. The residue was separated by silica gel column chromatography with hexanes-EtOAc as eluent to give (14-11) as a light yellow solid, and (16-2) as a light tan solid.

4-Chloro-5-cyano-3-cyclopropyl-6-(tritylamino)benzisoxazole (14-12). To a mixture of 435 mg (14-11) and 700 µL TEA in 20 mL DCM was added 1.09 g solid trityl chloride in small portions under stirring at room temperature. After complete addition, the mixture was further stirred at room temperature for 30 min. The reaction mixture was diluted with 300 mL DCM, washed with water (4×200 mL), dried with MgSO$_4$ and then evaporated. The residue was separated by silica gel column chromatography with DCM as eluent to give pure (14-12) as a white solid.

4-Chloro-3-cyclopropyl-6-(tritylamino)benzisoxazole-5-carbaldehyde (14-13). A solution of 481 mg (14-12) in 13 mL dry THF was cooled in an ice bath with stirring. To the solution was added dropwise 7 mL 1 M DIBAL/toluene. After complete addition, the reaction mixture was stirred at 0° C. for 2.5 h. The reaction was quenched with 100 mL 1% aqueous tartaric acid, and the mixture was extracted with DCM (3×100 mL). The organic layer was washed with water (3×100 mL), dried with MgSO$_4$ and evaporated. The residue was dissolved in DCM and adsorbed onto silica gel. The mixture was air-dried and separated by silica gel column chromatography with hexanes-EtOAc as eluent to give crude (14-13) as a yellow solid.

1-[4-Chloro-3-cyclopropyl-6-(tritylamino)benzisoxazol-5-yl]ethanol (14-14). The above 257.8 mg crude (14-13) was dissolved in 10 mL dry THF, and the solution was added to a mixture of 2.0 mL 3 M MeMgCl/THF and 2 mL dry THF at 0° C. (ice bath) with stirring. After complete addition, the mixture was further stirred at 0° C. for 5 min, and then quenched with 100 mL 5% NH$_4$Cl under ice bath cooling. The mixture was extracted with DCM (3×100 mL), dried with MgSO$_4$ and evaporated. The residue was separated by silica gel column chromatography with hexanes-EtOAc as eluent to give pure (14-14) as a white solid.

1-[4-Chloro-3-cyclopropyl-6-(tritylamino)benzisoxazol-5-yl]ethanone (14-15). To a solution of 150.5 mg (14-14) in 20 mL dry DCM was added 271 mg solid Dess-Martin periodinane (1,1,1-triacetoxy-1,1-dihydro-1,2-benziodoxol-3(1H)-one, DMP) in small portions at room temperature under vigorous stirring. After complete addition, the reaction mixture was further stirred at room temperature for 10 min. The reaction mixture was diluted with 300 mL DCM, washed with water (4×200 mL), dried with MgSO$_4$ and evaporated. The residue was separated by silica gel column chromatography with hexanes-EtOAc as eluent to give pure (14-15) as a pale yellow solid.

1-(6-Amino-4-chloro-3-cyclopropylbenzisoxazol-5-yl)ethanone (14-16). To a solution of 182 mg (14-15) in 20 mL dry DCM was added dropwise 2 mL TFA under stirring at room temperature. The solution was stirred at room temperature for 10 min, diluted with 200 mL DCM, washed with water (4×100 mL), dried with MgSO$_4$ and evaporated to give crude (14-16) as a white solid.

2-(6-Amino-4-chloro-3-cyclopropylbenzisoxazol-5-yl)propan-2-ol (Compound (14)). The 174.7 mg crude (14-16) was dissolved in 20 mL dry THF, and the solution was added dropwise to a well stirred mixture of 2.5 mL 3M MeMgCl/THF and 2 mL THF at 0° C. (ice bath). After complete addition, the mixture was further stirred at 0° C. for 5 min. To it was added dropwise 100 mL 5% aqueous NH$_4$Cl under ice bath cooling and stirring. The mixture was extracted with DCM (3×100 mL), dried with MgSO$_4$ and evaporated. The crude product was purified by silica gel column chromatography with MeOH-DCM as eluent and then crystallized from heptane-DCM to give pure (Compound (14)) as a white solid.

$^1$H NMR (400 MHz, CDCl$_3$) δ: 1.10 (m, 2H), 1.20 (m, 2H), 1.91 (s, 6H), 2.18 (m, 1H), 4.28 (br, 2H, NH$_2$), 6.57 (s, 1H). $^{13}$C NMR (100 MHz, CDCl$_3$) δ: 8.68, 9.35, 30.0, 77.4, 97.4, 121.2, 125.1, 133.1, 145.7, 149.3, 166.4. LC-MS: 266.9 (MH)$^+$, 269.0 [(M+2)H]$^+$.

Example 11. Synthesis of 2-(5-amino-7-chloro-3-cyclopropylbenzisoxazol-6-yl)propan-2-ol (Compound (15))

Cyclopropanecarboxylic acid methoxymethylamide (15-1). A suspension of 9.75 g N, O-dimethylhydroxylamine hydrochloride and 9.7 mL pyridine in 200 mL DCM was stirred at room temperature for 10 min, and then cooled in an ice bath with stirring. To the suspension was added dropwise a solution of 9.03 mL cyclopropanecarbonyl chloride in 40 mL DCM with vigorous stirring. After complete addition, the mixture was stirred at 0° C. for 30 min, and then at room temperature for 1 h. The solution was diluted with 100 mL DCM, washed with brine (3×200 mL), and dried with MgSO$_4$. The solvent was evaporated, and the residue vacuum distilled. The fraction collected at 43-45° C./1 mmHg gave (15-1) as a colorless liquid.

2-(3-Chloro-4-fluorophenyl)-1,1,1,3,3,3-hexamethyldisilazane (15-2). A solution of 7.3 g 3-chloro-4-fluoroaniline in 100 mL dry THF was protected under argon and cooled to −78° C. (dryice/acetone bath). To the solution was slowly added 21 mL 2.5 M nBuLi in hexanes with vigorous stirring. After complete addition, the suspension was further stirred at −78° C. for 10 min. To the latter was slowly added 6.65 mL chlorotrimethylsilane (TMSCl) under vigorous stirring. After complete addition, the mixture was further stirred at −78° C. for 30 min. To the latter was again added 24 mL 2.5 M nBuLi, followed by 7.65 mL TMSCl under vigorous stirring. The mixture was stirred at −78° C. for 30 min, and then allowed to warm to room temperature. The solvent was removed and the residue was vacuum distilled. The fractions collected below 95° C./1 mmHg were pooled to give (15-2) as a colorless liquid.

(5-Amino-3-chloro-2-fluorophenyl)(cyclopropyl)methanone (15-3). A solution of 9.11 g (15-2) in 100 mL dry THF was cooled to −78° C. in a dry ice/acetone bath under argon. To it was added dropwise 15.7 mL 2.5 M nBuLi in hexanes under vigorous stirring. After complete addition, the mixture was stirred at −78° C. for 2 h. To the mixture was added slowly 5.2 g (15-1) under stirring. After complete addition, the reaction mixture was stirred at −78° C. for 1 h, and then allowed to warm up to room temperature. The reaction mixture was poured into 400 mL cold 1:1 MeOH/1 N HCl under stirring. After further stirring for 30 min, the mixture was extracted with DCM (3×200 mL). The combined organic layers were dried with MgSO$_4$ and evaporated to give crude (15-3) as a light brown oil.

N-[3-Chloro-5-(cyclopropylcarbonyl)-4-fluorophenyl]acetamide (15-4). Crude (15-3) (6.09 g) was dissolved in 100 mL DCM. To it were added sequentially 6 mL acetic anhydride (Ac$_2$O) and 9.6 mL triethylamine (TEA) with ice bath cooling and vigorous stirring. After complete addition, the reaction mixture was further stirred at room temperature for 1 h, diluted with 200 mL DCM, and washed with 0.1 N HCl (3×200 mL). The organic layer was dried with MgSO$_4$ and evaporated. The crude product was purified by silica gel column chromatography with hexanes-EtOAc as eluent and then crystallized from hexanes-EtOAc to give pure (15-4) as a white solid.

(E)- and (Z)—N-{3-Chloro-5-[cyclopropyl(hydroxyimino)methyl]-4-fluorophenyl}acetamide (15-5). A mixture of 2.28 g (15-4), 3.1 g NH$_2$OH.HCl, 30 mL pyridine and 30 mL EtOH was stirred at 50° C. for 22 h. EtOH was evaporated, and the residue was partitioned between 200 mL Et$_2$O and 200 mL 1 N HCl/brine. The organic layer was separated, washed with water (2×20 mL), dried with MgSO$_4$ and evaporated to give pure (15-5) as an off-white amorphous solid.

N-(7-Chloro-3-cyclopropylbenzisoxazol-5-yl)acetamide (15-6). A solution of 2.01 g (15-5) in 40 mL dry DMF was protected with argon and stirred with ice bath cooling. To the solution was added in portions 1.48 g 60% NaH in mineral oil under vigorous stirring. After complete addition, the reaction mixture was stirred at room temperature for 1.5 h, and then was carefully added into a mixture of 300 mL saturated NaHCO$_3$ and 300 mL EtOAc under stirring. The organic layer was separated, washed with water (3×50 mL), dried with MgSO$_4$ and evaporated. The residue was separated by column chromatography with hexanes-EtOAc as eluent to give pure (15-6) as a white solid.

tert-Butyl acetyl(7-chloro-3-cyclopropylbenzisoxazol-5-yl)carbamate (15-7). A mixture of 789.3 mg (15-6), 808 mg Boc₂O and 38 mg DMAP in 40 mL dry DCM was stirred at room temperature for 1 h. Solvent was evaporated to give crude (15-7) as a white solid.

tert-Butyl (7-chloro-3-cyclopropylbenzisoxazol-5-yl)carbamate (15-8). The above crude (15-7) was dissolved in 100 mL MeOH. The solution was basified with 0.1 mL 25 wt. % NaOMe/MeOH, and then stirred at room temperature for 30 min. To the solution was added 1 g solid NH₄Cl, and the solvent was evaporated. The residue was partitioned between 300 mL 0.1 N HCl/brine and 300 mL EtOAc. The organic layer was separated, washed sequentially with 100 mL 0.1 N HCl/brine, 100 mL water, 100 mL saturated NaHCO₃ and 100 mL water, dried with MgSO₄ and evaporated. The residue was crystallized from heptane-EtOAc to give pure (15-8) as a white solid.

5-[(tert-Butoxycarbonyl)amino]-7-chloro-3-cyclopropyl-benzisoxazole-6-carboxylic acid (15-9). A solution of 770 mg (15-8) in 50 mL dry THF was protected under argon, and stirred with dry ice/acetone bath cooling. To the solution was added dropwise 5.9 mL 1.7 M tBuLi/pentane under vigorous stirring. After complete addition, the mixture was further stirred at −78° C. for 5 min. To the latter was added all at once 7.2 g freshly crushed dry ice under vigorous stirring. The mixture was stirred at −78° C. for 5 min, and then allowed to warm up to room temperature. The reaction mixture was partitioned between 300 mL 1 N HCl/brine and 300 mL EtOAc. The organic layer was separated, washed with 100 mL 0.1 N HCl/brine, dried with MgSO₄ and evaporated. The residue was separated by silica gel column chromatography with hexanes/EtOAc/HOAc as eluent to give (15-9) as an off-white foam.

Methyl 5-[(tert-butoxycarbonyl)amino-7-chloro-3-cyclopropylbenzisoxazole-6-carboxylate (15-10). A solution of 815 mg (15-9) and 5 mL MeOH in 10 mL DCM was stirred with ice bath cooling. To the solution was added dropwise 2.31 mL 2 M trimethylsilyldiazomethane (TMSCHN₂) in hexanes under stirring. After complete addition, the solution was stirred at room temperature for 10 min and evaporated. The residue was dissolved in 100 mL DCM, and the solution was passed through a short silica gel column. The column was eluted with MeOH-DCM, and the combined fractions were evaporated to give (15-10) as an off-white solid.

Methyl 5-amino-7-chloro-3-cyclopropylbenzisoxazole-6-carboxylate (15-11). A solution of 813 mg (15-10) in 10 mL DCM was stirred with ice bath cooling. To it was added dropwise 10 mL TFA with stirring. After complete addition, the mixture was stirred at room temperature for 30 min and evaporated. The residue was partitioned between 200 mL saturated NaHCO₃ and 200 mL EtOAc. The organic layer was separated, washed with water (2×50 mL), dried with MgSO₄, and evaporated to give (15-11) as a yellow oil, which solidified on standing.

2-(5-Amino-7-chloro-3-cyclopropylbenzisoxazol-6-yl)propan-2-ol (Compound (15)). A solution of 7.73 mL 3M MeMgCl/THF in 6 mL dry THF was protected under argon and stirred with ice bath cooling. To it was added dropwise a solution of 620 mg (15-11) in 50 mL dry THF under vigorous stirring. After complete addition, the mixture was allowed to warm and then stirred at room temperature for 1 h. The mixture was added carefully into 300 mL saturated aqueous NH₄Cl under stirring and ice bath cooling. The mixture was extracted with DCM (3×100 mL), dried with MgSO₄ and evaporated. The crude product was purified by silica gel column chromatography with MeOH-DCM as eluent, and then crystallized from heptane-DCM to give pure (Compound (15)) as an off-white solid.

$^1$H NMR (400 MHz, CDCl₃) δ: 1.10 (m, 2H), 1.15 (m, 2H), 1.91 (s, 6H), 2.09 (m, 1H), 4.33 (br, 3H, NH₂ and OH), 6.70 (s, 1H). $^{13}$C NMR (100 MHz, CDCl₃) δ: 7.11, 7.25, 30.7, 77.1, 105.6, 113.7, 120.4, 132.5, 144.4, 155.4, 160.5. LC-MS: 267.1 (MH)⁺, 269.1 [(M+2)H]⁺.

Example 12. Synthesis of 2-(6-amino-4-chloro-3-cyclopropylbenzisoxazol-7-yl)propan-2-ol (Compound (16))

1-(6-Amino-4-chloro-3-cyclopropyl-benzisoxazol-7-yl)ethanone (16-3). To a mixture of 636 mg (16-2) and 43 mg CuI was slowly added 8.16 mL 3 M MeMgCl/THF under stirring and ice bath cooling. The suspension was protected under argon, and heated at 70° C. in an oil bath for 15 min. The mixture was cooled to 0° C. in an ice bath. To it was added 136 mL MeOH, followed by 2.17 g solid NH₄Cl and 13.6 mL water. The mixture was warmed to room temperature with stirring to give a clear solution, which was adsorbed on silica gel, air-dried and separated by silica gel column chromatography with hexanes-EtOAc as eluent to give (16-3) as a yellow solid.

2-(6-Amino-4-chloro-3-cyclopropylbenzisoxazol-7-yl)propan-2-ol (Compound (16)). A mixture of 1.54 mL 3 M MeMgCl/THF and 5 mL dry THF was protected under argon and stirred with ice bath cooling. To it was added a solution of 387.1 mg (16-3) in 15 mL dry THF under vigorous stirring. After complete addition, the solution was further stirred at 0° C. for 20 min. To the solution was added 100 mL saturated aqueous NH₄Cl with ice bath cooling and vigorous stirring. The mixture was warmed to room temperature and extracted with DCM (3×100 mL). The combined organic layers were dried with MgSO₄ and evaporated. The crude product was purified by silica gel column chromatography with MeOH-DCM as eluent, and crystallized from heptane-DCM to give pure (Compound (16)) as a light tan solid.

$^1$H NMR (400 MHz, CDCl₃) δ: 1.12 (m, 2H), 1.18 (m, 2H), 1.78 (s, 6H), 2.17 (m, 1H), 4.86 (br, 2H, NH₂), 6.60 (s, 1H). $^{13}$C NMR (100 MHz, CDCl₃) δ: 8.81, 9.26, 30.1, 74.1, 112.7, 114.4, 121.8, 131.3, 143.8, 148.6, 166.1. LC-MS: 267.0 (MH)⁺, 268.9 [(M+2)H]⁺.

EQUIVALENTS

Those skilled in the art will recognize, or be able to ascertain using no more than routine experimentation, many equivalents to the specific embodiments and methods described herein. Such equivalents are intended to be encompassed by the scope of the present invention.

All patents, patent applications, and literature references cited herein are hereby expressly incorporated by reference.

REFERENCES

Aldini, G. et al., "The carbonyl scavenger carnosine ameliorates dyslipidaemia and renal function in Zucker obese rats," L. Cell Med. 15: 1339-1354 (2010).

Batista, T. M. et al., "Age-dependent changes in rat lacrimal gland anti-oxidant and vesicular related protein expression profiles," Molecular Vision 18: 194-202 (2012).

Bartoli, M. L. et al., Mediators Of Inflammation, Article 891752.

Buddi, R. et al., "Evidence of Oxidative Stress in Human Corneal Diseases," J. of Histochem & Cytochem 50: 341-351 (2002).

Fitzmaurice, A. G. et al., "Aldehyde dehydrogenase inhibition as a pathogenic mechanism in Parkinson's disease," PNAC 110: 636-41 (2013).

Hassan, S. Z. et al., "Oxidative stress in systemic lupus erythematosus and rheumatoid arthritis patients: relationship to disease manifestations and activity," Int. J. Rheum. Dis. 14: 325-31 (2011).

Jafari, M. et al., "Evaluation of plasma, erythrocytes, and bronchoalveolar lavage fluid antioxidant defense system in sulfur mustard-injured patients," Clinical Toxicology 48: 184-192 (2010).

Jordan et al., WO 2006/127945.

Kenney, M. C. et al., "The Cascade Hypothesis of Keratoconus," Contact Lens & Anterior Eye 26: 139-146 (2003).

Kamino, K. et al., Biochem Res Commun. 273: 192-6 (2000).

Leibundgut, G., "Oxidation-specific epitopes and immunological responses: Translational biotheranostic implications foir atherosclerosis," Current Opinion in Pharmacology 13: 168-179 (2013).

Maeda, A. et al., "Primary amines protect against retinal degeneration in mouse models of retinopathies," Nature Chemical Biology 8: 170-178 (2012).

Marnett, L. J., "Oxy radicals, lipid peroxidation and DNA damage," Toxicology 181-182: 219-222 (2002).

Nakamura, S. et al., "Involvement of Oxidative Stress on Corneal Epithelial Alterations in a Blink-Suppressed Dry Eye," Investigative Ophthalmology & Visual Science 48: 1552-1558 (2007).

Negre-Salvayre, A. et al., "Advanced lipid peroxidation end products in oxidative damage to proteins. Potential role in diseases and therapeutic prospects for the inhibitors," British Journal of Pharmacology 153: 6-20 (2008).

Niwa, Y. et al., "Protein oxidative damage in the stratum corneum: evidence for a link between environmental oxidants and the changing prevalence and nature of atopic dermatitis in Japan," Br. J. Dermatol. 149: 248-254 (2003).

Pal, A. et al., "Sulfur mustard analog induces oxidative stress and activates signaling cascades in the skin of SKH-1 hairless mice," Free Radic Biol Med. 47: 1640-1651 (2009).

Palczewski, et al. US2012/0295895.

Reed, T. T., "Lipid Peroxidation and neurodegenerative disease," Free Radic Biol Med. 51: 1302-19, (2011).

Rizzo, W. B. et al., "Ichtyosis in Sjogren-Larsson syndrome reflects defective barrier function due to abnormal lamellar body structure and secretion," Arch Dermatol Res 302: 443-451 (2010).

Sciuto, A. M. et al., "Therapeutic treatments of phosgene-induced lung injury," Inhal Toxicol. 16: 565-80 (abstract) (2004).

Sikar, A. A. et al., "Nitric oxide and malondialdehyde levels in plasma and tissue of psoriasis patients," J. Eur Acad Dermatol Venereol 26: 833-7 (2012).

Tewari-Singh, N. et al., "Silibinin Attenuates Sulfur Mustard Analog-Induced Skin Injury by Targeting Multiple Pathways Connecting Oxidative Stress and Inflammation," PLoS One 7: e46149 (2009).

Tikly, M. et al., "Lipid peroxidation and trace elements in systemic sclerosis," Clin. Rheumatol 25: 320-4 (2006).

Wood, P. L. et al., "Neurotoxicity of reactive aldehydes: The concept of 'aldehyde load' as demonstrated by neuroprotection with hydroxylamines," Brain Research 1095: 190-199 (2006).

Wood, P. L., et al., "The concept of aldehyde load in neurodegenerative mechanisms: Cytotoxicity of the polyamine degradation products hydrogen peroxide, acrolein, 3-aminopropanal, 3-acetamidopropanal and 4-aminobutanal in a retinal ganglion cell line," Brain Res. 1145: 150-6 (2007).

Zarkovic, K., "4-hydroxynonenal and neurodegenerative disease," Mol Aspects Med. 24: 293-303 (2003).

Zhou et al., "Mechanisms for the Induction of HNE- MDA- and AGE-adducts, RAGE and VEGF in Retinal Pigment Epithelial Cells," Exp. Eye Res. 80: 567-80 (2005).

We claim:

1. A method of treating scleritis, comprising:
administering to a subject in need thereof a therapeutically effective amount of a compound of formula (I):

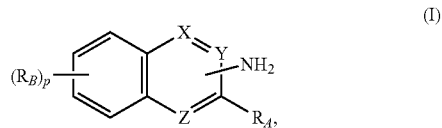

or a pharmaceutically acceptable salt thereof, wherein,
X is CH; Z is N; and Y is C with the —$NH_2$ attached;
p is 0, 1, 2, or 3;
each $R_B$ is independently a halogen, hydroxyl, carbamoyl, amino, or aryl;
$R_A$ is

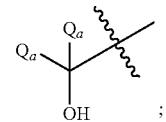

and
each $Q_a$ is independently a $C_1$-$C_6$ straight chain alkyl.

2. The method of claim 1, wherein p is 1.
3. The method of claim 1, wherein each $Q_a$ is methyl.
4. The method of claim 1, wherein $R_B$ is a halogen.
5. The method of claim 4, wherein the halogen is chlorine or fluorine.
6. The method of claim 5, wherein the halogen is chlorine.
7. The method of claim 1, wherein the compound is present at a concentration of about 0.05-10% w/v.
8. The method of claim 1, wherein the compound is present at a concentration of about 0.1-5% w/v.
9. The method of claim 1, wherein the compound is present at a concentration of about 0.1-2% w/v.
10. The method of claim 1, wherein the compound is present at a concentration of about 0.1-1.0% w/v.
11. The method of claim 1, wherein the compound is present at a concentration of about 0.09-0.5% w/v.
12. The method of claim 1, wherein the compound is present in an admixture with a cyclodextrin.
13. The method of claim 12, wherein the cyclodextrin comprises a β-cyclodextrin or a pharmaceutically acceptable salt thereof.
14. The method of claim 13, wherein the β-cyclodextrin is selected from the group consisting of sulfobutylether-β-cyclodextrin, 2-hydroxypropyl-β-cyclodextrin, and 3-hydroxypropyl-β-cyclodextrin.
15. The method of claim 14, wherein the β-cyclodextrin is sulfobutylether-β-cyclodextrin or a pharmaceutically acceptable salt thereof.

16. The method of claim 15, wherein the salt of sulfobutylether-β-cyclodextrin is sulfobutylether-β-cyclodextrin sodium salt.

17. The method of claim 16, wherein the sulfobutylether-β-cyclodextrin sodium salt is present at a concentration of about 0.01-30% w/v.

18. The method of claim 1, wherein the sulfobutylether-β-cyclodextrin is present at a concentration of about 2-25% w/v.

19. The method of claim 10, wherein the sulfobutylether-β-cyclodextrin is present at a concentration of about 6-20% w/v.

20. The method of claim 1, wherein for the compound of formula (I):
each $Q_a$ is methyl;
$R_B$ is halogen; and
p is 1.

21. The method of claim 1, wherein the compound is

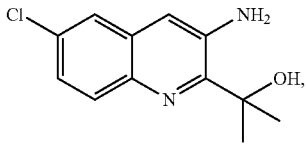 [SMILES: CC(C)(O)c1nc2ccc(Cl)cc2cc1N]

or a pharmaceutically acceptable salt thereof.

22. The method of claim 21, wherein the subject is a human and the compound is administered topically to one or both eyes of the subject.

23. The method of claim 19, wherein the compound is

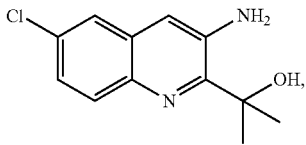 [SMILES: CC(C)(O)c1nc2ccc(Cl)cc2cc1N]

or a pharmaceutically acceptable salt thereof.

24. The method of claim 20, wherein the compound is administered topically to one or both eyes of the subject as an aqueous composition comprising the compound, and a cyclodextrin or a pharmaceutically acceptable salt thereof.

25. The method of claim 24, wherein the cyclodextrin is a β-cyclodextrin or a pharmaceutically acceptable salt thereof.

26. The method of claim 25, wherein the β-cyclodextrin is sulfobutylether-β-cyclodextrin, hydroxypropyl-β-cyclodextrin, or a pharmaceutically acceptable salt thereof.

27. The method of claim 26, wherein the β-cyclodextrin is hydroxypropyl-β-cyclodextrin, or a pharmaceutically acceptable salt thereof.

28. The method of claim 27, wherein the hydroxypropyl-β-cyclodextrin is 2-hydroxypropyl-β-cyclodextrin, 3-hydroxypropyl-β-cyclodextrin, or a pharmaceutically acceptable salt thereof.

29. The method of claim 26, wherein the β-cyclodextrin is sulfobutylether-β-cyclodextrin, or a pharmaceutically acceptable salt thereof.

30. The method of claim 29, wherein the sulfobutylether-β-cyclodextrin is present at a concentration of about 0.01%-30% w/v.

31. The method of claim 30, wherein the sulfobutylether-β-cyclodextrin is present at a concentration of about 5%-25% w/v.

32. The method of claim 31, wherein the compound is present at a concentration of about 0.09-0.5% w/v.

33. The method of claim 31, wherein the compound is present at a concentration of about 0.08-1% w/v.

34. The method of claim 31, wherein the compound is present at a concentration of about 0.06-5% w/v.

35. The method of claim 31, wherein the compound is present at a concentration of about 0.1-5% w/v.

36. The method of claim 31, wherein the compound is present at a concentration of about 0.2-2.0% w/v.

37. The method of claim 31, wherein the compound is present at a concentration of about 0.1-1.0% w/v.

38. The method of claim 22, wherein the compound is present at a concentration of 0.08%-1.0% w/v; and the cyclodextrin is sulfobutylether-β-cyclodextrin, wherein the sulfobutylether-β-cyclodextrin is present at 6%-12% w/v.

39. The method of claim 38, wherein the compound is present at a concentration of about 0.09%-0.5% w/v.

40. The method of claim 38, wherein the compound is present at a concentration of about 0.1% w/v.

41. The method of claim 39, wherein the sulfobutylether-β-cyclodextrin is present at a concentration of about 9.5% w/v.

* * * * *